United States Patent
Sylvester et al.

(10) Patent No.: US 8,993,844 B1
(45) Date of Patent: Mar. 31, 2015

(54) PRODUCTION OF SPIDER SILK PROTEIN IN CORN

(75) Inventors: Anne W. Sylvester, Laramie, WY (US); Randolph V. Lewis, Nibley, UT (US); David Jackson, Brooklyn, NY (US)

(73) Assignee: University of Wyoming, Laramie, WY (US)

( * ) Notice: Subject to any disclaimer, the term of this patent is extended or adjusted under 35 U.S.C. 154(b) by 557 days.

(21) Appl. No.: 13/117,643

(22) Filed: May 27, 2011

Related U.S. Application Data

(60) Provisional application No. 61/348,997, filed on May 27, 2010.

(51) Int. Cl.
| | |
|---|---|
| *C12N 15/82* | (2006.01) |
| *A01H 5/00* | (2006.01) |
| *C07H 21/04* | (2006.01) |
| *C12P 21/02* | (2006.01) |
| *C12N 15/12* | (2006.01) |

(52) U.S. Cl.
CPC .................................. *C12N 15/8257* (2013.01)
USPC ....... 800/288; 800/287; 800/320.1; 536/23.5; 435/69.1; 435/320.1

(58) Field of Classification Search
None
See application file for complete search history.

(56) References Cited

U.S. PATENT DOCUMENTS

| | | | |
|---|---|---|---|
| 6,403,862 B1 | 6/2002 | Jiao et al. | |
| 6,608,242 B1 | 8/2003 | Yang | |
| 6,667,153 B1 * | 12/2003 | Thomas | 435/6.14 |
| 6,747,189 B1 | 6/2004 | McElroy et al. | |
| 7,119,255 B2 | 10/2006 | Betts et al. | |
| 7,157,629 B2 | 1/2007 | Cho et al. | |
| 7,288,391 B2 * | 10/2007 | Roth et al. | 435/69.1 |
| 7,411,112 B2 | 8/2008 | Diehn et al. | |
| 7,605,302 B2 | 10/2009 | Crane et al. | |
| 7,612,251 B2 | 11/2009 | Albertsen et al. | |
| 7,629,455 B2 | 12/2009 | Nelson et al. | |
| 7,915,478 B2 | 3/2011 | Albertsen et al. | |

FOREIGN PATENT DOCUMENTS

| | | | | |
|---|---|---|---|---|
| WO | WO 98/02563 | * | 1/1998 | C12N 15/82 |

OTHER PUBLICATIONS

GenBank AC144717, published Jul. 26, 2003.*
Pang et al (Plant Physiol., 112, pp. 893-900, 1996).*
Ramessar et al (Plant Science, 174(4), pp. 409-419, 2008).*
AF090446.1 (2003; see alignment below).*
AY646072 (2008; see alignment below).*
Mohanty et al. "Advancing Cell Biology and Functional Genomics in Maize Using Fluorescent Protein-Tagged Lines" Plant Physiology, Feb. 2009, vol. 149, pp. 601-605, American Society of Plant Biologists.
Mohanty et al "Methods for Generation and Analysis of Fluorescent Protein-Tagged Maize Lines" Methods in Molecular Biology: Transgenic Maize, 2009, vol. 526, pp. 71-89, Humana Press.

* cited by examiner

*Primary Examiner* — David T Fox
*Assistant Examiner* — Stephen Uyeno
(74) *Attorney, Agent, or Firm* — Cochran Freund & Young LLC; James M. Weatherly

(57) ABSTRACT

Methods for the production of synthetic spider silk-like proteins in corn endosperm or plant shoot tissue are provided. The present invention provides further methods for the identification of synthetic spider silk-like proteins in corn endosperm or plant shoot tissue.

9 Claims, 4 Drawing Sheets

PRODUCTION OF SPIDER SILK PROTEIN IN CORN

CROSS-REFERENCE TO RELATED APPLICATIONS

This application in a non-provisional patent application of and claims priority to U.S. Provisional Patent Application No. 61/348,997, filed on May 27, 2010, which is herein incorporated by reference in its entirety.

ACKNOWLEDGEMENT OF FEDERAL RESEARCH SUPPORT

This invention was made, at least in part, with government support under NSF DBI #0501862 awarded by the National Science Foundation and NIH #EB000490 awarded by the National Institute of Health. Accordingly, the United States government has certain rights in this invention.

FIELD

The present disclosure relates to the field of molecular biology and plant genetics. More specifically, disclosed is one or more methods to produce spider silk and synthetic spider silk-like proteins in plant tissue such as plant endosperm tissue or shoot tissue (including shoot meristem, other non-photosynthetic tissue and leaf tissue). Also disclosed are methods to identify the presence of spider silk and synthetic spider silk-like proteins expressed in plant endosperm tissue or shoot tissue.

SUBMISSION OF SEQUENCE LISTING

The Sequence Listing associated with this application is filed in electronic format via EFS-Web and hereby incorporated by reference into the specification in its entirety.

BACKGROUND

Increasing demands for materials and fabrics that are both lightweight and flexible without compromising strength and durability has created a need for new fibers possessing higher tolerances for such properties as elasticity, denier, tensile strength and modulus. The search for a better fiber has led to the investigation of fibers produced in nature, some of which possess remarkable qualities. One of those fibers is derived from spider or insect silk, which includes a group of externally spun fibrous protein secretions.

Silks are produced by over 30,000 species of spiders and by many other insects, particularly in the order Lepidoptera. Few of these silks have been studied in detail. The cocoon silk of the domesticated silkworm *Bombyx mori* and the dragline silk of the orb-weaving spider *Nephila clavipes* are among the best characterized. Although the structural proteins from the cocoon silk and the dragline silk are quite different from each other in their primary amino acid sequences, they share remarkable similarities in many aspects. They are extremely glycine and alanine-rich proteins. Fibroin, a structural protein of the cocoon silk, contains 42.9% glycine and 30% alanine Spidroin 1, a major component of the dragline silk, contains 37.1% glycine and 21.1% alanine They are also highly repetitive proteins. The conserved crystalline domains in the heavy chain of the Fibroin and a stretch of polyalanine in Spidroin 1 are repeated numerous times throughout entire molecules. These crystalline domains are surrounded by larger non-repetitive amorphous domains in every 1 to 2 kilobases in the heavy chain of Fibroin, and by shorter repeated GXG amorphous domains in tandem in Spidroin 1. They are also shear sensitive due to their high copy number of the crystalline domains. During fiber spinning, the crystalline repeats are able to form anti-parallel-pleated sheets, so that silk protein is turned into semi-crystalline fiber with amorphous flexible chains reinforced by strong and stiff crystals.

Spider dragline silk has a tensile strength of over 200 ksi with an elasticity of nearly 35%, which makes it more difficult to break than either KEVLAR™ fibers or steel. When spun into fibers, spider silk may have application in the bulk clothing industries as well as being applicable for certain kinds of high strength uses such as rope, surgical sutures, flexible tie downs for certain electrical components and even as a biomaterial for implantation (e.g., artificial ligaments or aortic banding). Additionally these fibers may be mixed with various plastics and/or resins to prepare a fiber-reinforced plastic and/or resin product.

Traditional silk production from silkworm involves growing mulberry leaves, raising silkworms, harvesting cocoons, and processing of silk fibers. It is labor intensive and time consuming and therefore prohibitively expensive. The natural defects of the silkworm silk, such as the tendency to wrinkle and the irregularity of fiber diameter further limits its application. Similarly, the mass production of the dragline silk from spiders is not plausible because only small amounts are available from each spider. Furthermore, multiple forms of spider silks are produced simultaneously by any given spider. The resulting mixture has less application than a single isolated silk because the different spider silk proteins have different properties and are not easily separated. Thus, the prospect of producing commercial quantities of spider silk from a natural source is not a practical one and there remains a need for an alternate mode of production.

By using molecular recombination techniques, one can introduce foreign genes or artificially synthesized DNA fragments into different host organisms for the purpose of expressing desired protein products in commercially useful quantities. Such methods usually involve joining appropriate fragments of DNA to a vector molecule, which is then introduced into a recipient organism by transformation. Transformants are selected using a selectable marker on the vector, or by a genetic or biochemical screen to identify the cloned fragment.

While the techniques of foreign gene expression in the host cell are well known and widely practiced, the synthesis of foreign polypeptides containing high numbers of repeating units poses unique problems. Genes encoding proteins of this type are prone to genetic instability due to the repeating sequences, which result in truncated product instead of the full size protein.

The recent advances in cDNA sequencing of cocoon silk and dragline silk have permitted the synthesis of artificial genes for spider silk-like proteins with sequence and structural similarity to the native proteins. These artificial genes mimicked sequence arrays of natural cocoon silk from *B. mori* and dragline silk from *N. clavipes*, and had been introduced into microorganisms such as *Escherichia coli*, *Pichia pastoris*, and *Saccharomyces cerevisiae*. Synthetic spider silk proteins have been produced in these microorganisms through fermentation.

Many recombinant proteins have been produced in transgenic plants. Plant genetic engineering combines modern molecular recombination technology and agricultural crop production. However there are striking compositional and structural differences between silks and spider silk-like proteins and native plant proteins. For example, spider silk-like proteins are very glycine and alanine-rich, highly repetitive, and semi-crystalline in structure. These are characteristics not found in most plant proteins. Thus, introduction and expression of spider silk-like proteins genes in plant cells may pose a number of difficulties. For example, the repetitive sequence of spider silk-like protein genes may be a target for DNA deletion and rearrangement in plant cells.

Alternatively, translation of glycine and alanine-rich spider silk-like proteins might prematurely exhaust glycine and alanine and tRNA pools in plant cells. Finally, accumulation of semi-crystalline spider silk-like proteins may be recognized and degraded by the housekeeping mechanisms in the plant.

The methods known in the art for the expression of spider silk and spider silk-like proteins are useful for production in microbial systems. However, they are not applicable to the production of silk or spider silk-like proteins in plants. The use of a plant platform, such as maize cells for the production of silk and silk-like proteins, has several advantages over a microbial platform. For example, as a renewable resource, a plant platform requires far less energy and material consumption than microbial methods. Similarly, a plant platform represents a far greater available biomass for protein production than a microbial system.

There are several advantages of expressing spider silk proteins in plants over existing technologies. Corn endosperm, in particular, stores high concentrations of proteins in storage bodies, and targeting and processing can be directed by plant specific sequences.

The problem to be solved therefore is to provide a method to produce synthetic spider silk in the endospermor shoot tissue of plants and to easily identify when synthetic spider silk proteins have been expressed in the plant endosperm or shoot tissue.

The foregoing examples of the related art and limitations related therewith are intended to be illustrative and not exclusive. Other limitations of the related art will become apparent to those of skill in the art upon a reading of the specification.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

An embodiment of the present invention provides DNA constructs for the expression of spider silk proteins in plant endosperm. Such DNA constructs may be represented as PeUrr-SS-FP-X or PeUrr-FP-SS-X wherein PeUrr is a plant endosperm upstream regulatory region (URR, which includes upstream regulatory sequence, promoter region, transcriptional start site and a translation start codon), SS is a synthetic spider silk protein coding sequence, FP is a fluorescent protein coding sequence and X is downstream regulatory region (DRR, including a translational stop sequence, transcription terminator sequence and downstream regulatory region). Further, the DNA construct is stably integrated into a plant DNA genome under conditions suitable for the expression of the DNA construct in a plant endosperm, where the DNA construct expresses a protein in the plant endosperm. The expressed protein is a spider silk protein with a fluorescent marker indicating successful integration and expression.

An embodiment of the present invention provides DNA constructs for the expression of spider silk proteins in corn plant endosperm. Such DNA constructs are represented as CeUrr-SS-FP-X or CeUrr-FP-SS-X wherein CeUrr is a corn plant endosperm upstream regulatory region, SS is a synthetic spider silk protein coding sequence, FP is a fluorescent protein coding sequence and X is a downstream regulatory region. Further, the DNA construct is stably integrated into a plant DNA genome under conditions suitable for the expression of the DNA construct in a corn plant endosperm, where the DNA construct expresses a protein in the corn plant endosperm. The expressed protein is a spider silk protein with a fluorescent marker indicating successful integration and expression.

An embodiment of the present invention provides DNA constructs for the expression of spider silk proteins in plant shoot tissue (which includes leaf, meristematic and other non-photosynthetic tissue). Such DNA constructs may be represented as PsUrr-SS-FP-X or PsUrr-FP-SS-X wherein PsUrr is a plant shoot tissue upstream regulatory region, SS is a synthetic spider silk protein coding sequence, FP is a fluorescent protein coding sequence and X is a downstream regulatory region. Further, the DNA construct is stably integrated into a plant DNA genome under conditions suitable for the expression of the DNA construct in a plant shoot, where the DNA construct expresses a protein in the plant shoot. The expressed protein is a spider silk protein with a fluorescent marker indicating successful integration and expression.

In an another embodiment of the present invention a DNA construct is provided which comprises a nucleic acid having the sequence comprising a plant endosperm tissue promoter selected from the group comprising SEQ ID NO:1, SEQ ID NO:2, SEQ ID NO:3, SEQ ID NO:4, SEQ ID NO:6 and SEQ ID NO:7 where the plant endosperm tissue promoter is operably linked to a synthetic spider silk protein coding sequence selected from the group comprising SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40.

An embodiment of the present invention provides DNA construct having a nucleic acid having the sequence comprising a corn plant endosperm tissue promoter selected from the group comprising SEQ ID NO:1, SEQ ID NO:2, SEQ ID NO:3, SEQ ID NO:4, SEQ ID NO:6 and SEQ ID NO:7 and where the corn plant endosperm tissue promoter is operably linked to a synthetic spider silk protein coding sequence selected from the group comprising SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40.

In an another embodiment of the present invention a DNA construct is provided which comprises a nucleic acid having the sequence comprising a plant shoot-tissue promoter selected from the group comprising SEQ ID NO:54, SEQ ID NO:55, SEQ ID NO:56, SEQ ID NO:61, SEQ ID NO:62, and SEQ ID NO:68 where the shoot tissue promoter is operably linked to a synthetic spider silk protein coding sequence selected from the group comprising SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40.

In an another embodiment of the present invention a DNA construct is provided which further comprises a synthetic spider silk protein coding sequence operably linked to a transcription terminator sequence.

In an another embodiment of the present invention a DNA construct is provided which further comprises a sortable marker operably linked to the 5' end of said synthetic spider silk protein coding sequence where the sortable marker is selected from the group comprising SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:46, SEQ ID NO:47, SEQ ID NO:48, SEQ ID NO:49, SEQ ID NO:50, SEQ ID NO:51, SEQ ID NO:52, and SEQ ID NO:53.

In an another embodiment of the present invention a DNA construct is provided which further comprises a sortable marker operably linked to the 3' end of said synthetic spider silk protein coding sequence, where the sortable marker is selected from the group comprising SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:46, SEQ ID NO:47, SEQ ID NO:48, SEQ ID NO:49, SEQ ID NO:50, SEQ ID NO:51, SEQ ID NO:52, and SEQ ID NO:53.

In an another embodiment of the present invention a transgenic plant is provided having a DNA construct stably integrated into the DNA construct genome under conditions suitable for the expression of the DNA construct in a plant endosperm, where the DNA construct expresses a protein in the plant endosperm. The expressed protein is a spider silk protein.

In an another embodiment of the present invention a method is provided for producing synthetic spider silk proteins in the tissue of plant endosperm which comprises growing a transgenic plant having a DNA construct stably integrated into the DNA genome under conditions suitable for the expression of the DNA construct in a plant endosperm. The DNA construct expresses a protein in the plant endosperm, wherein the expressed protein is a spider silk protein.

In an another embodiment of the present invention a transgenic corn plant is provided having a DNA construct stably integrated into the DNA genome under conditions suitable for the expression of the DNA construct in a corn plant endosperm, where the DNA construct expresses a protein in the plant endosperm. The expressed protein is a spider silk protein.

In an another embodiment of the present invention a method for producing synthetic spider silk proteins in the tissue of corn plant endosperm is provided which comprises growing a transgenic plant having a DNA construct stably integrated into the DNA genome under conditions suitable for the expression of the DNA construct in a corn plant endosperm. The DNA construct expresses a protein in the corn plant endosperm, wherein the expressed protein is a spider silk protein.

In an another embodiment of the present invention a transgenic plant is provided having a DNA construct stably integrated into the DNA construct genome under conditions suitable for the expression of the DNA construct in a plant shoot, where the DNA construct expresses a protein in the plant shoot. The expressed protein is a spider silk protein.

In an another embodiment of the present invention to provide a method for producing synthetic spider silk proteins in the plant shoot which comprises growing a transgenic plant having a DNA construct stably integrated into the DNA genome under conditions suitable for the expression of the DNA construct in a plant shoot. The DNA construct expresses a protein in the plant shoot, wherein the expressed protein is a spider silk protein.

Various components are referred to herein as "operably linked", "linked" or "operably associated." As used herein, "operably linked", "linked" or "operably associated" refers to nucleic acid sequences on a single nucleic acid fragment so that the function of one is affected by the other. For example, a promoter is operably linked with a coding sequence when it is capable of affecting the expression of that coding sequence.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, "sometime" means at some indefinite or indeterminate point of time. So for example, as used herein, "sometime after" means following, whether immediately following or at some indefinite or indeterminate point of time following the prior act.

Various embodiments of the present invention are set forth in the Detailed Description as provided herein and as embodied by the claims. It should be understood, however, that this Summary does not contain all of the aspects and embodiments of the present invention, is not meant to be limiting or restrictive in any manner, and that the invention(s) as disclosed herein is/are understood by those of ordinary skill in the art to encompass obvious improvements and modifications thereto.

Additional advantages of the present invention will become readily apparent from the following discussion, particularly when taken together with the accompanying drawings and sequence listings.

SEQUENCE LISTINGS

SEQ ID NO:1 discloses the leader nucleic acid sequence of one embodiment of the present invention.

SEQ ID NO:2 discloses the nucleic sequence for the Zein gene (floury2) (Genbank Accession Number MZEZFL2).

SEQ ID NO:3 discloses the amino acid sequence for the Zein gene (floury2) (Genbank Accession Number AAA76580).

SEQ ID NO:4 discloses the nucleic acid sequence which encodes the regulatory region of the endosperm tissue promoter of one embodiment of the present invention.

SEQ ID NO:5 discloses the nucleic acid sequence which encodes the regulatory region of the transcription terminator of one embodiment of the present invention.

SEQ ID NO:6 discloses the nucleic acid sequence which encodes the *Triticum aestivum* endosperm regulatory region containing the promoter region and 5' UTR of the (SbeIIa) gene (Genbank Accession Number AY357072).

SEQ ID NO:7 discloses the nucleic acid sequence of nucleic acid sequence which encodes the regulatory region of the Opaque 2 gene endosperm tissue promoter (Genbank Accession Number: FJ935743).

SEQ ID NO:8 discloses the nucleic acid sequence for the forward primer 1 for the amplification of the promoter and the partial gene sequence of SEQ ID NO:1.

SEQ ID NO:9 discloses the nucleic acid sequence for the reverse primer 2 for the amplification of the promoter and the partial gene sequence of SEQ ID NO:1 of the present invention.

SEQ ID NO:10 discloses the nucleic acid sequence for forward primer for the amplification of the partial gene sequence of SEQ ID NO:1 and the 3' UTR which includes the transcription terminator.

SEQ ID NO:11 discloses the reverse primer for the amplification of the promoter and gene sequence of SEQ ID NO:1.

SEQ ID NO:12 discloses the nucleic acid sequence of the Red Fluorescent Protein (mRFP).

SEQ ID NO:13 discloses the protein sequence of the Red Fluorescent Protein (mRFP).

SEQ ID NO:14 discloses the nucleic acid sequence of the Cyan Fluorescent Protein (CFP) (Genbank Accession Number: AY646072).

SEQ ID NO:15 discloses the protein sequence of the Cyan Fluorescent Protein (CFP) (Genbank Accession Number: AAU06851).

SEQ ID NO:16 discloses the nucleic acid sequence of the Green Fluorescent Protein pCmGFP (GFP) (Genbank Accession Number: FJ172221).

SEQ ID NO:17 discloses the protein sequence of the Green Fluorescent Protein pCmGFP (GFP) (Genbank Accession Number: ACJ06700).

SEQ ID NO:18 discloses the nucleic acid sequence of the Yellow Fluorescent Protein (YFP) (Genbank Accession Number: GQ221700).

SEQ ID NO:19 discloses the protein sequence of the Yellow Fluorescent Protein (YFP) (Genbank Accession Number: GQ221700).

SEQ ID NO:20 discloses the synthetic spider silk protein sequence $E_4S_4$ of a *Nephila clavipes* MaSp 2 construct.

SEQ ID NO:21 discloses the synthetic spider silk protein sequence $E_4S_8$ of a *Nephila clavipes* MaSp 2 construct.

SEQ ID NO:22 discloses the synthetic spider silk protein sequence $E_4S_{16}$ of a *Nephila clavipes* MaSp 2 construct.

SEQ ID NO:23 discloses the synthetic spider silk protein sequence $E_{16}S_8$ of a *Nephila clavipes* MaSp 2 construct.

SEQ ID NO:24 discloses the synthetic spider silk protein sequence $E_1S_8$ of a *Argiope* sp. MaSp 2 construct.

SEQ ID NO:25 discloses the synthetic spider silk protein sequence $E_2S_8$ of a *Argiope* sp. MaSp 2 construct.

SEQ ID NO:26 discloses the synthetic spider silk protein sequence $E_3S_8$ of a *Argiope* sp. MaSp 2 construct.

SEQ ID NO:27 discloses the recombinant synthetic spider silk protein sequences made up of the fusion protein sequence $A1S8_{20}$.

SEQ ID NO:28 discloses the recombinant synthetic spider silk protein sequences made up of the fusion protein sequence $A2S8_{14}$.

SEQ ID NO:29 discloses the recombinant synthetic spider silk protein sequences made up of the fusion protein sequence $A4S8_8$.

SEQ ID NO:30 discloses the recombinant synthetic spider silk protein sequences made up of the fusion protein sequence $A_{40}$.

SEQ ID NO:31 discloses the recombinant synthetic spider silk protein sequences made up of the fusion protein sequence $Y1S8_{20}$.

SEQ ID NO:32 discloses the recombinant synthetic spider silk protein sequences made up of the fusion protein sequence $Y2S8_{14}$.

SEQ ID NO:33 discloses the recombinant synthetic spider silk protein sequences made up of the fusion protein sequence $Y4S8_8$.

SEQ ID NO:34 discloses the recombinant synthetic spider silk protein sequences made up of the fusion protein sequence $Y_{47}$.

SEQ ID NO:35 discloses the spider silk nucleic acid sequence made up of the sequence PXP.

SEQ ID NO:36 discloses the spider silk protein sequence made up of the sequence PXP.

SEQ ID NO:37 discloses the spider silk nucleic acid sequence made up of the sequence QQ.

SEQ ID NO:38 discloses the synthetic spider silk protein sequence made up of the sequence QQ.

SEQ ID NO:39 discloses the synthetic spider silk nucleic acid sequence made up of the full piriform sequence.

SEQ ID NO:40 discloses the synthetic spider silk protein sequence made up of the full piriform sequence.

SEQ ID NO:41 discloses the nucleic acid sequence for forward primer for the Red Fluorescent Protein (mRFP).

SEQ ID NO:42 discloses the nucleic acid sequence for reverse primer for the Red Fluorescent Protein (mRFP).

SEQ ID NO:43 discloses the nucleic acid sequence for forward primer for Cyan Fluorescent Protein (CFP) and Yellow Fluorescent Protein (YFP).

SEQ ID NO:44 discloses the nucleic acid sequence for reverse primer for the Cyan Fluorescent Protein (CFP) and Yellow Fluorescent Protein (YFP).

SEQ ID NO:45 discloses the complete nucleic acid sequence containing the promoter of one embodiment of the present invention, the Zein gene and the transcription terminator.

SEQ ID NO:46 discloses the nucleic acid sequence of the maize specific Teal Fluorescent Protein (mTFP).

SEQ ID NO:47 discloses the protein sequence of the maize specific Teal Fluorescent Protein (mTFP).

SEQ ID NO:48 discloses the nucleic acid sequence of the maize specific Blue Fluorescent Protein (mBFP).

SEQ ID NO:49 discloses the protein sequence of the maize specific Blue Fluorescent Protein (mBFP).

SEQ ID NO:50 discloses the nucleic acid sequence of the maize specific Chemy Fluorescent Protein, mCherry (mChFP).

SEQ ID NO:51 discloses the protein sequence of the maize specific Chemy Fluorescent Protein, mCherry (mChFP).

SEQ ID NO:52 discloses the nucleic acid sequence of the maize specific Cerulean Fluorescent Protein (mCeFP).

SEQ ID NO:53 discloses the protein sequence of the maize specific Cerulean Fluorescent Protein (mCeFP).

SEQ ID NO:54 discloses the *Nicotiana tabacum* nucleic acid sequence which encodes the regulatory region of the Dfr2 gene leaf tissue promoter, and 5' UTR (Genbank Accession Number FJ472649).

SEQ ID NO:55 discloses the *Nicotiana tabacum* nucleic acid sequence which encodes the regulatory region of the Dfr2 gene leaf tissue promoter, (Genbank Accession Number FJ472649).

SEQ ID NO:56 discloses the *Nicotiana plumbaginifolia* nucleic acid sequence which encode the regulatory region of the Cab gene and leaf tissue promoters. (Genbank Accession Number X12512).

SEQ ID NO:57 discloses the nucleic acid sequence for forward primer and linker sequence for the maize specific blue (mBFP), cherry (mChFP) and teal (mTFP) Fluorescent Protein.

SEQ ID NO:58 discloses the nucleic acid sequence for reverse primer and linker sequence for the maize specific blue (mBFP), cherry (mChFP) and teal (mTFP) Fluorescent Protein.

SEQ ID NO:59 discloses the nucleic acid sequence for forward primer and linker sequence for the maize specific cerulean Fluorescent Protein (mCeFP).

SEQ ID NO:60 discloses the nucleic acid sequence for reverse primer and linker sequences for the maize specific cerulean Fluorescent Protein (mCeFP).

SEQ ID NO:61 discloses the *Zea mays* nucleic acid sequence which encodes the RAB2A gene shoot tissue regulatory region with the promoter and 3' UTR.

SEQ ID NO:62 discloses the *Zea mays* nucleic acid sequence which encodes the RAB2A gene shoot tissue promoter.

SEQ ID NO:63 discloses the nucleic acid sequence for the primer 1 for the amplification of the promoter and the partial gene sequence of SEQ ID NO:61 and SEQ ID NO:62.

SEQ ID NO:64 discloses the nucleic acid sequence for the reverse primer 2 for the amplification of the promoter and the partial gene sequence of SEQ ID NO:61 and SEQ ID NO:62 of the present invention.

SEQ ID NO:65 discloses the nucleic acid sequence for the forward primer 3 for the amplification of the promoter and the partial gene sequence of SEQ ID NO:61.

SEQ ID NO:66 discloses the nucleic acid sequence for the reverse primer 4 for the amplification of the promoter and the partial gene sequence of SEQ ID NO:61 and SEQ ID NO:62.

SEQ ID NO:67 discloses the nucleic acid sequence for the forward primer 3 for the amplification of the promoter sequence of SEQ ID NO:62.

SEQ ID NO:68 discloses the *Hordeum vulgare* nucleic acid sequence which encodes the myb2 gene shoot tissue promoter (Genbank Accession Number X70876).

BRIEF DESCRIPTION OF THE DRAWINGS

To further clarify the above and other advantages and features of the present invention, a more particular description of the invention is rendered by reference to specific embodiments thereof which are illustrated in the appended drawings. It is appreciated that these drawings depict only typical embodiments of the invention and are therefore not to be considered limiting of its scope. The invention is described and explained with additional specificity and detail through the use of the accompanying drawings in which.

The drawings are not necessarily to scale.

DETAILED DESCRIPTION

The present invention provides one or more methods for the expression of spider silk and spider silk-like proteins in the endosperm or shoot tissue of plants and in particular corn plants. The term "plant" includes reference to an immature or mature whole plant, including a plant from which seed, grain, anthers, or pistils have been removed. A seed or embryo that will produce the plant is also considered to be the plant. The present invention further provides one or more methods for the identification of spider silk and spider silk-like proteins in the endosperm or shoot tissue of a plant and in particular corn plants. The spider silk and spider silk-like proteins of the present invention may have properties suitable for fabrics, or alternatively may be useful in materials.

In one or more embodiments of the present invention one or more DNA constructs are provided for use in expression of synthetic spider silk in plant endosperm represented by PeUrr-SS-FP-X and variations thereof, by providing at least one plant endosperm tissue promoter operably linked to at least one synthetic spider silk protein coding sequence. The synthetic spider silk protein is also operably linked to a sortable marker which is operably linked to a transcription terminator sequence. Transgenic plants expressing the synthetic spider silk protein genes are then generated. The preferred embodiment of the transgenic plants of the present invention is corn plants and corn plant endosperm promoters wherein the construct is represent by CeUrr-SS-FP-X and variations thereof. However, the transgenic plants may include, but are not limited to other plants, such as barley, rice, wheat, sorghum and millet.

In one or more embodiments of the present invention one or more DNA constructs are provided for use in expression of synthetic spider silk in shoot tissue, represented by PsUrr-SS-FP-X and variations thereof, by providing at least one plant shoot tissue promoter operably linked to at least one synthetic spider silk protein coding sequence. The synthetic spider silk protein coding sequence is also operably linked to a sortable marker which is operably linked to a transcription terminator sequence. Transgenic plants expressing the synthetic spider silk protein genes are then generated. The preferred embodiment of the transgenic plants of one embodiment of the present invention is but not limited to, corn plants. However, the transgenic plants may include, but are not limited to other plants, such as barley, corn, tobacco, rice, wheat, sorghum and millet.

Figure 1:
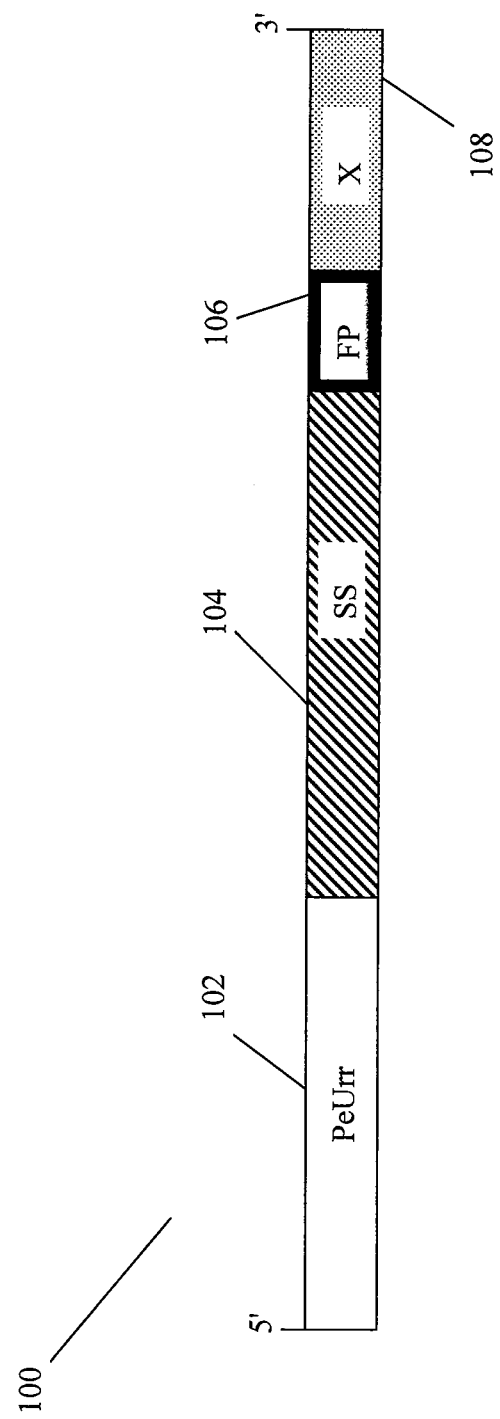
FIG. 1 is a map of a DNA construct, represented as PeUrr-SS-FP-X that includes (from 5' to 3'), a plant endosperm tissue upstream regulatory region, a synthetic spider silk protein coding sequence, a fluorescent protein coding sequence with linker sequences and a downstream regulatory region including transcription terminator sequence.

The present invention provides one or more recombinant constructs that are suitable for the expression of spider silk proteins in plant endosperm such as corn and plant shoot tissue. As shown in FIG. 1, the construct of one embodiment of the present invention is generally represented as PeUrr-SS-FP-X, 100, wherein PeUrr is the upstream regulatory region including the plant endosperm tissue promoter, the transcription start sequence, and the start codon (ATG) 102, SS is a synthetic spider silk protein coding sequence 104, FP, a sortable marker, is a fluorescent protein region that includes a linker sequence on the 5' end of the fluorescent protein coding sequence and linker sequence on the 3' end of the fluorescent protein coding 106 and X is a downstream regulatory region including the stop codon (TGA, TAG or TAA) and the transcription terminator sequence 108. Each of these four components is operably linked to the next, i.e., the plant endosperm tissue upstream regulatory region is operably linked to the 5' end of the synthetic spider silk sequence encoding the synthetic spider silk protein, the synthetic spider silk protein coding sequence is operably linked to the 5' end of the fluorescent protein coding sequence and the fluorescent protein coding sequence is operably linked to 5' end of the downstream regulatory region. Synthetic spider silk protein may also be expressed in variations of the construct of FIG. 1 including but not limited to PeUrr-SS-X, PeUrr-SS-FP and PeUrr-SS.

Figure 2:
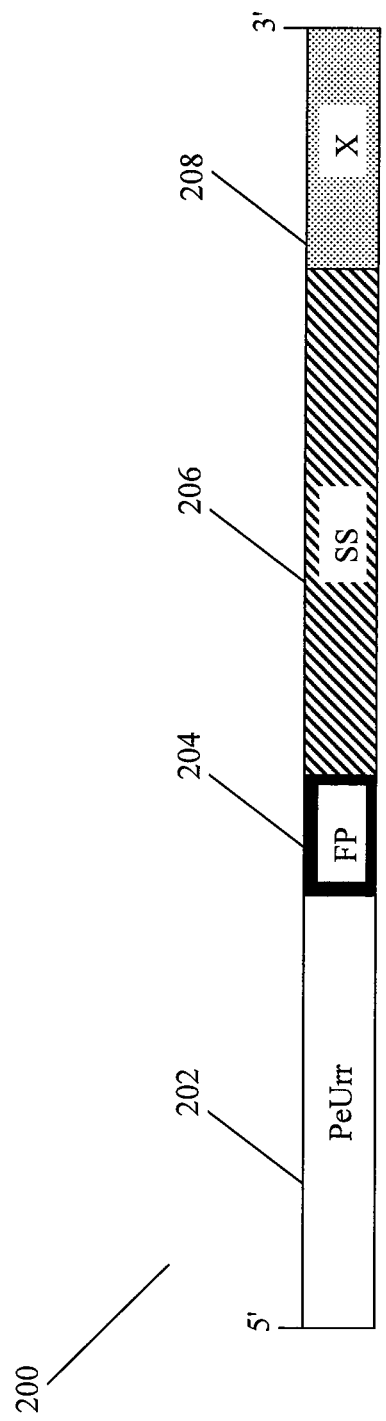
FIG. 2 is a map of a DNA construct, represented as PeUrr-FP-SS-X that includes (from 5' to 3'), a plant endosperm tissue upstream regulatory region, a fluorescent protein coding sequence with linker sequences, a synthetic spider silk protein coding sequence and a downstream regulatory region including transcription terminator sequence.

As shown in FIG. 2, the construct of another embodiment of the present invention is generally represented as PeUrr-FP-SS-X, 200, wherein PeUrr is the upstream regulatory region including the corn endosperm tissue promoter, the transcription start sequence, and the start codon (ATG) 202, FP, a sortable marker, is a fluorescent protein region that includes a linker sequence on the 5' end of the fluorescent protein coding sequence and linker sequence on the 3' end of the fluorescent protein coding, 204 SS is a synthetic spider silk protein coding sequence, 206 and X, the transcription terminator, is a downstream regulatory region including the stop codon (TGA, TAG or TAA) and the transcription terminator sequence 208. Each of these four components is operably linked to the next, i.e., the plant endosperm upstream regulatory region is operably linked to the 5' end of the synthetic spider silk sequence encoding the synthetic spider silk protein, the synthetic spider silk protein coding sequence is operably linked to the 5' end of the fluorescent protein coding sequence and the fluorescent protein coding sequence is operably linked to 5' end of the downstream regulatory region. FIG. 2, including but not limited to PeUrr-SS-X, PeUrr-FP-SS and PeUrr-SS.

Figure 3:
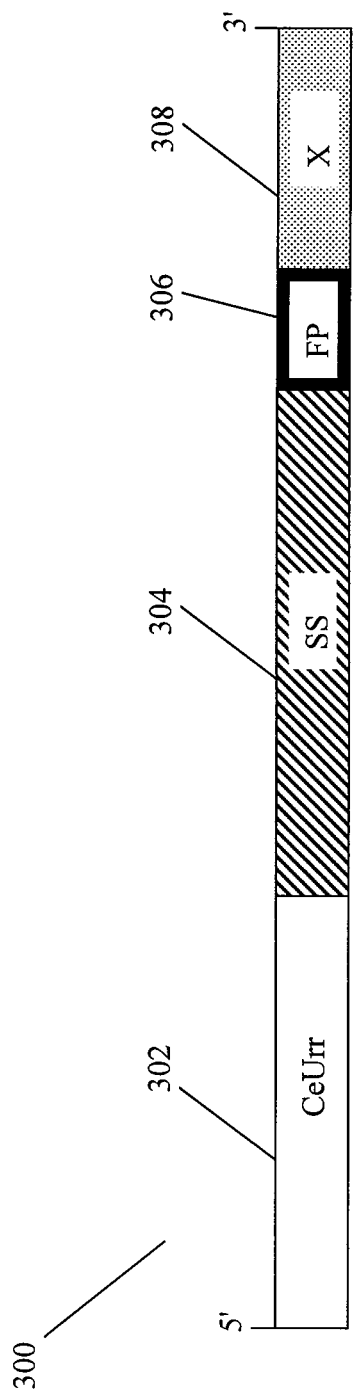
FIG. 3 is a map of a DNA construct, represented as CeUrr-SS-FP-X that includes (from 5' to 3'), a corn endosperm tissue upstream regulatory region, a synthetic spider silk protein coding sequence, a fluorescent protein coding sequence with linker sequences and a downstream regulatory region including transcription terminator sequence.

As shown in FIG. 3, the construct of another embodiment of the present invention is generally represented as CeUrr-SS-FP-X, 300, wherein CeUrr is the upstream regulatory region including the corn endosperm tissue promoter, the transcription start sequence, and the start codon (ATG) 302, SS is a synthetic spider silk protein coding sequence 304, FP, a sortable marker, is a fluorescent protein region that includes a linker sequence on the 5' end of the fluorescent protein coding sequence and linker sequence on the 3' end of the fluorescent protein coding 306 and X, the transcription terminator, is a downstream regulatory region including the stop codon (TGA, TAG or TAA) and the transcription terminator sequence 308. Each of these four components is operably linked to the next, i.e., the corn endosperm tissue upstream regulatory region is operably linked to the 5' end of the synthetic spider silk sequence encoding the synthetic spider silk protein, the synthetic spider silk protein coding sequence is operably linked to the 5' end of the fluorescent protein coding sequence and the fluorescent protein coding sequence is operably linked to 5' end of the downstream regulatory region. Spider silk protein may also be expressed in variations of the construct of FIG. 3 including but not limited to CeUrr-SS-X, CeUrr-SS-FP, CeUrr-SS, CeUrr-FP-SS-X, and CeUrr-FP-SS.

Figure 4:
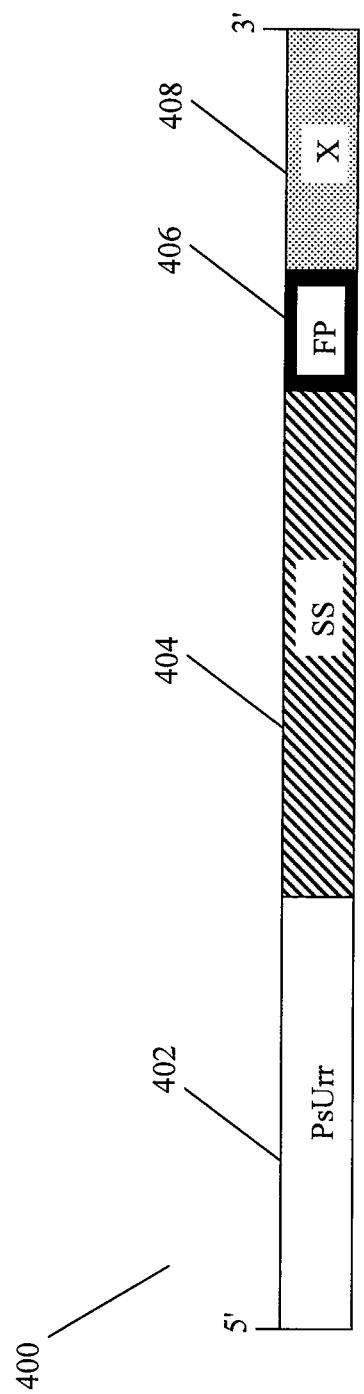
FIG. 4 is a map of a DNA construct, represented as PsUrr-SS-FP-X that includes (from 5' to 3'), a plant shoot tissue upstream regulatory region, a synthetic spider silk protein coding sequence, a fluorescent protein coding sequence with linker sequences and a downstream regulatory region including transcription terminator sequence.

As shown in FIG. 4, the construct of one embodiment of the present invention may be generally represented as PsUrr-SS-FP-X, 400, wherein PsUrr is the upstream regulatory region including the plant shoot tissue promoter, the transcription start sequence, and the start codon (ATG) 402, SS is a synthetic spider silk protein coding sequence 404, FP, a sortable marker, is a fluorescent protein region that includes a linker sequence on the 5' end of the fluorescent protein coding sequence and linker sequence on the 3' end of the fluorescent protein coding 406 and X is a downstream regulatory region including the stop codon (TGA, TAG or TAA) and the transcription terminator sequence 408. Each of these four components is operably linked to the next, i.e., the plant shoot tissue upstream regulatory region is operably linked to the 5' end of the synthetic spider silk sequence encoding the synthetic spider silk protein, the synthetic spider silk protein coding sequence is operably linked to the 5' end of the fluorescent protein coding sequence and the fluorescent protein coding sequence is operably linked to 5' end of the downstream regulatory region. Synthetic spider silk protein may also be expressed in variations of the construct of FIG. 4 including but not limited to PsUrr-SS-X, PsUrr-SS-FP, PsUrr-SS, PsUrr-FP-SS-X, and PsUrr-FP-SS.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice. The use of T-DNA to transform plant cells has received extensive study and are known to those skilled in the art. For introduction into plants, the chimeric genes of the invention can be inserted into binary vectors as described in the examples.

Other transformation methods are available to those skilled in the art, such as direct uptake of foreign DNA constructs, techniques of electroporation or high-velocity ballistic bombardment with metal particles coated with the nucleic acid constructs. Once transformed, the cells can be regenerated by those skilled in the art. Of particular relevance are the methods to transform foreign genes into commercially important crops, such as rapeseed, sunflower, soybean, rice and corn.

Transgenic plant cells are then placed in an appropriate selective medium for selection of transgenic cells, which are then grown to callus. (Please note that transgenic is used to indicate a plant, or photosynthetic organism including algae, which has been genetically modified to contain the DNA constructs of the present invention.) Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA, which has been introduced. A plasmid, vector or cassette which is a n extrachromosomal element is used to carry genes and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a cell. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region, which is not native to the gene from which the transcription initiation region is derived.

To confirm the presence of the transgenes in transgenic cells and plants, a polymerase chain reaction (PCR) amplification or Southern blot analysis can be performed using methods known to those skilled in the art. A PCR refers to a scientific technique to amplify a single or a few copies of a piece of DNA across several orders of magnitude, generating thousands to millions of copies of a particular DNA sequence. The present invention provides one or more methods to generate gene constructs including but not limited to the ttPCR method and the Gateway® Multisite method. The ttPCR method uses triple template PCR to generate the genomic sequence including 5' UTR, genomic gene sequence and 3'UTR with inserted fluorophor. A UTR refers to the untranslated region on either of two sections on either side of a coding sequence on a strand of mRNA. The ttPCR product is subsequently cloned using the Gateway® recombination vectors. The Gateway® Multisite method uses three-way or four-way multisite Gateway® cloning, which bypasses the need to generate three PCR products and instead prepares three to four Gateway® clones, which are subsequently cloned together into the final vector. The ttPCR method is efficient for small size genomic sequences <5 kb in size. The Gateway® Multisite cloning method is used for final gene sizes from 5-15 kb or larger.

Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics. Expression includes the process by which information from a gene is used in the synthesis of a functional gene product, such as the expression of spider silk proteins or synthetic spider silk proteins in the endosperm of maize. These products are often proteins, but in non-protein coding genes such as rRNA genes or tRNA genes, the product is a functional RNA. The process of gene expression is used by all known life, i.e., eukaryotes (including multicellular organisms), prokaryotes (bacteria and archaea), and viruses, to generate the macromolecular machinery for life. Several steps in the gene expression process may be modulated, including the transcription, up-regulation, RNA splicing, translation, and post-translational modification of a protein.

Generally, the DNA that is introduced into a plant is part of a construct. A construct is an artificially constructed segment of DNA that may be introduced into a target plant tissue or plant cell. The DNA may be a gene of interest, e.g., a coding sequence for a protein, or it may be a sequence that is capable of regulating expression of a gene, such as an antisense sequence, a sense suppression sequence, or a miRNA sequence. The construct typically includes regulatory regions operably linked to the 5' side of the DNA of interest and/or to the 3' side of the DNA of interest. Operably linked refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. A cassette containing all of these elements is also referred to herein as an expression cassette. The expression cassettes may additionally contain 5' leader sequences in the expression cassette construct. (A leader sequence is a nucleic acid sequence containing a promoter as well as the upstream region of a gene.) The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. The expression cassette may additionally contain selectable marker genes. Targeting constructs are engineered DNA molecules that encode genes and flanking sequences that enable the constructs to integrate into the host genome at (targeted) locations. Publicly available restriction enzymes may be used for the development of the constructs of the present invention. Targeting constructs depend upon homologous recombination to find their targets.

Other heterologous proteins encoded by the chimeric gene include polypeptides that form immunologically active epitopes, and enzymes that catalyze conversion of intracellular metabolites, with the consequent build-up of selected metabolites in the cells.

The expression cassette or chimeric genes in the transforming vector typically have a transcriptional termination region at the opposite end from the transcription initiation regulatory region. The transcriptional termination region may normally be associated with the transcriptional initiation region from a different gene. The transcriptional termination region may be selected, particularly for stability of the mRNA, to enhance expression. Illustrative transcriptional termination regions include the NOS terminator from *Agrobacterium* Ti plasmid and the rice α-amylase terminator.

A promoter is a DNA region, which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. The promoter may be any DNA sequence which shows transcriptional activity in the chosen plant cells, plant parts, or plants. The promoter may be inducible or constitutive. It may be naturally-occurring, may be composed of portions of various naturally-occurring promoters, or may be partially or totally synthetic. Also, the location of the promoter relative to the transcription start may be optimized. Many suitable promoters for use in plants are well known in the art, as are nucleotide sequences, which enhance expression of an associated expressible sequence.

A tissue-specific promoter of the DNA constructs of one or more embodiments of the present invention is a regulated promoter that is not expressed in all plant cells but only in one or more cell types in specific organs (such as leaves or seeds), specific tissues (such as embryo or cotyledon), or specific cell types (such as leaf parenchyma or seed storage cells). This also includes promoters that are temporally regulated, such as in early or late embryogenesis, during fruit ripening in developing seeds or fruit, in fully differentiated leaf, or at the onset of senescence. While the tissue promoter in the regulatory region upstream of the leader sequence of the Zein gene (SEQ ID NO:1) is one example of a promoter of a construct of one embodiment of the present invention, a number of promoters may be used in the practice of the constructs of the present invention, including but not limited to the *Triticum aestivum* endosperm (SbeIIa) promoter (SEQ ID NO:6) (Genbank Accession Number AY357072), the Opaque 2 gene endosperm tissue promoter (SEQ ID NO:7) (Genbank Accession Number FJ935743), the tobacco Dfr2 gene leaf tissue promoters, (SEQ ID NO:54) and (SEQ ID NO:55) (Genbank Accession Number FJ472649), the tobacco Cab gene leaf tissue promoter (SEQ ID NO:56) (Genbank Accession Number X12512), the *Zea mays* shoot tissue RAB2A gene (SEQ ID NO:61), the *Zea mays* shoot tissue RAB2A promoter (SEQ ID NO:62) and the *Hordeum vulgare* myb2 gene shoot tissue promoter (SEQ ID NO:68). The promoters can be selected based on the desired outcome. That is, the nucleic acids can be combined with constitutive, tissue preferred, or other promoters for expression in the host cell of interest. The promoter may be inducible or constitutive. It may be naturally-occurring, may be composed of portions of various naturally-occurring promoters, or may be partially or totally synthetic. Guidance for the design of promoters is commonly known in the art. In addition, the location of the promoter relative to the transcription start may be optimized. Many suitable promoters for use in plants are well known in the art, as are nucleotide sequences, which enhance expression of an associated expressible sequence.

Several tissue-specifically regulated genes and/or promoters have been reported in plants. These include genes encoding the seed storage proteins (such as napin, cruciferin, beta-conglycinin, glycinin and phaseolin), zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4). Particularly useful for seed-specific expression is the pea vicilin promoter. Other useful promoters for expression in mature leaves are those that are switched on at the onset of senescence, such as the SAG promoter from *Arabidopsis*.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PClSV enhancer element and the CaMV 35S enhancer element.

Preparation of Spider Silk-Encoding Nucleic Acid Molecules, Spider Silk Proteins, and Antibodies Thereto Spider silk or silk-like proteins refer to natural silk proteins and their synthetic analogs having the following three criteria: (1) Amino acid composition of the molecule is dominated by glycine and/or alanine; (2) Consensus crystalline domain is arrayed repeatedly throughout the molecule; (3) the molecule is shear sensitive and can be spun into semicrystalline fiber. Spider silk proteins should also include molecules which are the modified variants of the natural silk proteins and their synthetic analogs defined above.

There are a variety of spider silks, which may be suitable for expression in plants. Many of these are derived from the orb-weaving spiders such as those belonging to the genus *Nephila*. Silks from these spiders may be divided into major ampullate, minor ampullate, and flagelliform silks, each having different physical properties. Those of the major ampullate are the most completely characterized and are often refereed to as spider dragline silk. Natural spider dragline consists of two different proteins that are co-spun from the spider's major ampullate gland.

The present invention provides for various silk and synthetic silk-like proteins in the constructs of the present invention for the expression in the endosperm, leaf or shoot tissue of plants. Of particular interest are the synthetic silks which have as a repeating unit (GPGGYGPGQQ)$_4$GPGGPSGPG-SAAAA (SEQ ID NO:20), (GPGGYGPGQQ)$_4$GPGGPSG-PGSAAAAAAAA (SEQ ID NO:21) (GPGGYGPGQQ)$_4$ GPGGPSGPGSAAAAAAAAAAAAAAAA (SEQ ID NO:22) (GPGGYGPGQQ)$_{16}$GPGGPSGPGSAAAAAAAA (SEQ ID NO:23) (GGYGPGAGQQGPGSQGPGSGGQQG-PGGQ)$_1$ GPYGPSAAAAAAAA (SEQ ID NO:24), (GGYG-PGAGQQGPGSQGPGSGGQQGPGGQ)$_2$ GPYGP-SAAAAAAAA (SEQ ID NO:25), and (GGYGPGAGQQGPGSQGPGSGGQQGPGGQ)$_3$ GPYGP-SAAAAAAAA (SEQ ID NO:26), and recombinant silk protein sequences made up of the fusion proteins: MGHHHHH-HHHHHSSGHIDDDDKHMLEDPP-[(GGAGPGGAGPGGAGPGGAGP)$_1$ (GGPSGPGSAAAAAAAAGP)]$_{20}$-(SEQ ID NO:27), MGH-HHHHHHHHHSSGHIDDDDKHMLEDPP-[(GGAGPG-GAGPGGAGPGGAGP)$_2$ (GGPSGPGSAAAAAAA-AGP)]$_{14}$-(SEQ ID NO:28), MGHHHHHHHHHHSSGHID-DDDKHMLEDPP-[(GGAGPGGAGPGGAGPGGAGP)$_4$ (GGPSGPGSAAAAAAAAGP)]$_8$-(SEQ ID NO:29)-MGH-HHHHHHHHHSSGHIDDDDKHMLEDPP-(GGAGPG-GAGPGGAGPGGAGP)$_{40}$-(SEQ ID NO:30), MGHHHHH-HHHHHSSGHIDDDDKHMLEDPP-[(GGYGPGGSGPGGYGPGGSGP)$_1$ (GGPSGPGSAAAAAAAAGP)]$_{20}$-(SEQ ID NO:31), MGH-HHHHHHHHHSSGHIDDDDKHMLEDPP-[(GGYG-PGGSGPGGYGPGGSGP)$_2$ (GGPSGPG-SAAAAAAAAGP)]$_{14}$-(SEQ ID NO:32), MGHHHHHHHHHHSSGHIDDDDKHMLEDPP-[(GGYGPGGSGPGGYGPGGSGP)$_4$ (GGPSGPG-SAAAAAAAAGP)]$_8$-(SEQ ID NO:33) and MGHHHHHH-HHHHSSGHIDDDDKHMLEDPP-(GGYGPGGSGPGGYGPGGSGP)$_{47}$-(SEQ ID NO:34); RPHMSRPAPAPRPLPEPLPAPRPIPAPL-PRPVPIRPLPAPRGSKL (SEQ ID NO:36) which is duplicated to make proteins up to 350 kDa, RPHMTS-VSQSQQASVSQSQQASVSQSQQASVSQSQQASVSQS-QQSSNAYSQQAS GSKL (SEQ ID NO:38) which is duplicated to make proteins up to 350 kDa, and RPHMSRPAPA-PRPLPEPLPAPRPIPAPLPRPVPIV-SQVQQASIQQAQSSSAQSRQSA VAQQASVSQSQQASVSQSQQAS-VSQSQQASVSQSQQASVSQSQQSSNAYSAASN AASS-VSQASSASSYFNSQVVQSTLSSSLQSS-SALSSIAYGQTSANINDV AAAVARSVSQSLGVSQQAAQSVISQQLA-SAGAGASAQTLAQLISSAVSSLVQQS GTVSAGQEQ-SISQALSSSILSSSLSQVVAQRPLPAPRGSKL (SEQ ID NO:40) which is duplicated to make proteins up to 350 kDa.

Nucleic Acid Molecules

Nucleic acid molecules encoding the polypeptides of the invention may be prepared by two general methods: (1) synthesis from appropriate nucleotide triphosphates, or (2) isolation from biological sources. Both methods utilize protocols well known in the art. The availability of nucleotide sequence information, such as the DNA sequences encoding a natural or synthetic spider silk protein, enables preparation of an isolated nucleic acid molecule of one or more embodiments of the present invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

In accordance with at least one aspect of the present invention, nucleic acids having the appropriate level of sequence homology with sequences encoding a spider silk protein may be identified by using hybridization and washing conditions of appropriate stringency. Such methods are useful for a variety of purposes, including the screening of libraries comprising mutated spider silk-encoding nucleic acid sequences for desired properties. For example, hybridizations may be performed, using a hybridization solution comprising: 5×SSC, 5×Denhardt's reagent, 1.0% SDS, 100 ug/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

The nucleic acid molecules described herein include cDNA, genomic DNA, RNA, and fragments thereof which may be single- or double-stranded. Thus, oligonucleotides are provided having sequences capable of hybridizing with at least one sequence of a nucleic acid sequence, such as selected segments of sequences encoding a spider silk protein. Also contemplated in the scope of the present invention are methods of use for oligonucleotide probes which specifically hybridize with DNA from sequences encoding a spider silk protein under high stringency conditions. Primers capable of specifically amplifying sequences encoding a spider silk protein are also provided. As mentioned previously, such oligonucleotides are useful as primers for detecting, isolating and amplifying sequences encoding a spider silk protein.

Alternatively, standard purification strategies designed to differentially isolate silk protein from plant homogenates may be used to advantage. Purification of a plant-expressed spider silk protein may be facilitated by its extreme stability under conditions that denature typical proteins, such as, for example, high heat and low pH. Accordingly, general protein purification strategies may be adapted to optimize silk purification from leaves. Above-ground portions of transgenic plants may be harvested and allowed to air dry as per normal production practices. The plant material may be homogenized in an appropriate buffer followed by various treatments designed to differentially eliminate contaminants. Silk protein recovery may be optimized following treatments in which plant extracts are subject to any one or a combination of the following: 1) boiling in the presence or absence of detergent; 2) differential centrifugation; 3) progressively decreasing the pH; and 4) precipitation with varying concentrations of urea or ammonium sulfate. One of ordinary skill in the art may vary the above treatments to optimize the yield and efficiency of purification of spider silk proteins from plants.

The quantity of silk protein may be determined by immunoblotting and the purity and concentration assessed definitively by amino acid analysis. Purified silk protein may be analyzed for mechanical properties as previously described to ensure that the recombinant protein possesses the desired properties.

A protein produced according to the present invention may be chemically modified after synthesis of the polypeptide. The presence of several carboxylic acid side chains (Asp or Glu) in the spacer regions facilitates the attachment of a variety of different chemical groups to silk proteins including amino acids having such side chains. The simplest and easiest procedure is to use a water-soluble carbodiimide to attach the modifying group via a primary amine. If the group to be attached has no primary amine, a variety of linking agents can be attached via their own primary amines and the modifying group attached via an available chemistry.

Where appropriate, the DNA of interest may be optimized for increased expression in the transformed plant. That is, the coding sequences can be synthesized using plant-preferred codons for improved expression. Methods are available and known to those skilled in the art for synthesizing plant-preferred genes.

Exemplary Methods for Generation of Spider Silk Proteins

In view of the unique properties of spider silk proteins, special considerations should be applied to the generation of synthetic spider silk proteins. The repetitive nature of amino acid sequences encoding these proteins may render synthesis of a full length spider silk protein, or fragments thereof, technically challenging. To facilitate production of full length silk protein molecules, the following protocol is provided.

The polypeptides of the present invention can be made by direct synthesis or by expression from cloned DNA. Means for expressing cloned DNA are set forth above and are generally known in the art. The following considerations are recommended for the design of expression vectors used to express DNA encoding spider silk proteins.

First, since spider silk proteins are highly repetitive in structure, cloned DNA should be propagated and expressed in host cell strains that can maintain repetitive sequences in extrachromosomal elements (e.g., SURE™ cells, Stratagene). The prevalence of specific amino acids (e.g., alanine, glycine, proline, and glutamine) also suggests that it might be advantageous to use a host cell that over-expresses tRNA for these amino acids or in which these specific tRNAs are known to be in high abundance.

Method for use of Fluorescent Protein (FP) in Corn

The discovery and use of fluorescent proteins, as used herein are also known as sortable markers, such as the green fluorescent protein (GFP) (SEQ ID NO:17), has revolutionized the way protein localization is performed. Fluorescent protein (FP) fusions allow analysis of dynamic localization patterns in real time. Over the last several years, a number of different colored fluorescent proteins have been developed and may be used in various constructs of the present invention, including yellow FP(YFP) (SEQ ID NO:19), cyan FP(CFP) (SEQ ID NO:15), red FP (mRFP) (SEQ ID NO:13), the maize specific cerulean FP (mCeFP) (SEQ ID NO:53), the mCherry maize specific FP (mChRFP) (SEQ ID NO:51), the maize specific blue FP, TagBFP, (mBFP) (SEQ ID NO:49), the maize specific teal FP (mTFP) (SEQ ID NO: 47) and others. Some of these proteins have improved spectral properties, allowing analysis of fusion proteins for a longer period of time and permitting their use in photobleaching experiments. Others are less sensitive to pH, and other physiological parameters, making them more suitable for use in a variety of cellular contexts. Additionally, FP-tagged proteins can be used in protein—protein interaction studies by bioluminescence resonance energy transfer (BRET) or fluorescence resonance energy transfer (FRET). High-throughput analyses of FP fusion proteins in *Arabidopsis* have been performed by overexpressing cDNA-GFP fusions driven by strong constitutive promoters. Although useful, this approach has inherent limitations, as it does not report tissue-specificity, and overexpression of multimeric proteins may disrupt the complex. Furthermore, overexpression can lead to protein aggregation and/or mislocalization.

In order to tag a specific gene with a fluorescent protein such as the red fluorescent protein (mRFP), usually a gene ideal for tagging has been identified through forward genetic analysis or by homology to an interesting gene from another model system. For generation of native expression constructs, full-length genomic sequence is required. For tagging of the full-length gene with an FP, the full-length gene sequence should be available, including all intron and exon sequences. A standard protocol is to insert the mRFP tag or marker at a default position of ten amino acids upstream of the stop codon, following methods known in the art established for *Arabidopsis*. The rationale is to avoid masking C-terminal targeting signals (such as endoplasmic reticulum (ER) retention or peroxisomal signals). In addition, by avoiding the N-terminus, disruption of N-terminal targeting sequences or transit peptides is avoided. However, choice of tag insertion is case-dependent, and it should be based on information on functional domains from database searches. If a homolog of the gene of interest has been successfully tagged in another organism, this information is also used to choose the optimal tag insertion site. A set of four primers is designed for amplification of the target locus. Primers P1 and P2 amplify the 5' regulatory regions and partial coding region, extending to the position where the mRFP tag will be inserted. The P3 and P4 primers are used to amplify the remainder of the gene from the tag insertion site and including the 3' regulatory regions. Maize genomic DNA is used for amplification of P1 to P2 and P3 to P4 fragments. However, in cases where amplification from genomic DNA fails, maize BAC DNA clones, if available can be used as the PCR template. Primer design software PRIMER3 is used for design of the P1-P4 primers. In general, the primer T m should be 60-62° C., but is dependent on primer requirements. The P1 and P4 primers have linkers overlapping with the Gateway™ ttPCR primers in addition to the gene-specific sequences to allow cloning of the PCR product in Gateway™ compatible vectors. Similarly the primers P2 and P3 contain gene specific sequences as well as linkers that are complementary to sequences from the mRFP clones to allow incorporation of the mRFP tag into the ttPCR product.

A cleavable linker peptide may be placed between proteins such that they can be cleaved and the desired protein obtained. Transcription Terminator The transcription termination region of the constructs of the present invention is a downstream regulatory region including the stop codon (TGA, TAG or TAA) and the transcription terminator sequence (SEQ ID NO:5). Alternative transcription termination regions which maybe used may be native with the transcriptional initiation region, may be native with the DNA sequence of interest, or may be derived from another source. The transcription termination region may be naturally occurring, or wholly or partially synthetic. Convenient transcription termination regions are available from the Ti-plasmid of *A. tumefaciens*, such as the octopine synthase and nopaline synthase transcription termination regions or from the genes for beta-phaseolin, the chemically inducible plant gene, pIN.

Percent Similarity and Percent Identity

Percent identity refers to the comparison of the homozygous alleles of two plant varieties. Percent identity is determined by comparing a statistically significant number of the homozygous alleles of two developed varieties. For example, a percent identity of 90% between plant variety 1 and plant variety 2 means that the two varieties have the same allele at 90% of their loci. Percent identity as used herein with respect to two nucleic acids refers to the comparison of the entire sequence for each of the two nucleic acids and is determined by GAP alignment using default parameters (GCG, GAP version 10, Accelrys, San Diego, Calif.). GAP uses the algorithm of Needleman and Wunsch to find the alignment of two complete sequences that maximizes the number of matches and minimizes the number of sequence gaps. Sequences which have 100% identity are identical. The present invention encompasses nucleic acids that have about 70%, 75%, 80%, 85%, 90%, 91%, 92%, 93%, 94%, 95%, 96%, 97%, 98%, 99%, or 100% sequence identity to the specified nucleic acid.

Percent similarity refers to the comparison of the homozygous alleles of one plant variety with those of another plant, and if the homozygous allele of the first plant matches at least one of the alleles from the other plant then they are scored as similar. Percent similarity is determined by comparing a statistically significant number of loci and recording the number of loci with similar alleles as a percentage. A percent similarity of 90% between the first plant and a second plant means that the first matches at least one of the alleles of the second plant at 90% of the loci.

The practice of the present invention employs, unless otherwise indicated, conventional techniques of chemistry, molecular biology, microbiology, recombinant DNA, genetics, immunology, cell biology, cell culture and transgenic biology, which are within the skill of the art.

Examples of Applications for the Expression of Spider Silk

The following examples are provided to illustrate further the various applications of the present invention and are not intended to limit the invention beyond the limitations set forth in the appended claims.

Example 1

Synthetic Spider Silk Protein Coding Sequence $E_{454}$ of a *Nephila Clavipes* MaSp 2 Construct in Corn In at least one embodiment of the present invention a corn shoot tissue-specific regulation region encoding a DNA construct is provided, represented as CeUrr-SS, comprising a tissue promoter (SEQ ID NO:3) operably linked to a synthetic spider silk protein coding sequence (SEQ ID NO:20). PCR is conducted using four primers (SEQ ID NO:8; SEQ ID NO:9; SEQ ID NO:10; and SEQ ID NO:11). The gene primers permit amplification of the entire regulatory region, and gene sequence. The DNeasy® Plant Mini genomic DNA isolation kit (QIAGEN) is used for maize genomic DNA isolation, following manufacturer's instructions. Any method that produces high molecular weight genomic DNA is appropriate. Genomic DNA is eluted with TE buffer and used directly for subsequent PCR reactions. KOD Hot Start DNA polymerase (Novagen), a "proofreading" enzyme, is used for amplification of the maize genomic fragments. The product from the PCR is then cloned using the Gateway® system into a donor vector (available from Invitrogen).

Regardless of the cloning procedure, the final construct is then transferred by electroporation into binary destination vectors such as an *Agrobacterium* plasmid or Ti plasmid and ultimately transformed into maize. Binary plasmids are transferred to *Agrobacterium* (e.g., EHA101 strain) by electroporation. After electroporation, 800 µL of LB medium are added to the tubes and incubated at 28° C. for 2 h with shaking Aliquots of 50 µL and 200 µL are plated on LB plates containing spectinomycin (100 mg/L), kanamycin (50 mg/L), and chloramphenicol (25 mg/L) and incubated for 2-3 days at 28° C. Spectinomycin is used for selecting the binary plasmid, whereas the other two antibiotics are for the selection of the EHA101 *Agrobacterium* strain. Single colonies are picked and grown for 2 to 3 days in 6 mL LB medium supplemented with above antibiotics with shaking at 28° C. To verify the clones, the plasmids are isolated from these cultures by a modified alkaline lysis method and checked by restriction enzyme digestion or PCR. Following clone verification, the constructs are transformed into maize to generate stable lines. Transgenic maize plants expressing the synthetic spider silk protein genes are generated. Maize transformants are provided as seedlings on sterile Petri plates, regenerated from callus tissue from Hill lines (classified here as $T_0$ generation). The plants are transferred from plates to growth chambers maintained at 25-28° C. (16-h light period) until the roots and shoots are several centimeters long. Once acclimated in the growth chamber, the first generation seedlings are screened for expression. The seedlings are transferred to soil in small pots and covered with a plastic dome to maintain humidity for 3-4 days and encourage optimal root growth. The established seedlings are then transferred to larger pots for growth and pollination in the greenhouse. To maintain adequate growth, greenhouse conditions are optimized for maize.

Example 2

Synthetic Spider Silk Protein Coding Sequence $E_{454}$ of a *Nephila Clavipes* MaSp 2 Construct in Corn In at least one embodiment of the present invention a corn endosperm tissue regulation region encoding a DNA construct is provided, represented as CeUrr-SS, comprising a tissue promoter encoded with a leader sequence (SEQ ID NO:1) operably linked to a synthetic spider silk protein coding sequence (SEQ ID NO:20). PCR is conducted using four primers (SEQ ID NO:8; SEQ ID NO:9; SEQ ID NO:10; and SEQ ID NO:11). The gene specific primers permit amplification of the entire regulatory region, gene sequence. The DNeasy® Plant Mini genomic DNA isolation kit (QIAGEN) is used for maize genomic DNA isolation, following manufacturer's instructions. Any method that produces high molecular weight genomic DNA is appropriate. Genomic DNA is eluted with TE buffer and used directly for subsequent PCR reactions. KOD Hot Start DNA polymerase (Novagen), a "proofreading" enzyme, is used for amplification of the maize genomic fragments. The product from the PCR is then cloned using the Gateway® system into a donor vector (available from Invitrogen).

Regardless of the cloning procedure, the final construct is then transferred by electroporation into binary destination vectors such as an *Agrobacterium* plasmid or Ti plasmid and ultimately transformed into maize. Binary plasmids are transferred to *Agrobacterium* (e.g., EHA101 strain) by electroporation. Binary plasmids are transferred to *Agrobacterium* (e.g., EHA101 strain) by electroporation. After electroporation, 800 µL of LB medium are added to the tubes and incubated at 28° C. for 2 h with shaking Aliquots of 50 µL and 200 µL are plated on LB plates containing spectinomycin (100 mg/L), kanamycin (50 mg/L), and chloramphenicol (25 mg/L) and incubated for 2-3 days at 28° C. Spectinomycin is used for selecting the binary plasmid, whereas the other two antibiotics are for the selection of the EHA101 *Agrobacterium* strain. Single colonies are picked and grown for 2 to 3 days in 6 mL LB medium supplemented with above antibiotics with shaking at 28° C. To verify the clones, the plasmids are isolated from these cultures by a modified alkaline lysis method and checked by restriction enzyme digestion or PCR. Following clone verification, the constructs are transformed into maize to generate stable lines. Transgenic maize plants expressing the synthetic spider silk protein genes are generated. Maize transformants are provided as seedlings on sterile Petri plates, regenerated from callus tissue from Hill lines (classified here as $T_0$ generation). The plants are transferred from plates to growth chambers maintained at 25-28° C. (16-h light period) until the roots and shoots are several centimeters long. Once acclimated in the growth chamber, the first generation seedlings are screened for expression. The seedlings are transferred to soil in small pots and covered with a plastic dome to maintain humidity for 3-4 days and encourage optimal root growth. The established seedlings are then transferred to larger pots for growth and pollination in the greenhouse. To maintain adequate growth, greenhouse conditions are optimized for maize.

Example 3

Synthetic Spider Silk Protein Coding Sequence $E_{454}$ of a *Nephila Clavipes* MaSp 2 Construct in Corn with a Terminator Sequence In at least one embodiment of the present invention a corn endosperm tissue regulation region encoding a DNA construct is provided, represented as CeUrr-SS-X, comprising a promoter (SEQ ID NO:3) operably linked to a synthetic spider silk protein coding sequence (SEQ ID NO:20) which is operably linked to a transcription terminator sequence (SEQ ID NO:5). A PCR is conducted using four primers (SEQ ID NO:8; SEQ ID NO:9; SEQ ID NO:10; and SEQ ID NO:11). The gene specific primers permit amplification of the entire regulatory region, gene sequence. The DNeasy® Plant Mini genomic DNA isolation kit (QIAGEN) is used for maize genomic DNA isolation, following manufacturer's instructions. Any method that produces high molecular weight genomic DNA is appropriate. Genomic DNA is eluted with TE buffer and used directly for subsequent PCR reactions. KOD Hot Start DNA polymerase (Novagen), a "proofreading" enzyme, is used for amplification of the maize genomic fragments. The product from the PCR is then cloned using the Gateway® system into a donor vector (available from Invitrogen).

Regardless of the cloning procedure, the final construct is then transferred by electroporation into binary destination vectors such as an *Agrobacterium* plasmid or Ti plasmid and ultimately transformed into maize. Binary plasmids are transferred to *Agrobacterium* (e.g., EHA101 strain) by electroporation. After electroporation, 800 µL of LB medium are added to the tubes and incubated at 28° C. for 2 h with shaking Aliquots of 50 µL and 200 µL are plated on LB plates containing spectinomycin (100 mg/L), kanamycin (50 mg/L), and chloramphenicol (25 mg/L) and incubated for 2-3 days at 28° C. Spectinomycin is used for selecting the binary plasmid, whereas the other two antibiotics are for the selection of the EHA101 *Agrobacterium* strain. Single colonies are picked and grown for 2 to 3 days in 6 mL LB medium supplemented with above antibiotics with shaking at 28° C. To verify the clones, the plasmids are isolated from these cultures by a modified alkaline lysis method and checked by restriction enzyme digestion or PCR. Following clone verification, the constructs are transformed into maize to generate stable lines. Transgenic maize plants expressing the synthetic spider silk protein genes are generated. Maize transformants are provided as seedlings on sterile Petri plates, regenerated from callus tissue from Hill lines (classified here as $T_0$ generation). The plants are transferred from plates to growth chambers maintained at 25-28° C. (16-h light period) until the roots and shoots are several centimeters long. Once acclimated in the growth chamber, the first generation seedlings are screened for expression. The seedlings are transferred to soil in small pots and covered with a plastic dome to maintain humidity for 3-4 days and encourage optimal root growth. The established seedlings are then transferred to larger pots

Example 4

Synthetic Spider Silk Protein Coding Sequence $E_{454}$ of a *Nephila Clavipes* MaSp 2 Construct in Corn Using the Multisite Gateway® Cloning Procedure In at least one embodiment of the present invention a corn endosperm tissue regulation region encoding a DNA construct is provided, represented as CeUrr-SS-X, comprising a promoter (SEQ ID NO:3) operably linked to a synthetic spider silk protein coding sequence (SEQ ID NO:20) which is operably linked to a transcription terminator sequence (SEQ ID NO:5). Using the Multisite Gateway® cloning procedure, available from PCR products with Gateway® entry sites and corresponding to the 5'UTR plus gene ORF (for C-terminal tagging) and 3'UTR plus gene ORF (for N-terminal tagging), are cloned into pDONR vectors using the Gateway® BP reaction system. An expression clone is generated by combining entry clones, including a fluorescent tag entry vector, along with the pTF101.1 maize binary vector that has been converted into a 3-way Gateway® destination vector.

Regardless of the cloning procedure, the final construct is then transferred by electroporation into binary destination vectors such as an *Agrobacterium* plasmid or Ti plasmid and ultimately transformed into maize. Binary plasmids are transferred to *Agrobacterium* (e.g., EHA101 strain) by electroporation. After electroporation, 800 µL of LB medium are added to the tubes and incubated at 28° C. for 2 h with shaking Aliquots of 50 µL and 200 µL are plated on LB plates containing spectinomycin (100 mg/L), kanamycin (50 mg/L), and chloramphenicol (25 mg/L) and incubated for 2-3 days at 28° C. Spectinomycin is used for selecting the binary plasmid, whereas the other two antibiotics are for the selection of the EHA101 *Agrobacterium* strain. Single colonies are picked and grown for 2 to 3 days in 6 mL LB medium supplemented with above antibiotics with shaking at 28° C. To verify the clones, the plasmids are isolated from these cultures by a modified alkaline lysis method and checked by restriction enzyme digestion or PCR. Following clone verification, the constructs are transformed into maize to generate stable lines. Transgenic maize plants expressing the synthetic spider silk protein genes are generated. Maize transformants are provided as seedlings on sterile Petri plates, regenerated from callus tissue from Hill lines (classified here as $T_0$ generation). The plants are transferred from plates to growth chambers maintained at 25-28° C. (16-h light period) until the roots and shoots are several centimeters long. Once acclimated in the growth chamber, the first generation seedlings are screened for expression. The seedlings are transferred to soil in small pots and covered with a plastic dome to maintain humidity for 3-4 days and encourage optimal root growth. The established seedlings are then transferred to larger pots for growth and pollination in the greenhouse. To maintain adequate growth, greenhouse conditions are optimized for maize.

Example 5

Identification of Synthetic Spider Silk Protein Coding Sequence Using a Red Fluorescent Protein In at least one embodiment of the present invention provides a corn endosperm tissue regulation region encoding a DNA construct, represented as CeUrr-SS-FP-X, comprising a promoter (SEQ ID NO:3) operably linked to a synthetic spider silk protein coding sequence (SEQ ID NO:20), operably linked to a fluorescent protein coding sequence (SEQ ID NO:13) which is operably linked to a transcription terminator sequence (SEQ ID NO:5). A PCR is conducted using four primers (SEQ ID NO:8; SEQ ID NO:9; SEQ ID NO:10; and SEQ ID NO:11). The gene specific primers permit amplification of the entire regulatory region, gene sequence. The DNeasy® Plant Mini genomic DNA isolation kit (QIAGEN) is used for maize genomic DNA isolation, following manufacturer's instructions. Any method that produces high molecular weight genomic DNA is appropriate. Genomic DNA is eluted with TE buffer and used directly for subsequent PCR reactions. KOD Hot Start DNA polymerase (Novagen), a "proofreading" enzyme, is used for amplification of the maize genomic fragments. The product from the PCR is then cloned using the Gateway® system into a donor vector (available from Invitrogen).

For gene tagging, mRFP1 (SEQ ID NO:13) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. mRFP1 clones are generated with these linkers. The fluorescent protein tag fragments are PCR amplified from the above plasmids using the following primers of SEQ ID NO:41 and SEQ ID NO:42.

Regardless of the cloning procedure, the final construct is then transferred by electroporation into binary destination vectors such as an *Agrobacterium* plasmid or Ti plasmid and ultimately transformed into maize. Binary plasmids are transferred to *Agrobacterium* (e.g., EHA101 strain) by electroporation. After electroporation, 800 µL of LB medium are added to the tubes and incubated at 28° C. for 2 h with shaking Aliquots of 50 µL and 200 µL are plated on LB plates containing spectinomycin (100 mg/L), kanamycin (50 mg/L), and chloramphenicol (25 mg/L) and incubated for 2-3 days at 28° C. Spectinomycin is used for selecting the binary plasmid, whereas the other two antibiotics are for the selection of the EHA101 *Agrobacterium* strain. Single colonies are picked and grown for 2 to 3 days in 6 mL LB medium supplemented with above antibiotics with shaking at 28° C. To verify the clones, the plasmids are isolated from these cultures by a modified alkaline lysis method and checked by restriction enzyme digestion or PCR. Following clone verification, the constructs are transformed into maize to generate stable lines. Transgenic maize plants expressing the FP tagged genes are generated. Maize transformants are provided as seedlings on sterile Petri plates, regenerated from callus tissue from Hill lines (classified here as $T_0$ generation). The plants are transferred from plates to growth chambers maintained at 25-28° C. (16-h light period) until the roots and shoots are several centimeters long. Once acclimated in the growth chamber, the first generation seedlings are screened for expression. The seedlings are transferred to soil in small pots and covered with a plastic dome to maintain humidity for 3-4 days and encourage optimal root growth. The established seedlings are then transferred to larger pots for growth and pollination in the greenhouse. To maintain adequate growth, greenhouse conditions are optimized for maize.

The mRFP will produce a red fluorescence in the presence of UV light, thereby allowing for the monitoring of the synthetic spider silk protein activity and the presence or absence of the tagged protein in a targeted region. The expression of the spider silk is localized to corn kernel endosperm and will emit a red fluorescence in the presence of UV light. Sunlight is sufficient to excite the fluorescence so that the kernels containing the transgene appear pink. The mRFP will eventually be denatured during use or treatment of the silk and so the silk would likely lose the pink color.

Example 6

Synthetic Spider Silk Protein Coding Sequence $E_4S_8$ in Corn Identified Using a Cyan Fluorescent Protein Example five is repeated with the exception for gene tagging, CFP (SEQ ID NO:15) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. CFP clones are generated with these linkers. The fluorescent protein tag fragments are PCR amplified from the above plasmids using the following primers of SEQ ID NO:43 and SEQ ID NO:44.

Example 7

Synthetic Spider Silk Protein Coding Sequence $E_4S_{16}$ in Corn Identified with a Yellow Fluorescent Protein Example five is repeated with the exception of gene tagging. YFP (SEQ ID NO:19) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. YFP clones are generated with these linkers. The fluorescent protein tag fragments are PCR amplified from the above plasmids using the following primers of SEQ ID NO:43 and SEQ ID NO:44.

Example 8

Identification of Synthetic Spider Silk Protein Coding Sequence Using a Maize Specific Fluorescent Protein Example five is repeated with the exception for gene tagging. Cerulean FP (SEQ ID NO:52) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. Cerulean clones are generated with these linkers. The fluorescent protein tag fragments are PCR amplified from the above plasmids using the following primers of SEQ ID NO:59 and SEQ ID NO:60.

Example 9

Identification of Synthetic Spider Silk Protein Coding Sequence Using a Maize Specific Cherry Fluorescent Protein Example five is repeated with the exception for gene tagging. Maize specific cherry (SEQ ID NO:51) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. mCHERRY clones are generated with these linkers. The fluorescent protein tag fragments are PCR amplified from the above sequences using the following primers of SEQ ID NO:57 and SEQ ID NO:58.

Example 10

Identification of Synthetic Spider Silk Protein Coding Sequence Using a Maize Specific Blue Fluorescent Protein Example five is repeated with the exception of for gene tagging. Maize specific blue fluorescent protein (SEQ ID NO:48) or (SEQ ID NO:49) tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. The maize specific blue FP clones are generated with these linkers. The fluorescent protein tag fragments are PCR amplified from the above sequences using the following primers of SEQ ID NO:57 and SEQ ID NO:58.

Example 11

Identification of Synthetic Spider Silk Protein Coding Sequence Using a Maize Specific Teal Fluorescent Protein Example five is repeated with the exception for gene tagging. The maize teal FP (SEQ ID NO:47) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. Teal clones are generated with these linkers. The fluorescent protein tag fragments are PCR amplified from the above plasmids using the following primers of SEQ ID NO:57 and SEQ ID NO:58

Example 12

Identification of Synthetic Spider Silk Protein Coding Sequence in Corn Shoot Tissue Using a Red Fluorescent Protein In at least one embodiment of the present invention provides a corn shoot tissue regulation region encoding a DNA construct, represented as PsUrr-SS-FP-X comprising a corn shoot tissue promoter (SEQ ID NO:62) operably linked to a synthetic spider silk protein coding sequence (SEQ ID NO:20), operably linked to a fluorescent protein coding sequence (SEQ ID NO:13) and operably linked to a transcription terminator sequence. A PCR is conducted using two primers (SEQ ID NO:63 and SEQ ID NO:64). The gene specific primers permit amplification of the entire regulatory region, gene sequence. The DNeasy® Plant Mini genomic DNA isolation kit (QIAGEN) is used for maize genomic DNA isolation, following manufacturer's instructions. Any method that produces high molecular weight genomic DNA is appropriate. Genomic DNA is eluted with TE buffer and used directly for subsequent PCR reactions. KOD Hot Start DNA polymerase (Novagen), a "proofreading" enzyme, is used for amplification of the maize genomic fragments. The product from the PCR is then cloned using the Gateway® system into a donor vector.

For gene tagging, mRFP1 (SEQ ID NO:13) fluorescent protein tags are modified to remove start and stop codons and add flexible linker peptides flanking the ends, allowing them to be used as either C- or N-terminal fusions, or as internal fusions. These flexible linkers help to minimize folding interference between the target protein and the fluorescent protein. In addition, the linker peptide sequences contain an FseI site at the 5' end and a SfiI site at the 3' end. These restriction enzyme sites can be used to replace one fluorescent protein tag with another, or for addition of others, such as affinity purification tags for proteomics. mRFP1 clones are generated with these linkers. The fluorescent protein tag fragments are PCR amplified from the above plasmids using the following primers of SEQ ID NO:41 and SEQ ID NO:42.

Regardless of the cloning procedure, the final construct is then transferred by electroporation into binary destination vectors such as an *Agrobacterium* plasmid or Ti plasmid and ultimately transformed into maize. Binary plasmids are transferred to *Agrobacterium* (e.g., EHA101 strain) by electroporation. After electroporation, 800 µL of LB medium are added to the tubes and incubated at 28° C. for 2 h with shaking Aliquots of 50 µL and 200 µL are plated on LB plates containing spectinomycin (100 mg/L), kanamycin (50 mg/L), and chloramphenicol (25 mg/L) and incubated for 2-3 days at 28° C. Spectinomycin is used for selecting the binary plasmid, whereas the other two antibiotics are for the selection of the EHA101 *Agrobacterium* strain. Single colonies are picked and grown for 2 to 3 days in 6 mL LB medium supplemented with above antibiotics with shaking at 28° C. To verify the clones, the plasmids are isolated from these cultures by a modified alkaline lysis method and checked by restriction enzyme digestion or PCR. Following clone verification, the constructs are transformed into maize to generate stable lines. Transgenic maize plants expressing the FP tagged genes are generated. Maize transformants are provided as seedlings on sterile Petri plates, regenerated from callus tissue from Hill lines (classified here as $T_0$ generation). The plants are transferred from plates to growth chambers maintained at 25-28° C. (16-h light period) until the roots and shoots are several centimeters long. Once acclimated in the growth chamber, the first generation seedlings are screened for expression. The seedlings are transferred to soil in small pots and covered with a plastic dome to maintain humidity for 3-4 days and encourage optimal root growth. The established seedlings are then transferred to larger pots for growth and pollination in the greenhouse. To maintain adequate growth, greenhouse conditions are optimized for maize.

The mRFP will produce a red fluorescence in the presence of UV light, thereby allowing for the monitoring of the synthetic spider silk protein activity and the presence or absence of the tagged protein in a targeted region. The expression of the spider silk is localized to corn shoots and will emit a red fluorescence in the presence of UV light. Sunlight is sufficient to excite the fluorescence so that the shoots containing the transgene appear pink. The mRFP will eventually be denatured during use or treatment of the silk and so the silk would likely lose the pink color.

Example 13

Identification of Synthetic Spider Silk Protein Coding Sequence in Corn Shoot Tissue Using a Red Fluorescent Protein Example thirteen is repeated with the exception of a corn shoot tissue regulation region encoding a DNA construct represented as PsUrr-SS-FP-X which includes a corn shoot promoter (SEQ ID NO:61) operably linked to a synthetic spider silk protein coding sequence (SEQ ID NO:20) and operably linked to a transcription terminator sequence. A PCR is conducted using two primers (SEQ ID NO:63 and SEQ ID NO:64).

Example 14

Identification of Synthetic Spider Silk Protein Coding Sequence in Corn Shoot Tissue Using a Red Fluorescent Protein Example thirteen is repeated with the exception of a corn shoot tissue regulation region encoding a DNA construct represented as PsUrr-SS-FP-X which includes a corn shoot promoter (SEQ ID NO:62) operably linked to a synthetic spider silk protein coding sequence (SEQ ID NO:20) operably linked to a fluorescent protein coding sequence (SEQ ID NO:13) and operably linked to a transcription terminator sequence. A PCR is conducted using two primers (SEQ ID NO:63 and SEQ ID NO:64.

Example 15

Synthetic Spider Silk Protein Coding Sequence $E_{16}S_8$ of a *Nephila Clavipes* MaSp 2 Construct in Corn Example two is repeated with the exception of a corn endosperm tissue regulation region encoding a DNA construct represented as CeUrr-SS-FP-X which includes a promoter (SEQ ID NO:3) operably linked to a synthetic spider silk protein coding sequence, $E_{16}S_8$ (SEQ ID NO.23) operably linked to a fluorescent protein coding sequence (SEQ ID NO:13) which is operably linked to transcription terminator sequence (SEQ ID NO:4).

Example 16

Spider Silk Protein Coding Sequence $E_1S_8$ of an *Argiope* Sp. MaSp 2 Construct in Corn Example two is repeated with the exception of a corn endosperm tissue regulation region encoding a DNA construct represented as CeUrr-SS-FP-X which includes a promoter (SEQ ID NO:3) operably linked to a synthetic spider silk protein coding sequence, $E_1S_8$ (SEQ ID NO:24), operably linked to a fluorescent protein coding sequence (SEQ ID NO:13) which is operably linked to a transcription terminator sequence (SEQ ID NO:5).

Example 17

Synthetic Spider Silk Protein Coding Sequence $E_2S_8$ of an *Argiope* Sp. MaSp 2 Construct in Corn Example two is repeated with the exception of a corn endosperm tissue regulation region encoding a DNA construct represented as CeUrr-SS-FP-X which includes a promoter (SEQ ID NO:3) operably linked to a synthetic spider silk protein coding sequence, $E_2S_8$ (SEQ ID NO:25), operably linked to a fluorescent protein coding sequence (SEQ ID NO:13) which is operably linked to a transcription terminator sequence (SEQ ID NO:5).

Example 18

Synthetic Spider Silk Protein Coding Sequence $E_3S_8$ of an *Argiope* Sp. MaSp 2 Construct in Corn Example two is repeated with the exception of a corn endosperm tissue regulation region encoding a DNA construct represented as CeUrr-SS-FP-X which includes a promoter (SEQ ID NO:3) operably linked to a synthetic spider silk protein coding sequence, $E_3S_8$ (SEQ ID NO:26), operably linked to a fluorescent protein coding sequence (SEQ ID NO:13) which is operably linked to a transcription terminator sequence (SEQ ID NO:5).

Example 19

Synthetic Spider Silk Protein Coding Sequence $A1S8_{20}$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, $A1S8_{20}$ (SEQ ID NO:27), operably linked to a fluorescent protein coding sequence (SEQ ID NO:13) which is operably linked to a transcription terminator sequence (SEQ ID NO:5).

Example 20

Synthetic Spider Silk Protein Coding Sequence $A1S8_{14}$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, $A1S8_{14}$ (SEQ ID NO:28), operably linked to a fluorescent protein coding sequence (SEQ ID NO:13) which is operably linked to a transcription terminator sequence (SEQ ID NO:5).

Example 21

Synthetic Spider Silk Protein Coding Sequence $A1S8_8$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, $A1S8_8$ (SEQ ID NO:29), operably linked to a fluorescent protein coding sequence (SEQ ID NO:13) which is operably linked to a transcription terminator sequence (SEQ ID NO:5).

Example 22

Synthetic Spider Silk Protein Coding Sequence $A_{40}$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, $A_{40}$ (SEQ ID NO:30), operably linked to a fluorescent protein coding sequence (SEQ ID NO:13) which is operably linked to a transcription terminator sequence (SEQ ID NO:5).

Example 23

Synthetic Spider Silk Protein Coding Sequence $Y1S8_{20}$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, $Y1S8_{20}$ (SEQ ID NO:31), operably linked to a fluorescent protein coding sequence (SEQ ID NO:13) which is operably linked to a transcription terminator sequence (SEQ ID NO:5).

Example 24

Synthetic Spider Silk Protein Coding Sequence $Y1S8_{14}$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, $Y1S8_{14}$ (SEQ ID NO:32), operably linked to a fluorescent protein coding sequence (SEQ ID NO:13) which is operably linked to a transcription terminator sequence (SEQ ID NO:5).

Example 25

Synthetic Spider Silk Protein Coding Sequence $Y1S8_8$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, Y1S8$_8$ (SEQ ID NO:33), operably linked to a fluorescent protein coding sequence (SEQ ID NO:13) which is operably linked to a transcription terminator sequence (SEQ ID NO:5).

Example 26

Synthetic Spider Silk Protein Coding Sequence Y$_{47}$ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, Y$_{47}$ (SEQ ID NO:34), operably linked to a fluorescent protein coding sequence (SEQ ID NO:13) which is operably linked to a transcription terminator sequence (SEQ ID NO:5).

Example 27

Synthetic Spider Silk Protein Coding Sequence PXP Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, PXP (SEQ ID NO:35), operably linked to a fluorescent protein coding sequence (SEQ ID NO:13) which is operably linked to a transcription terminator sequence (SEQ ID NO:5). The PXP sequence is a repeat sequence which is duplicated to make proteins up to 350 kDa.

Example 28

Synthetic Spider Silk Coding Sequence PXP in Corn

Example two is repeated with the exception of a corn endosperm tissue regulation region encoding a DNA construct represented as CeUrr-SS-FP-X including a promoter (SEQ ID NO:3) operably linked to a synthetic spider silk nucleic acid coding sequence, PXP (SEQ ID NO:36), operably linked to a fluorescent protein coding sequence (SEQ ID NO:13) which is operably linked to a transcription terminator sequence (SEQ ID NO:5). The PXP sequence is a repeat sequence which is duplicated to make proteins up to 350 kDa.

Example 29

Synthetic Spider Silk Protein Coding Sequence QQ in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding sequence, QQ (SEQ ID NO:37), operably linked to a fluorescent protein coding sequence (SEQ ID NO:13) which is operably linked to a transcription terminator sequence (SEQ ID NO:5). The QQ sequence is a repeat sequence which is duplicated to make proteins up to 350 kDa.

Example 30

Synthetic Spider Silk Coding Sequence QQ in Corn

Example two is repeated with the exception of a corn endosperm tissue regulation region encoding a DNA construct represented as CeUrr-SS-FP-X including a promoter (SEQ ID NO:3) operably linked to a synthetic spider silk nucleic acid coding sequence, QQ (SEQ ID NO:38), operably linked to a fluorescent protein coding sequence (SEQ ID NO:13) which is operably linked to a transcription terminator sequence (SEQ ID NO:5). The QQ sequence is a repeat sequence which is duplicated to make proteins up to 350 kDa.

Example 31

Synthetic Spider Silk Protein Coding the Full Piriform Sequence in Corn

Example two is repeated with the exception of a corn endosperm tissue regulation region encoding a DNA construct represented as CeUrr-SS-FP-X including a promoter (SEQ ID NO:3) operably linked to a synthetic spider silk protein coding full piriform sequence (SEQ ID NO:39), operably linked to a fluorescent protein coding sequence (SEQ ID NO:13) which is operably linked to a transcription terminator sequence (SEQ ID NO:5). The full piriform sequence is a repeat sequence which is duplicated to make proteins up to 350 kDa.

Example 32

Synthetic Spider Silk Coding Sequence the Full Piriform Sequence in Corn

Example two is repeated with the exception of a corn endosperm tissue regulation region encoding a DNA construct represented as CeUrr-SS-FP-X including a promoter (SEQ ID NO:3) operably linked to a synthetic spider silk nucleic acid coding full piriform sequence (SEQ ID NO:40), operably linked to a fluorescent protein coding sequence (SEQ ID NO:13) which is operably linked to a transcription terminator sequence (SEQ ID NO:5). The full piriform sequence is a repeat sequence which is duplicated to make proteins up to 350 kDa.

Example 33

Synthetic Spider Silk Coding Protein Sequence in Corn

Example two is repeated with the exception of a corn endosperm tissue regulation region encoding a DNA construct represented as CeUrr-SS-FP-X including a promoter (SEQ ID NO:2) operably linked to a synthetic spider silk protein sequence (SEQ ID NO:20), operably linked to a fluorescent protein coding sequence (SEQ ID NO:13) which is operably linked to a transcription terminator sequence (SEQ ID NO:5).

Example 34

Synthetic Spider Silk Coding Protein Sequence

Example two is repeated with the exception of a corn endosperm tissue regulation region encoding a DNA construct represented as CeUrr-SS-FP-X including a promoter (SEQ ID NO:4) operably linked to a synthetic spider silk protein sequence (SEQ ID NO:20), operably linked to a fluorescent protein coding sequence (SEQ ID NO:13) which is operably linked to a transcription terminator sequence (SEQ ID NO:5).

Example 35

Synthetic Spider Silk Coding Protein Sequence

Example two is repeated with the exception of a plant endosperm tissue regulation region encoding a DNA construct represented as PeUrr-SS-FP-X including a promoter (SEQ ID NO:6) operably linked to a synthetic spider silk protein sequence (SEQ ID NO:20), operably linked to a fluorescent protein coding sequence (SEQ ID NO:13) which is operably linked to a transcription terminator sequence (SEQ ID NO:5).

Example 36

Synthetic Spider Silk Coding Protein Sequence in Barley Endosperm

Example two is repeated with the exception of a barley endosperm tissue regulation region encoding a DNA construct represented as PeUrr-SS-FP-X including a promoter (SEQ ID NO:7) operably linked to a synthetic spider silk protein sequence (SEQ ID NO:20), operably linked to a fluorescent protein coding sequence (SEQ ID NO:13) which is operably linked to a transcription terminator sequence (SEQ ID NO:5).

Example 37

Synthetic Spider Silk Coding Protein Sequence in Plant Leaf Tissue

Example two is repeated with the exception of a tobacco leaf tissue regulation region encoding a DNA construct represented as PsUrr-SS-FP-X including a promoter (SEQ ID NO:54) operably linked to a synthetic spider silk protein sequence (SEQ ID NO:20), operably linked to a fluorescent protein coding sequence (SEQ ID NO:13) which is operably linked to a transcription terminator sequence.

Example 38

Synthetic Spider Silk Coding Protein Sequence in Plant Leaf Tissue

Example two is repeated with the exception of a tobacco leaf tissue regulation region encoding a DNA construct represented as PsUrr-SS-FP-X including a promoter (SEQ ID NO:55) operably linked to a synthetic spider silk protein sequence (SEQ ID NO:20), operably linked to a fluorescent protein (SEQ ID NO:13) which is operably linked to a transcription terminator sequence.

Example 39

Synthetic Spider Silk Coding Protein Sequence in Plant Leaf Tissue

Example two is repeated with the exception of a tobacco leaf tissue regulation region encoding a DNA construct represented as PsUrr-SS-FP-X including a promoter (SEQ ID NO:56) operably linked to a synthetic spider silk protein sequence (SEQ ID NO:20), operably linked to a fluorescent protein coding sequence (SEQ ID NO:13) which is operably linked to a transcription terminator sequence.

Example 40

Exemplary Methods for Designing Synthetic Spider Silk Proteins for Expression in Plants The following methods for designing synthetic spider silk proteins are based on the amino acid composition of spider silk proteins and how repetitive regions of amino acid sequences contribute to the structural/physical properties of spider silk proteins.

Synthetic spider silk proteins may be comprised of a series of tandem exact repeats of amino acid sequence regions identified as possessing a particular spectrum of physical properties. Exact repeats comprise regions of amino acid sequences that are duplicated precisely. Alternatively, synthetic spider silk proteins may be comprised of a series of tandem inexact repeats identified as having a spectrum of physical properties. Inexact repeats may comprise regions of amino acid sequences in which at least one amino acid in the basic inexact repeat unit has been altered, as long as the alteration does not change the spectrum of physical properties characteristic of the basic inexact repeat unit.

In order to increase the tensile strength of a minor ampullate silk, for example, to adapt it for applications in which strength and very little elasticity are needed, such as bulletproof vests, the $(GA)_n$ regions may be replaced by $(A)_n$ regions. This change would increase the tensile strength. The typical MiSp1 protein has sixteen (GA) units. Replacing eight (GA) regions, for example, with (A) regions would increase the tensile strength from 100,000 psi to at least 400,000 psi. Moreover, if the (A)n regions are as long as the (GA)n regions the tensile strength would increase to greater than 600,000 psi.

To create a fiber with high tensile strength and greater elasticity than major ampullate silk, the number of regions may be increased from 4-5 regions, the range of regions typically found in naturally occurring major ampullate spider silk proteins, to a larger number of regions. For example, if the number are increased to 10-12 regions, the elasticity would increase to 50-60%. If the number are further increased to 25-30 regions, the elasticity would be near 100%. Such fibers may be used to advantage in coverings for wounds (for example, burn wounds) to facilitate easier placement and provide structural support. Such fibers may also be used for clothing and as fibers in composite materials.

The tensile strength of a very elastic flagelliform silk may be increased by replacing some of the units with (A)n regions. A flagelliform silk protein contains an average of 50 units per repeat. Replacing two units in each repeat with (A) regions may, therefore, increase the tensile strength of a flagelliform silk by a factor of four to achieve a tensile strength of about 400,000 psi. Uses for such flagelliform silk proteins are similar to those described for major ampullate proteins having augmented elasticity. The flagelliform proteins have additional utility in that the spacer regions confer the ability to attach functional molecules like antibiotics and/or growth factors (or combinations thereof) to composites comprising flagelliform proteins.

Synthetic spider proteins may also comprise the following elastic sequence motifs: from *Araneus* dragline; from *Lactrodectus* dragline; and from *Argiope* dragline. Genes comprising 2, 4, 8 and 16 repeats of these motifs may be constructed. The naturally occurring linker, connected to a poly-alanine segment of eight residues may be used to flank each repeat unit. The poly-alanine segment may be used as in the natural protein for fiber formation. This entire unit may be increased up to 16 repeat units to generate an encoded protein of 70-80 kD. Varying the number of these motifs alters the amount of elasticity from about 30% (for a synthetic spider silk protein coding sequence comprising two repeats derived from *Araneus*) to nearly 200% (for a synthetic spider silk protein coding sequence comprising sixteen repeats derived from *Argiope*). Varying the sequence of the motifs modifies the elastic modulus (higher with *Araneus*, lower with *Argiope*).

Genes encoding synthetic spider proteins derived from one of the *Araneus* MaSp2 protein analog genes may also be constructed. Such *Araneus* MaSp2 protein analog genes comprise beta-sheet motifs from poly-alanine segments of 5 and 14 residues that are the smallest and largest poly-alanine tracts found in the major ampullate silk proteins. These segments may also be constructed the novel sequence motif (gly-ala or gly-val) with the numerical value of n ranging from 3 to 8, the range observed in natural spider silk proteins. Varying the length and sequence of the beta-sheet region alters the tensile strength from approximately that of the typical minor ampullate silk (100,000 psi) to at least 600,000 psi, double that of dragline silk. Moreover, the specific sequence of the repeat influences the tensile strength of the fiber.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The present invention, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A DNA construct wherein said DNA construct comprises:
   (a) a nucleic acid sequence comprising a plant endosperm tissue promoter;
   (b) wherein said plant endosperm tissue promoter is operably linked to a DNA sequence encoding a synthetic spider silk protein sequence, wherein said protein sequence is selected from the group consisting of SEQ ID NO: 20, SEQ ID NO: 21, SEQ ID NO: 22, SEQ ID N 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 36, SEQ ID NO: 38, and SEQ ID NO: 40;
   (c) wherein said DNA sequence encoding said spider silk protein sequence is operably linked to a DNA sequence encoding a regulatory region of a transcription terminator sequence, wherein said regulatory region of said transcription terminator sequence comprises SEQ ID NO: 5; and
   (d) wherein said regulatory region of said transcription terminator sequence is operably linked to a sortable marker selected from the group consisting of SEQ ID NO: 13, SEQ ID NO: 15, SEQ ID NO: 47, SEQ ID NO: 49, SEQ ID NO: 51, and SEQ ID NO: 53.

2. A DNA construct wherein said DNA construct comprises:
   (a) a nucleic acid sequence comprising a corn plant endosperm tissue promoter;
   (b) wherein said corn plant endosperm tissue promoter is operably linked to a DNA sequence encoding a synthetic spider silk protein sequence, wherein said protein sequence is selected from the group consisting of SEQ ID NO: 20, SEQ ID NO: 21, SEQ ID NO: 22, SEQ ID N 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 36, SEQ ID NO: 38, and SEQ ID NO: 40;
   (c) wherein said DNA sequence encoding said spider silk protein sequence is operably linked to a DNA sequence encoding a regulatory region of a transcription terminator sequence, wherein said regulatory region of said transcription terminator sequence comprises SEQ ID NO: 5; and
   (d) wherein said regulatory region of said transcription terminator sequence is operably linked to a sortable marker selected from the group consisting of SEQ ID NO: 13, SEQ ID NO: 15, SEQ ID NO: 47, SEQ ID NO: 49, SEQ ID NO: 51, and SEQ ID NO: 53.

3. A transgenic plant having said DNA construct of claim 1 stably integrated into it's genome under conditions suitable for expression of said DNA construct in a plant endosperm, wherein the DNA construct expresses a protein in said plant endosperm, wherein the expressed protein is a spider silk protein.

4. A method for producing synthetic spider silk proteins in a tissue of plant endosperm said method comprising growing a transgenic plant having said DNA construct of claim 1 stably integrated into it's genome under conditions suitable for expression of the DNA construct in a plant endosperm, wherein the DNA construct expresses a protein in said plant endosperm, wherein the expressed protein is a spider silk protein.

5. A transgenic corn plant having said DNA construct of claim 2 stably integrated into it's genome under conditions suitable for expression of said DNA construct in a plant endosperm, wherein the DNA construct expresses a protein in said plant endosperm, wherein the expressed protein is a spider silk protein.

6. A method for producing synthetic spider silk proteins in a tissue of a corn plant endosperm said method comprises growing a transgenic corn plant having said DNA construct of claim 2 stably integrated into it's genome under conditions suitable for expression of the DNA construct in a corn plant endosperm, wherein the DNA construct expresses a protein in said corn plant endosperm, wherein the expressed protein is a spider silk protein.

7. A DNA construct wherein said DNA construct comprises:
   (a) a nucleic acid sequence comprising a plant endosperm tissue promoter;
   (b) wherein said plant endosperm tissue promoter is operably linked to a DNA sequence encoding a synthetic spider silk protein sequence;
   (c) wherein said DNA sequence encoding said spider silk protein sequence is operably linked to a DNA sequence encoding a regulatory region of a transcription terminator sequence, wherein said regulatory region of said transcription terminator sequence comprises SEQ ID NO: 5; and
   (d) wherein said regulatory region of said transcription terminator sequence is operably linked to a sortable marker selected from the group consisting of SEQ ID NO: 13, SEQ ID NO: 15, SEQ ID NO: 47, SEQ ID NO: 49, SEQ ID NO: 51, and SEQ ID NO: 53.

8. A transgenic plant having said DNA construct of claim 7 stably integrated into it's genome under conditions suitable for expression of said DNA construct in a plant endosperm, wherein the DNA construct expresses a protein in said plant endosperm, wherein the expressed protein is a spider silk protein.

9. A method for producing synthetic spider silk proteins in a tissue of a corn plant endosperm said method comprises growing a transgenic corn plant having said DNA construct of claim 7 stably integrated into it's genome under conditions suitable for expression of the DNA construct in a corn plant endosperm, wherein the DNA construct expresses a protein in said corn plant endosperm, wherein the expressed protein is a spider silk protein.

* * * * *

SEQUENCE LISTING

```
<160> NUMBER OF SEQ ID NOS: 68

<210> SEQ ID NO 1
<211> LENGTH: 3803
<212> TYPE: DNA
<213> ORGANISM: Zea mays

<400> SEQUENCE: 1
```

```
tgttgcacat ctttacccac aagtcatgtt acccatctgc caagggtca tgaatcccat      60 acacctctac catggaagcg agacagggta cactacgag gcctttacaa agttccacta     120
gctttagaaa acccgctaca aggatccccc gtctgaccgc catcacagca aacccgaga    180 acctccctac accgaccact cccctactat ccttgcccct ttcgggtaag atagtcttcc   240
actagctttc ctaattagtc agccaagggc gtcccatacc acccttatgg tagcactgtt   300
tttccgggtg gtcgctccat gttccaatta acataataat cttatcatga acaataaata   360
acaaaaaatg ataataaaag catgatcatg aataatgtgt atctcaatac ccaaaaccac   420
ataaagcaat agcaggtact acccaaaagt tcagtggtaa acaaggtata aagatagtca   480 aactggttg acctattggg tctcatcaaa attaacctat gcagatcata atgattaaca    540
gtaacattat tgggtaaata gaagtgatca agggcacaag ttgccttcaa cgagatcctg   600
ctcagcagtc tccacctgct gaacacctgg gtcctcagtg gcttgcttgt ctactcgcaa   660
caatacaaac aaacatggta taggagaaat taacatcaca ccaaacagca gaacagaatg   720
catgataata ttctacgtgt cataacgaga tggtaggaac aagaatcact aaattcagag   780
ttacgatttt ctgaagttat taggtgctta gtatagaata aatcaagtgg ataattttac   840
tctatgtttt atggctaaac agagttacca agtgataaac aatattaata caaaattaat   900
gcaactggaa tggaccaaaa aggagttaaa atggattttc tatgaattaa tctaggtttt   960
ggaattgttt ttatactaaa tattcatttt ctcggcttat tattaaccct ggtattttat  1020
ttggactgcg gacgcaaatg ctagaaacta cagggtccaa tatatgaaaa tcagggcatg  1080
gatgtaatta atttacaata gcagtggacg gcgggttaat tcagtaattc cctaggggca  1140
cttaagcaaa tatccatcgc aaagggtat tgttggatcc cgaccgttgg atcagatccg   1200
aaggccgaga atagatcgcg cccacacaac tgcgtcgtgc actgaccacc ctccggttaa  1260
gattcgacgg accaaattta atgaaatcca aaccaccac agccccacga tcagcaatct   1320
acggtccctc ttaacccaga tgaatcggta tccgacttct aatctaagca gttcctcaat  1380
cgatcaacgc tccagggcct tcttctatct cccaacgcag atcgagctac ggtcgcttgc  1440
acccgaggaa cgccgacaca gcgagcggcg gaccagcggt tctgggtaat gatttggagc  1500
acaaacaata ttggcgcgac ataggaatga tggcaactat taggttgtga ccttactagt  1560
gtcagcggtg tgggcagggt cgcccacggg aaaccagtgc gacggtgctc ccggcttgtt  1620
aatgacggtg tgctggtccc gacacggtga tgccccaaac gccccgccg tacgagaaca   1680 ccgcagacgc ccctgctcga ctccgccctc ggcttccgc gccacctcg cacttcgacg    1740 gccgcaccga ccctctgacc tctccttttc tctcctttct cactcctatc ggtagctaca  1800
acagaagcga ctcccaacgt ggcgcaaacc ctcgaagcat acggctgggg aaggtggcag  1860
ccaggtttat atcctaggcg cccgaggaaa tcgtgtggac ggctgttacg tttcgcccgc  1920
ggggcgcgat tcgcgcgaag aagactgtat gcgaggtagg gcccactagc agtgagccat  1980
cacccaggga agcgcgcatg catcgattga cacgcgaccc caacagtcag gcgacccgag  2040
tgtgcagacg gtcgcgatgg tgaaagtggc tagctcgcgc ggacgcgtag gggcattggg  2100
ccgaaatgcg tttcagcggt ccaacttctt tttttcttgt cttttttct ttcctttcc    2160 tttctatttt tagatttcaa atttaagttc aaatttttg tggtgaattt tctaaaaatc   2220
cacatatcag tatgaaaaga atttatatat aaatctattt atttatatat ttattttttt  2280
tctatgttat ttccaatttc taaatgtaa attaggttaa atcgccattt ggacactaat   2340
atatctttat tagtattact attattatat gcacaaccaa ataaactcca acatgatgca  2400
```

```
tcgattattt gtatgtcatt ggttaattat tcactttaaa tatgttcctt aacgattctc    2460
atgaaacaga aggccatgca cataaagatg tatccctttt ttctatattc ccagagttgg    2520
gtattacaac attcatctat gcattctagg atttcaatta ctctcaatct tttagtattt    2580
gttccttcat tgtcaaatca cttctcatct aactactatg cttgtttaac cagcagaaca    2640
atactacaac aatatccatt tataaaggct ttaatagcaa actttacata ttcatatcat    2700
gttaaggttg tcacatgtgt aaaggtgaag agatcatgca tgtcattcca cataaatgaa    2760
aagaattcct atataaaaat gacatgtttt gttgtaggta gtggaaatta tctttccagc    2820
aaagaccata taatccgata aagctgataa ctaaatgtca aaatcgagta agtgccatat    2880
catctatatc ttatctgttg tttggaaaaa gacaaaatcc aaaaaaaaat atatgagatc    2940
tcacatgtat aaatagctcc caaatcagta gttaatacat ctcccataat attttcagca    3000
ttcaaaaaca caccaagcga agcgcactag caacgaccta acaccaatgg ctaccaagat    3060
attagccctc cttgcgcttc ttgcccttttt agtgagcgca acaaatgcgt tcattattcc    3120
acagtgctca cttgctccta gtgccagtat tccacagttc ctcccaccag ttacttcaat    3180
gggcttcgaa catccagccg tgcaagccta caggctacaa ctagcgcttg cggcgagcgc    3240
cttacaacaa ccaattgccc aattgcaaca acaatccttg cacatctaa ccctacaaac    3300 cattgcaacg caacaacaac aacagtttct gccatcactg agccacctag ccgtggtgaa    3360
ccctgtcacc tacttgcaac agcagctgct tgcatccaac ccacttgctc tggcgaacgt    3420
agctgcatac cagcaacaac aacagctgca acagtttatg ccagtgctca gtcaactagc    3480
catggtgaac cctgccgtct acctacaact actttcatct agcccgctcg cggtgggcaa    3540
tgcacctacg tacctacaac aacagttgct gcaacaaatt gtaccagctc tgactcagct    3600
agctgtggca aaccctgctg cctacttaca acagttgctt ccattcaacc aactggctgt    3660
gtcaaactct gctgcgtacc tacaacagcg caacagtta cttaatccat tggcagtggc    3720
taacccattg gtcgctacct tcctgcagca gcaacaacaa ttgctgccat acaaccagtt    3780
ctctttgatg aaccctgcct tga                                           3803
```

<210> SEQ ID NO 2
<211> LENGTH: 1612
<212> TYPE: DNA
<213> ORGANISM: Zea mays

<400> SEQUENCE: 2

```
gaattcctat ataaaaacga catgttttgt tgtaggtagt ggaaactatc tttccagcaa      60
agaccatata atccgataaa gctgataact aaatgtcgaa atcgagtagg tgccatatca     120
tctatatctt atctgttgtt tggaaaaaga caaaatccaa aaaaaatata tgagatctca     180
cctgtataaa tagctcccaa atcagtagtt aatacatctc ccataatatt ttcagcattc     240
agaaacacac caagcgaacg actagcaacg acctaacaac aatggctacc aagatattag     300
ccctccttgc gcttcttgcc cttttagtga gcgcaacaaa tgtgttcatt attccacagt     360
gctcacttgc tcctagtgcc attattccac agttcctccc accagttact tcaatgggct     420
tcgaacatcc agccgtgcaa gcctataggc tacaactagt gcttgcggcg agcgccttac     480
aacaaccaat tgcccaattg caacaacaat ccttggcaca tctaacccta caaccatcg      540 caacgcaaca acaacaacat tttctgccat cactgagcca cctagcagtg gtgaaccctg     600
tcgcctactt gcaacagcag ctgcttgcat ccaacccact tgctctggcg aacgtagcta     660
```

```
cataccagca acaacaacag ctgcaacagt ttatgccagc gctcagtcaa ctagccatgg    720
tgaaccctgc cgtctaccta caactgcttt catctagccc gctcgctgtg ggcaatgcac    780
ctacgtacct acaacaacag ttgctgcaac agattgtacc agctctaact catcagctag    840
ctatggcaaa ccctgctacc tacttacaac agttgcttcc attcaaccaa ttggctgtgt    900
cgaactctgc tgcgtaccta acacagcgac aacaattact taatccattg gcagtggcta    960
acccattggt cgctaccttc ctgcagcagc aacaattgct gccatacaac cagttctctt   1020
tgatgaaccc tgccttgcag caacccatcg ttggaggtgc catcttttag attacatatg   1080
agatgtactc gacaatggtg ccctcatacc ggcatgtgtt tcctagaaat aatcaatata   1140
ttgattgaga tttatctcga tatatttctg aactatgttc atcatataaa taactgaaaa   1200
catcaaatcg taattttaaa gctcatgctt ggtcaataca tagataatac aatattactt   1260
catcatccca atgatgtcct agcacaacct attgaatgtt aatgtttggt tgtgtggggg   1320
tgtgtttata acatagatgt gattatttgt gcttttttgtt gagtatatac atatatggta   1380
tgttgatttg atatagtgat ggacacatgc tttggccttg gatattcaaa tcacttgtac   1440
ttgcacgaag caaaacataa tataagttta gaagtaaact tgtaactgtg tccaaacatg   1500
ctcacacaaa gtcatatcgc attatatttt tttggtaaat attcaacaca tgtattttt    1560 acaagaaccc aaattttaca gacaaatgca gcattgtaga catgtagaat tc            1612
```

<210> SEQ ID NO 3
<211> LENGTH: 262
<212> TYPE: PRT
<213> ORGANISM: Zea mays

<400> SEQUENCE: 3

```
Met Ala Thr Lys Ile Leu Ala Leu Leu Ala Leu Leu Ala Leu Leu Val
1               5                   10                  15

Ser Ala Thr Asn Val Phe Ile Ile Pro Gln Cys Ser Leu Ala Pro Ser
                20                  25                  30

Ala Ile Ile Pro Gln Phe Leu Pro Pro Val Thr Ser Met Gly Phe Glu
            35                  40                  45

His Pro Ala Val Gln Ala Tyr Arg Leu Gln Leu Val Leu Ala Ala Ser
        50                  55                  60

Ala Leu Gln Gln Pro Ile Ala Gln Leu Gln Gln Gln Ser Leu Ala His
65                  70                  75                  80

Leu Thr Leu Gln Thr Ile Ala Thr Gln Gln Gln Gln His Phe Leu Pro
                85                  90                  95

Ser Leu Ser His Leu Ala Val Val Asn Pro Val Ala Tyr Leu Gln Gln
                100                 105                 110

Gln Leu Leu Ala Ser Asn Pro Leu Ala Leu Ala Asn Val Ala Thr Tyr
            115                 120                 125

Gln Gln Gln Gln Gln Leu Gln Gln Phe Met Pro Ala Leu Ser Gln Leu
        130                 135                 140

Ala Met Val Asn Pro Ala Val Tyr Leu Gln Leu Leu Ser Ser Ser Pro
145                 150                 155                 160

Leu Ala Val Gly Asn Ala Pro Thr Tyr Leu Gln Gln Gln Leu Leu Gln
                165                 170                 175

Gln Ile Val Pro Ala Leu Thr His Gln Leu Ala Met Ala Asn Pro Ala
            180                 185                 190

Thr Tyr Leu Gln Gln Leu Leu Pro Phe Asn Gln Leu Ala Val Ser Asn
        195                 200                 205
```

```
Ser Ala Ala Tyr Leu Gln Gln Arg Gln Gln Leu Leu Asn Pro Leu Ala
    210                 215                 220
Val Ala Asn Pro Leu Val Ala Thr Phe Leu Gln Gln Gln Leu Leu
225                 230                 235                 240
Pro Tyr Asn Gln Phe Ser Leu Met Asn Pro Ala Leu Gln Gln Pro Ile
                245                 250                 255
Val Gly Gly Ala Ile Phe
            260

<210> SEQ ID NO 4
<211> LENGTH: 2809
<212> TYPE: DNA
<213> ORGANISM: Zea mays

<400> SEQUENCE: 4
ggggacaagt tgtacaaaa aagcaggctg ctcgatccac ctaggcttgt tgcacatctt      60
tacccacaag tcatgttacc catctgccaa ggggtcatga atcccataca cctctaccat    120
ggaagcgaga cagggtaaca ctacgaggcc tttacaaagt tccactagct ttagaaaacc    180
cgctacaagg atccccgtc tgaccgccat cacagcaaaa cccgagaacc tccctacacc     240
gaccactccc ctactatcct tgccccttc gggtaagata gtcttccact agctttccta    300
attagtcagc caagggcgtc ccataccacc cttatggtag cactgttttt ccgggtggtc    360
gctccatgtt ccaattaaca taataatctt atcatgaaca ataaataaca aaaaatgata    420
ataaaagcat gatcatgaat aatgtgtatc tcaatcccaa aaccacata aagcaatagc     480
aggtactacc caaaagttca gtggtaaaca aggtataaag atagtcaaac tgggttgacc    540
tattgggtct catcaaaatt aacctatgca gatcataatg attaacagta acattattgg    600
gtaaatagaa gtgatcaagg gcacaagttg ccttcaacga gatcctgctc agcagtctcc    660
acctgctgaa cacctgggtc ctcagtggct tgcttgtcta ctcgcaacaa tacaaacaaa    720
catggtatag gagaaattaa catcacacca aacagcagaa cagaatgcat gataatattc    780
tacgtgtcat aacgagatgg taggaacaag aatcactaaa ttcagagtta cgattttctg    840
aagttattag gtgcttagta tagaataaat caagtggata attttactct atgttttatg    900
gctaaacaga gttaccaagt gataaacaat attaatacaa aattaatgca actggaatgg    960
accaaaaagg agtaaaatg gatttctat gaattaatct aggttttgga attgtttta    1020
tactaaatat tcattttctc ggcttattat taaccctggt attttatttg gactgcggac    1080
gcaaatgcta gaaactacag ggtccaatat atgaaaatca gggcatggat gtaattaatt    1140
tacaatagca gtggacggcg ggttaattca gtaattccct aggggcactt aagcaaatat    1200
ccatcgcaaa ggggtattgt tggatcccga ccgttggatc agatccgaag ccgagaata    1260
gatcgcgccc acacaactgc gtcgtgcact gaccaccctc cggttaagat tcgacggacc    1320
aaatttaatg aaatccaaac cacccacagc cccacgatca gcaatctacg gtccctctta    1380
acccagatga atcggtatcc gacttctaat ctaagcagtt cctcaatcga tcaacgctcc    1440
agggccttct tctatctccc aacgcagatc gagctacggt cgcttgcacc cgaggaacgc    1500
cgacacagcg agcggcggac cagcggttct gggtaatgat ttggagcaca acaatattg    1560
gcgcgacata ggaatgatgg caactattag gttgtgacct tactagtgtc agcggtgtgg    1620
gcagggtcgc ccacgggaaa ccagtgcgac ggtgctcccg gcttgttaat gacggtgtgc    1680
tggtcccgac acgtgatgc cccaaacgcc ccgccgtac gagaacaccg cagacgcccc     1740
tgctcgactc cgccctcggc ttcccgcgcc cacctcgcac ttcgacggcc gcaccgaccc    1800
```

-continued

```
tctgacctct cctttctct cctttctcac tcctatcggt agctacaaca gaagcgactc    1860
ccaacgtggc gcaaaccctc gaagcatacg gctggggaag gtggcagcca ggtttatatc    1920
ctaggcgccc gaggaaatcg tgtggacggc tgttacgttt cgcccgcggg gcgcgattcg    1980
cgcgaagaag actgtatgcg aggtagggcc cactagcagt gagccatcac ccagggaagc    2040
gcgcatgcat cgattgacac gcgaccccaa cagtcaggcg acccgagtgt gcagacggtc    2100
gcgatggtga agtggctag ctcgcgcgga cgcgtagggg cattgggccg aaatgcgttt    2160
cagcggtcca acttctttt ttcttgtctt tttttctttc cttttccttt ctattttag     2220 atttcaaatt taagttcaaa ttttttgtgg tgaattttct aaaaatccac atatcagtat    2280
gaaaagaatt tatatataaa tctatttatt tatatattta ttttttttct atgttatttc    2340
caatttctaa aatgtaaatt aggttaaatc gccatttgga cactaatata tcttattag    2400 tattactatt attatatgca caaccaaata aactccaaca tgatgcatcg attatttgta    2460
tgtcattggt taattattca ctttaaatat gttccttaac gattctcatg aaacagaagg    2520
ccatgcacat aaagatgtat cccttttttc tatattccca gagttgggta ttacaacatt    2580
catctatgca ttctaggatt tcaattactc tcaatctttt agtatttgtt ccttcattgt    2640
caaatcactt ctcatctaac tactatgctt gtttaaccag cagaacaata ctacaacaat    2700
atccatttat aaaggcttta atagcaaact ttacatattc atatcatgtt aaggttgtca    2760
catgtgtaaa ggtgaagaga tcatgcatgt cattccacat aaatgaaaa              2809
```

<210> SEQ ID NO 5
<211> LENGTH: 1114
<212> TYPE: DNA
<213> ORGANISM: Zea mays

<400> SEQUENCE: 5

```
agattacata tgagatgtac tcgacaatgg tgccctcata ccgacatgtg tttcctagaa     60
ataatcaata tattgattga gatttatctc gatatatttc tgaactatgt tcatcatata    120
aataattgaa acatcaaat cataattttta aactcatgct tggtcaatac atagataata    180
caatattact tcatcatccc aatgatgtcc tagcccaacc tattgaatgt taatgtttgg    240
ttgtgtgagg gtgtgtttat aacatagatg tgattatttg cgcttttttgt tgagtatata    300 catatatggt atgttgattt gatataggga tggacacatg cttggccctt ggatattcaa    360
atcacttgta cttgcacgaa gcaaaacata atatatagtt tagaagtaaa cttgtaacta    420
tgtccaaaca tgctcacaca aagtcatacc gcattataat tttttggtaa atattcaaca    480
catgtatttt ttacaagaac ccaaatttta cagacaaatg cagcattgta gacatgtaga    540
attctttgaa gcatgtgaac ttaacaacac caatgtcatt aaatcaacta gacccctatga   600 gtaacaattt cgatattgca aacaccaaat tatggaactt attgctgaa aaaattatga     660 tcaatgtgaa gttaaatta ttataccata aatatatcaa agatttttt gaggaagta       720 aaaattgcat ggaatgggct gcccaacgtg atagctcact tttatgctag gtagcattac    780
caaagatggg aacgttctga tgaacaccaa acccactcaa ataatatta tatttgggtt    840 gtttagttgt aaaagtgaag acccaagttt aaagtaccaa ttggccaatg ccattcgatt    900
gttttgttca aagagcactt ggtacgtcat ttggactcgt atcttagtcc aatatattgc    960
attttgcttc aatgtgtaga atccgacaaa gtgcatgttc taaaattgta aatctaacta    1020
aattagaaag cttgttacta atttgatggt ttattaggtg tagctcatcc tgtggtctcg    1080
```

```
ctacgaccca gctttcttgt acaaagtggt cccc                                1114
```

<210> SEQ ID NO 6
<211> LENGTH: 3091
<212> TYPE: DNA
<213> ORGANISM: Triticum sp.

<400> SEQUENCE: 6

```
ctgcagtact agtgaaccca tcattggctt gatattgcgc catgctaagt tctgttggca      60
ctaaagcctt atattaagat tggtttggta tgtgattatt cctagaacta ctagccttag     120
tgaagcatgc actgttagcc ccaaaattgt ttgatttgtc acttctctga actgtggaaa     180
tggtatgtat gcagttttcc tcagcatctt cttggtttgg actaatttat atacatagga     240
gttcgtaaag aagtgtatat acgaagtacc ataggccagc gaaatgcttt ttttaacaaa     300
ggcaagcact ttgtcacatt tcattaaata ggaaggacag tggcataaat atatacacaa     360
caaaaaggcc aaggtgggcg aaaccccta  aaaatatata ctcctgaaat tagtgctccc     420
aagtgctttg caacggctac cacagaacaa ttcacctagc tcttgattct tatggggtgc     480
acggcatgct gctaactgat ctgaagactc ttgcactcaa tgtttgaatg aaggtgtaga     540
gttttctcac cagatgtgtg agcacataat ctttgcttgc tatgatgcaa gtactgacaa     600
gtgccatttt ctccttttat caaattattg agccagcttt ctttagcaca gaccgtcggt     660
aatctgtaaa gaaaaaaaaa agtgtggcat gcaggaaatt tgattacagc tgtccactgt     720
cctgcttcta atatgcttta aactagcagc aatgtgcatt gggtgaagtt aggttacaga     780
atcacaccag tttgactgtc actctggaac ttcggatggt ttagcccatt ttagctgaaa     840
cagcaagcac atggtgcatg ctcatagact gccactaact tattcatggc tacatggttg     900
gtgtccatgg tcgtacatt  tatcgggatt atgagcagtt gtgctgatac acggatttcc     960
ttttccagga tctggccggc aagcagacca tcgttgtaag tgggcatcac gggaagctcc    1020
acgtggacgt tctcaggttc atcatcgacg aaggtggcgg gtactcagat aaacctatag    1080
ctgccgttgt tttcccttcg aaggaagtca tccggagcac agagggaacg gcctcccaga    1140
attaatctag acaccatcgg aaatgcaagc taatgtcgta acggagtatc atatttccaa    1200
aaacacagaa ctgaggtttt aatgtataac gtcgagtaaa taaatcaata atgtgtgatc    1260
ttctcctaag catgcaatgt gacaactagg acaagtgagc tcctgtgtgc cagttgacag    1320
catcattata cttcttgcta cttggctgtc gatatgaatc atgaacggca atggccctgt    1380
ttttaaacag cagctttttct tgttaaccga agtaatacat cctgcacggc accttctata    1440
gacaaacaga tctcggacgg tggttgtaca tgcctacatg gtccagggca gaacaatagt    1500
ttttttttct ttcgaattcg gcagtgcaaa aggtgcgagg atatcaagtc acaggggagt    1560
tgttgaatta acggtcggga gagagcctcc tggcaggtct cttgtacttc tcgtttgttt    1620
cttcctgatg aacagcaagc gaaagcgaac ggacatgtcc acggggaagg gaccacgacg    1680
ctaagataac tcggccggcc ggtccctccc tccgtcgtcc gccagtcaca ccggtcacca    1740
ggcttgacgc ttaataaata tctctcctgt atctaggaac aaaggatcac cgagggctta    1800
aaataagcat gactgcacgg cttcaggtgg tagcataatg accatgggga agtgagatct    1860
tgatgcccgt tttgcagcca gagaattcag aaacacctcc attttagatt ttttttttgtt   1920
cttttcggac ggtgggtcgt ggagagatta gcgtctagtt ttcttaaaag aacaggccat    1980
ctaggccctg ctttacaaaa ggctcaacca gtccaaaacg tctgctagga tcaccagctg    2040
caaagttaag cgcgagacca ccaaaacagg cgcattcgaa ctggacagac gctcacgcag    2100
```

-continued

```
gagcccagca ccacaggctt gagcctgaca gcggacgtga gtgcgtgaca catgggtca    2160
tccatgggcg tcggagcaag gaagagagac gcacatgaac accatgatga tgctatcagg   2220
cctgatggag ggagcaacca tgcaccttt ccctctgga aattcatagc tcacactttt     2280
ttttaatgga agcaagagtt ggcaaacaca tgcattttca aacaaggaaa attaattctc   2340
aaaccaccat gacatgcaat tctcaaacca tgcaccgacg agtccatgcg aggtggaaac   2400
gaagaactga aaatcaacat cccagttgtc gagtcgagaa gaggatgacg ctgaaagtat   2460
gcgtattacg atatcattta catacatgta caaatacata atgtacccta caatttgttt   2520
tttggagcag agtggtgtgg tcttttttt tacacgaaaa tgccatagct ggcccgcatg    2580
cgtgcagatc ggatgatcgg tcggagacga cggacaatca gacactcacc aactgctttt   2640
gtctgggaga caataaatgt ttttgtaaa caaaataaat acttataaac gagggtacta    2700
gaggccgcta acggcatggc caggtaaacg cgctcccagc cgttggttg cgatctcgtc    2760
ctcccgcacg cagcgtcgcc tccaccgtcc gtccgtcgct ctctgccacc tctgctgtgc   2820
gcgcgcacga gggaggaaga cgacgccgca cacacactca cacacggcac actccccgtg   2880
ggtcccctt ccggctcggc gtctatctcc tctcccccgc ccatccccat gcactgcacc    2940
gtacccgcca gcttccaccc ccgccgcaca cgttgctccc ccttctcatc gcttctcaat   3000
taatatctcc atcactcggg ttccgcgctg catttcggcc ggcgggttga gtgagatctg   3060
ggcgactggc tgactcaatc actacgcggg g                                  3091
```

<210> SEQ ID NO 7
<211> LENGTH: 296
<212> TYPE: DNA
<213> ORGANISM: Zea mays

<400> SEQUENCE: 7

```
ttcctctcca gaagtttctg cagggcacaa ctagagagag agcccagcac tagataagta    60
gggagggggg aagaagagca tccaagccta ctcctggatc tccttcaagc agctatagct   120
agcataatta actcatgggt gcatagagat atgccgccga cgacccatat ctatgggtcc   180
ctcccttgc actgcatctt cttcttcctc ctcctcgacc tccttcaatt attcctagtg    240
tttgcttctc ccttccttga cctttgcttg gaaccattga tagttactta ttgggc       296
```

<210> SEQ ID NO 8
<211> LENGTH: 21
<212> TYPE: DNA
<213> ORGANISM: Zea mays

<400> SEQUENCE: 8

```
tgttgcacat ctttacccac a                                              21
```

<210> SEQ ID NO 9
<211> LENGTH: 20
<212> TYPE: DNA
<213> ORGANISM: Zea mays

<400> SEQUENCE: 9

```
caaggcaggg ttcatcaaag                                                20
```

<210> SEQ ID NO 10
<211> LENGTH: 16
<212> TYPE: DNA
<213> ORGANISM: Zea mays

```
<400> SEQUENCE: 10
atgaaccctg ccttgc                                                          16

<210> SEQ ID NO 11
<211> LENGTH: 23
<212> TYPE: DNA
<213> ORGANISM: Zea mays

<400> SEQUENCE: 11
tgagctacac ctaataaacc atc                                                  23

<210> SEQ ID NO 12
<211> LENGTH: 678
<212> TYPE: DNA
<213> ORGANISM: Acropora nobilis

<400> SEQUENCE: 12
atggcctcct ccgaggacgt catcaaggag ttcatgcgct tcaaggtgcg catggagggc          60
tccgtgaacg gccacgagtt cgagatcgag ggcgagggcg agggccgccc ctacgagggc         120
acccagaccg ccaagctgaa ggtgaccaag ggcggccccc tgcccttcgc ctgggacatc         180 ctgtccctc agttccagta cggctccaag gcctacgtga agcaccccgc cgacatcccc          240
gactacttga agctgtcctt ccccgagggc ttcaagtggg agcgcgtgat gaacttcgag         300
gacggcggcg tggtgaccgt gacccaggac tcctccctgc aggacggcga gttcatctac         360
aaggtgaagc tgcgcggcac caacttcccc tccgacggcc ccgtaatgca gaagaagacc         420
atgggctggg aggcctccac cgagcggatg taccccgagg acggcgccct gaagggcgag         480
atcaagatga ggctgaagct gaaggacggc ggccactacg acgccgaggt caagaccacc         540
tacatggcca agaagcccgt gcagctgccc ggcgcctaca agaccgacat caagctggac         600
atcacctccc acaacgagga ctacaccatc gtggaacagt acgagcgcgc cgagggccgc         660
cactccaccg cgcctaa                                                        678

<210> SEQ ID NO 13
<211> LENGTH: 225
<212> TYPE: PRT
<213> ORGANISM: Acropora nobilis

<400> SEQUENCE: 13

Gly Ala Gly Gly Val Ala Ala Leu Gly Ala Leu Val Leu Phe His Asp
1               5                   10                  15

Gly Val Val Leu Val Val Gly Gly Asp Val Gln Leu Asp Val Gly Leu
            20                  25                  30

Val Gly Ala Gly Gln Leu His Gly Leu Leu Gly His Val Gly Gly Leu
        35                  40                  45

Asp Leu Gly Val Val Val Ala Ala Val Leu Gln Leu Pro His Leu
    50                  55                  60

Asp Leu Ala Leu Gln Gly Ala Val Leu Gly Val His Pro Leu Gly Gly
65                  70                  75                  80

Gly Leu Pro Ala His Gly Leu Leu His Tyr Gly Ala Val Gly Gly
                85                  90                  95

Glu Val Gly Ala Ala Gln Leu His Leu Val Asp Glu Leu Ala Val Leu
            100                 105                 110

Gln Gly Gly Val Leu Gly His Gly His His Ala Ala Val Leu Glu Val
        115                 120                 125

His His Ala Leu Pro Leu Glu Ala Leu Gly Glu Gly Gln Leu Gln Val
```

```
Val Gly Asp Val Gly Gly Val Leu His Val Gly Leu Gly Ala Val Leu
145                 150                 155                 160

Glu Leu Arg Gly Gln Asp Val Pro Gly Glu Gly Gln Gly Ala Ala Leu
                165                 170                 175

Gly His Leu Gln Leu Gly Gly Leu Gly Ala Leu Val Gly Ala Ala Leu
                180                 185                 190

Ala Leu Ala Leu Asp Leu Glu Leu Val Ala Val His Gly Ala Leu His
                195                 200                 205

Ala His Leu Glu Ala His Glu Leu Leu Asp Asp Val Leu Gly Gly Gly
                210                 215                 220

His
225
```

<210> SEQ ID NO 14
<211> LENGTH: 696
<212> TYPE: DNA
<213> ORGANISM: Acropora nobilis

<400> SEQUENCE: 14

```
atgtcttatt caaagcaagg catcgcacaa gtaatgaaga cgaaatacca tatggaaggc    60
agtgtcaatg ccatgaatt cacgatcgaa ggtgtaggaa ctggaaaccc ttacgaaggc   120
acacagatgt ccgaattagt gatcaccaag cctgcaggaa accccttcc attctccttt   180
gacattctgt caacagtctt tcaatatgga acaggtgct tcacaaagta ccctgaagga   240
atgactgact atttcaagca agcattccca gatggaatgt catatgaaag gtcatttcta   300
tatgaggatg gaggagttgc tacagccagc tggaacattc gtcttgagag agattgcttc   360
atccacaaat ccatctatca tggcgttaac tttcccgctg atggacccgt aatgaaaaag   420
aagaccattg gctgggataa agccttcgaa aaatgactg tgtccaaaga cgtgttaaga   480
ggtgatgtga ctgagtttct tatgctcgaa ggaggtggtt accacagctg ccagtttcac   540
tccacttaca aaccagaaaa gccggctgca ctgcccccga atcatgtcgt agaacatcac   600
attgtgagga ctgaccttgg ccaaagtgca aaaggcttca cagtcaagct ggaagaacat   660
gctgcggctc atgttaaccc tttgaaggtt caataa                             696
```

<210> SEQ ID NO 15
<211> LENGTH: 231
<212> TYPE: PRT
<213> ORGANISM: Acropora nobilis

<400> SEQUENCE: 15

```
Met Ser Tyr Ser Lys Gln Gly Ile Ala Gln Val Met Lys Thr Lys Tyr
1               5                   10                  15

His Met Glu Gly Ser Val Asn Gly His Glu Phe Thr Ile Glu Gly Val
                20                  25                  30

Gly Thr Gly Asn Pro Tyr Glu Gly Thr Gln Met Ser Glu Leu Val Ile
            35                  40                  45

Thr Lys Pro Ala Gly Lys Pro Leu Pro Phe Ser Phe Asp Ile Leu Ser
        50                  55                  60

Thr Val Phe Gln Tyr Gly Asn Arg Cys Phe Thr Lys Tyr Pro Glu Gly
65                  70                  75                  80

Met Thr Asp Tyr Phe Lys Gln Ala Phe Pro Asp Gly Met Ser Tyr Glu
                85                  90                  95

Arg Ser Phe Leu Tyr Glu Asp Gly Gly Val Ala Thr Ala Ser Trp Asn
```

```
                100             105             110
Ile Arg Leu Glu Arg Asp Cys Phe Ile His Lys Ser Ile Tyr His Gly
            115                 120                 125
Val Asn Phe Pro Ala Asp Gly Pro Val Met Lys Lys Thr Ile Gly
        130                 135                 140
Trp Asp Lys Ala Phe Glu Lys Met Thr Val Ser Lys Asp Val Leu Arg
145                 150                 155                 160
Gly Asp Val Thr Glu Phe Leu Met Leu Glu Gly Gly Tyr His Ser
                165                 170                 175
Cys Gln Phe His Ser Thr Tyr Lys Pro Glu Lys Pro Ala Ala Leu Pro
                180                 185                 190
Pro Asn His Val Val Glu His His Ile Val Arg Thr Asp Leu Gly Gln
            195                 200                 205
Ser Ala Lys Gly Phe Thr Val Lys Leu Glu Glu His Ala Ala Ala His
        210                 215                 220
Val Asn Pro Leu Lys Val Gln
225                 230

<210> SEQ ID NO 16
<211> LENGTH: 6062
<212> TYPE: DNA
<213> ORGANISM: Neisseria gonorrhoeae

<400> SEQUENCE: 16
cccatcttaa gacttcacaa gacttgtgaa atcagaccac tgctcaatgc ggaacgcccg      60
aatatcgcgg acagaagacg gaaaccaagg cagagctttt agctcgttga tggctgaaaa     120
caggttagcc atatcttcgt tttggcaggt gtacaaactt ccctgaatgc gggtaaagcc     180
gaatttccgc agggtgtatc caatatccgc gtaggcttgg gaaatgcctt tcggatggtt     240
ttgagcggta tcggcaacca ccaaatcaaa agaaatcgcg tacattaggc agcctttggg     300
tcttgaacga tgtgggacag tttgtattgc gtgtgttcgc cgctttccgg cagttcaata     360
tttacgagcc aatcgccgtc cggaagctgt tcggcaggcg tgccgacgat gtacatcacg     420
ccgtaatcgc caaaggtgcg gattgaaccg gtggggatag tggtttgcat ggttagttct     480
cctgttgggt ttggttttca ggctggtttg tcatgtacaa acccgttggg cagcttttt      540
cggctgttgt gcgtttgatg ccgtcaggca gaaaaattct ccattttttg gctagaacta     600
tatctgcaag atcatcaacc gttgcgcttt tcaaagcagg atttgcgtta atttccgaat     660
acagaaaatc tttgaatgcc gagtacagag catcgcggtt tattgcgtat cttgtcatgc     720
tgtttcgctt tggttgtcag tttcagacgg cataggcttg ccgcgcctgt accaagtggc     780
gcgggaaatg ccgaagtgtt ccacggtttt atcgcggctg atagagtttt cggctaggta     840
gtcggcgcgg gattgcgacc atgcccgaaa acggttctt gtggaacagc cgaagcgttt      900
tgccagttct ttagccgtaa cgtctcgctt ggtggttttc agttttggat aggccatatt     960
tcaaagctcc gtgatgattt tgttctgcc tgcattgatg gttgttttcc gcaaactatt     1020
ccgatgagcc tgcaattccg aaaaccgtcg attgctggct gcaatatcaa acttgtacca    1080
aacccagtta gcgattgatt tggagataca tttcacttct ttttcccaca tcgggacagg    1140
gaaatcccca tttacccgca tacactggta atgcacttct ttcagccagc cttgcaccgt    1200
gtagccctgc tgtttgaacg ccaacacgtt tttgtgcgcc caacggctca caaggttaaa    1260
caccgtgcaa tttctgctta atccgaccgc ttccacgtta gagcgaccga tagggctt     1320
aaacttgtct aaatccacga aatccgcaag atactccaaa tcgtagcccc tgattgcgtc    1380
```

```
aggaacgccg cgcagcgtca gccaatgcgg atgttcggga tttttcgtaa tcagcgatac  1440
aaagcccaca tcaccgcgca atttcgcctt atatgctgct tcaagtgcag caagatagcg  1500
cagggctttt tgtctcccac cgtattccgc cgtcagcaca ggcgcggaaa gcgcataggc  1560
aaggtgtgcg ccgccgtttt ccctgttgat tgccgcccaa gcaggcatag gcagattatt  1620
gtcttcccaa gccaaccccg ccccttcgta atccaagtca aagagcataa acacacgcag  1680
atgcgacgga ttgacttgga tgtagcgacg tttgatggcg gcagcgtaag agcgcaccag  1740
cataggcgct tctttgaaat ctttgcagta tggcttgtgt gggatacgtt cttgcaagaa  1800
gaggtcgggt tgggtgtata attggctcat gttgtatctc gaaaccccg tgcagattgg   1860 cgtttggcgg gggttttgct ttgtctaaga tttgcagatt gtatgcttgt ttttaagatg  1920
atacaactat gtcaaaataa ccataatcag ataacagccc gatagggtt cttatttcaa   1980 aattttccaa tccgcaattt agcgaagcca gcaggcgaag cggtaaagct tggagcgcag  2040
cagcgcgacc taagccggcc agcagggcgg cgttttgggg gaaacatgaa accagttccg  2100
acagggcggc gtgcgtgttc ttcccggagt tcttcatgga gtatcggcga aatgccgtga  2160
tgaaatgccg ttttttttgag cagaaagcag tcaaaaacag gggtattttg ccctttttgac 2220 aggttcgagt gccgccgaaa agcgaacaaa gcaactcatc atccgagtca gcccgaccga  2280
gtttgagact ttgaccccgac agaagaccca tccgaattta gcccgctaca ttcgggagcg  2340
ggttttggaa gatggcaaag catccgacaa aaaaaccgtc aaattccaat tcccgcccga  2400
agtcgtgcgc gtccttgcag gcatgggtaa caacctgaac caaatagcca aggccctgaa  2460
caccgccgca aaggtcggca cgttgggcaa tgtggaagca ctcaaggcga cgaccgagct  2520
ggcagcgttg gaacgttcct taaattccct acgggatttt ttagccaaag aaaagaacgg  2580
atggcagtcc caatgattgt gcagttttc aataggggga aaggcggcgg gagtggtccg    2640
atagactatc ttctaggcaa agaccgcgac cgagaagaag ccagattatt acgcggcgac  2700
cccgaagaaa ccgccgccct gataaacagc agcgattacg ccaagaaata caccgccggc  2760
tgcctgagct ttgaagaaag caacatcccc gccgaacaga acacgccct gatggacagc   2820 ttcgaagagt gtattttgc aggcttggac aaagaccaat acaactgcct atgggtagaa   2880
caccgagaca aagggcgttt ggaactcaac ttcgtgatac cgaacatcga gcttttgagc  2940
ggaaagcggt tacagcccta ctactacgcc gccgacagag aagagtgga cgcatggcgc   3000 accatgcaga acctgacgca cggatacagc gacccagacg accccgccaa acggcagagc  3060
atgacccaag ccaaagacct gccgagaaac acgcaggaag ccgcacagag catcacagag  3120
catcacagac ggcttagaag ccctagccct atcaggcaag ctaaaaagcc gcgcagacgt  3180
gctggaaacg ctggaaaagg taggttttga aatatcacga gcgaccatca gcagcatcag  3240
catcaagaac ccggacccaa aagggcgcaa catccgactg aaaggcgcac tgtatgagca  3300
agatttccga tttggcgaag accttcgagc agacatcacg caccgaagcc gccagcatag  3360
agcaacaaac gaaagcagac ttagagacgt tacggaaaaa tatcaacgag gcattgaagc  3420
aaagcgagca gaaaataacc gccgatataa acgcccggca gttacgcatg agcaaggcag  3480
tattcaagcc ctatctgtgg agcttgctag gtatatcggc ggcagggttg atagtcatag  3540
cagggctgtt catagcgata tggagcgtca agaacgagct ggacgacttg aaacagcaga  3600
gagccgaagc agagcgcacc ctagacctgt tggaaaccaa gaccaaaggt ttgcacactgg 3660 aaaattgccc agtcgagaac agcaaagcaa cgcgggtatg cgtagcgacc gagaagcgaa  3720
```

```
tgctggacgc gttagcggaa ttagagagca atcacgcagc aatcgagcag cgaatgatga    3780
aagccttaac gcacttgggc gaaaggttgg cagagctaga gcaggaaaac acgagtttag    3840
cgcagcagct agcgagcttg gcagccgagt tagagcggca gagcgaaata cagcaacggc    3900
agagcgaaat cttgaatcaa ctagccaaac gataagccaa cgacacaaac gaacccaaag    3960
caggggatgg ggaatgagcc gatgattacc gagaacgaac gcgacaggcg aacagccgca    4020
tggctgatag agacctacgg ggcagaagcc gtagcggaag cagaaacccg cattgcgggt    4080
gcgagaaagc cctatccgag cgatatcgcc aaagtattgg gggctagcct acccgaagcc    4140
ctaaaacgca cagaaaacgc cgcagcgcgc caaaaactgg cagggctgcg gcggatttgg    4200
acggtaaggc agttaagact tcacaaactt gtgggatctg gaattcgagc tcggtacccg    4260
gggatccccg gggccgtctg aagacggcca gtgccaagct tactccccat cccccctgttg    4320
acaattaatc atcggctcgt ataatgtgtg gaattgtgat cggataacaa tttcacacag    4380
gaaacaggat cctctagatt taagaaggag atatacatat gagtaaagga gaagaacttt    4440
tcactggagt tgtcccaatt cttgttgaat tagatggtga tgttaatggg cacaaatttt    4500
ctgtcagtgg agagggtgaa ggtgatgcaa catacggaaa acttacccct aaatttattt    4560
gcactactgg aaaactacct gttccatggc caacacttgt cactactttc ggttatggtg    4620
ttcaatgctt tgcgagatac ccagatcata tgaaacagca tgacttttc aagagtgcca    4680
tgcctgaagg ttatgtacag gaaagaacta tattttcaa agatgacggg aactacaaga    4740
cacgtgctga agtcaagttt gaaggtgata cccttgttaa tagaatcgag ttaaaaggta    4800
ttgattttaa agaagatgga acattcttg gacacaaatt ggaatacaac tataactcac    4860
acaatgtata catcatggca gacaaacaaa gaatggaat caagttaac ttcaaaatta    4920
gacacaacat tgaagatgga agcgttcaac tagcagacca ttatcaacaa aatactccaa    4980
ttggcgatgg ccctgtcctt ttaccagaca accattacct gtccacacaa tctgcccttt    5040
cgaaagatcc caacgaaaag agagaccaca tggtccttct tgagtttgta acagctgctg    5100
ggattacaca tggcatggat gaactataca aataaatgtc cagacctcct gcaggcatgc    5160
aagctagatc ccccgggctg cagtactccc catccccctg ttgacaatta atcatcggct    5220
cgtataatgt gtggaattgt gagcggataa caatttcaca caggaaacag gatcgatccg    5280
agattttcag gagctaagga agctaaaatg gagaaaaaaa tcactggata taccaccgtt    5340
gatatatccc aatggcatcg taaagaacat tttgaggcat ttcagtcagt tgctcaatgt    5400
acctataacc aaaccgttca gctggatatt acggcctttt taaagaccgt aaagaaaaat    5460
aagcacaagt tttatccggc ctttattcac attcttgccc gcctgatgaa tgctcatccg    5520
gaattccgta tggcaatgaa agacggtgag ctggtgatat gggatagtgt tcacccttgt    5580
tacaccgttt tccatgagca aactgaaacg ttttcatcgc tctggagtga ataccacgac    5640
gatttccggc agtttctaca catatattcg caagatgtgg cgtgttacgg tgaaaacctg    5700
gcctatttcc ctaaagggtt tattgagaat atgtttttcg tctcagccaa tccctgggtg    5760
agtttcacca gttttgattt aaacgtggcc aatatggaca cttcttcgc cccgttttc    5820
accatgggca atattatac gcaaggcgac aaggtgctga tgccgctggc gattcaggtt    5880
catcatgccg tttgtgatgg cttccatgtc ggcagaatgc ttaatgaatt acaacagtac    5940
tgcgatgagt ggcagggcgg ggcgtaattt ttttaaggca gttattggtg cccttaaacg    6000
cctggttgct acgcctgaat aagtgataat aagcggatga atggcagaaa ttcggatcga    6060
tc                                                                  6062
```

<210> SEQ ID NO 17
<211> LENGTH: 238
<212> TYPE: PRT
<213> ORGANISM: Neisseria gonorrhoeae

<400> SEQUENCE: 17

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 18
<211> LENGTH: 717
<212> TYPE: DNA
<213> ORGANISM: Artificial sequence
<220> FEATURE:
<223> OTHER INFORMATION: Synthetic construct

<400> SEQUENCE: 18

```
atgtccaagg gcgaggagct gttcaccggc gtggtgccta tcctcgtgga gctcgacggc      60
gacgtgaacg gccacaagtt cagcgtgtcc ggcgagggcg agggcgacgc cacctacggc     120
aagctgaccc tgaagttcat ctgcaccacc ggcaagctcc cggtgccatg gccaaccctg     180
gtgaccacct tcggctacgg cctgcagtgc ttcgccaggt accccgacca catgaagagg     240
cacgacttct tcaagagcgc catgccagag ggctacgtgc aggagaggac catcttcttc     300
aaggacgacg gcaactacaa gaccagggcc gaggtgaagt tcgagggcga caccctggtg     360
aacaggatcg agctgaaggg catcgacttc aaggaggacg gcaacatcct gggccacaag     420
ctggagtaca actacaactc ccacaacgtg tacatcatgg ccgacaagca gaagaacggc     480
```

```
atcaaggtga acttcaagat ccgccacaac atcgaggacg gctccgtgca gctggccgac      540
cactaccagc agaacacccc aatcggcgac ggcccggtgc tcctccctga caaccactac      600
ctcagctacc agtccgccct cagcaaggac ccgaacgaga gagggacca catggtgctg       660 ctggagttcg tgaccgccgc cggcatcacc cacggcatgg acgagctcta caagtga         717
```

<210> SEQ ID NO 19
<211> LENGTH: 238
<212> TYPE: PRT
<213> ORGANISM: Artificial sequence
<220> FEATURE:
<223> OTHER INFORMATION: Synthetic construct

<400> SEQUENCE: 19

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 20
<211> LENGTH: 54
<212> TYPE: PRT
<213> ORGANISM: Nephila clavipes

<400> SEQUENCE: 20

```
Gly Pro Gly Gly Tyr Gly Pro Gly Gln Gln Pro Gly Gly Tyr Gly
1               5                   10                  15

Pro Gly Gln Gln Gly Pro Gly Gly Tyr Gly Pro Gly Gln Gln Gly Pro
            20                  25                  30

Gly Gly Tyr Gly Pro Gly Gln Gln Gly Pro Gly Gly Pro Ser Gly Pro
```

```
                    35                  40                  45

Gly Ser Ala Ala Ala Ala
    50

<210> SEQ ID NO 21
<211> LENGTH: 58
<212> TYPE: PRT
<213> ORGANISM: Nephila clavipes

<400> SEQUENCE: 21

Gly Pro Gly Gly Tyr Gly Pro Gly Gln Gln Gly Pro Gly Gly Tyr Gly
1               5                   10                  15

Pro Gly Gln Gln Gly Pro Gly Gly Tyr Gly Pro Gly Gln Gln Gly Pro
            20                  25                  30

Gly Gly Tyr Gly Pro Gly Gln Gln Gly Pro Gly Gly Pro Ser Gly Pro
        35                  40                  45

Gly Ser Ala Ala Ala Ala Ala Ala Ala Ala
    50                  55

<210> SEQ ID NO 22
<211> LENGTH: 66
<212> TYPE: PRT
<213> ORGANISM: Nephila clavipes

<400> SEQUENCE: 22

Gly Pro Gly Gly Tyr Gly Pro Gly Gln Gln Gly Pro Gly Gly Tyr Gly
1               5                   10                  15

Pro Gly Gln Gln Gly Pro Gly Gly Tyr Gly Pro Gly Gln Gln Gly Pro
            20                  25                  30

Gly Gly Tyr Gly Pro Gly Gln Gln Gly Pro Gly Gly Pro Ser Gly Pro
        35                  40                  45

Gly Ser Ala Ala Ala Ala Ala Ala Ala Ala Ala Ala Ala Ala Ala Ala
    50                  55                  60

Ala Ala
65

<210> SEQ ID NO 23
<211> LENGTH: 178
<212> TYPE: PRT
<213> ORGANISM: Nephila clavipes

<400> SEQUENCE: 23

Gly Pro Gly Gly Tyr Gly Pro Gly Gln Gln Gly Pro Gly Gly Tyr Gly
1               5                   10                  15

Pro Gly Gln Gln Gly Pro Gly Gly Tyr Gly Pro Gly Gln Gln Gly Pro
            20                  25                  30

Gly Gly Tyr Gly Pro Gly Gln Gln Gly Pro Gly Gly Tyr Gly Pro Gly
        35                  40                  45

Gln Gln Gly Pro Gly Gly Tyr Gly Pro Gly Gln Gln Gly Pro Gly Gly
    50                  55                  60

Tyr Gly Pro Gly Gln Gln Gly Pro Gly Gly Tyr Gly Pro Gly Gln Gln
65                  70                  75                  80

Gly Pro Gly Gly Tyr Gly Pro Gly Gln Gln Gly Pro Gly Gly Tyr Gly
            85                  90                  95

Pro Gly Gln Gln Gly Pro Gly Gly Tyr Gly Pro Gly Gln Gln Gly Pro
            100                 105                 110

Gly Gly Tyr Gly Pro Gly Gln Gln Gly Pro Gly Gly Tyr Gly Pro Gly
        115                 120                 125
```

Gln Gln Gly Pro Gly Gly Tyr Gly Pro Gly Gln Gln Gly Pro Gly Gly
            130                 135                 140

Tyr Gly Pro Gly Gln Gln Gly Pro Gly Gly Tyr Gly Pro Gly Gln Gln
145                 150                 155                 160

Gly Pro Gly Gly Pro Ser Gly Pro Gly Ser Ala Ala Ala Ala Ala
                165                 170                 175

Ala Ala

<210> SEQ ID NO 24
<211> LENGTH: 41
<212> TYPE: PRT
<213> ORGANISM: Argiope sp.

<400> SEQUENCE: 24

Gly Gly Tyr Gly Pro Gly Ala Gly Gln Gln Gly Pro Gly Ser Gln Gly
1               5                   10                  15

Pro Gly Ser Gly Gly Gln Gln Pro Gly Gly Gln Gly Pro Tyr Gly Pro
                20                  25                  30

Ser Ala Ala Ala Ala Ala Ala Ala Ala
            35                  40

<210> SEQ ID NO 25
<211> LENGTH: 68
<212> TYPE: PRT
<213> ORGANISM: Argiope sp.

<400> SEQUENCE: 25

Gly Gly Tyr Gly Pro Gly Ala Gly Gln Gln Gly Pro Gly Ser Gln Gly
1               5                   10                  15

Pro Gly Ser Gly Gly Gln Gln Pro Gly Gly Gln Gly Tyr Gly Pro
                20                  25                  30

Gly Ala Gly Gln Gln Gly Pro Gly Ser Gln Gly Pro Gly Ser Gly Gly
                35                  40                  45

Gln Gln Pro Gly Gly Gln Gly Pro Tyr Gly Pro Ser Ala Ala Ala Ala
        50                  55                  60

Ala Ala Ala Ala
65

<210> SEQ ID NO 26
<211> LENGTH: 95
<212> TYPE: PRT
<213> ORGANISM: Argiope sp.

<400> SEQUENCE: 26

Gly Gly Tyr Gly Pro Gly Ala Gly Gln Gln Gly Pro Gly Ser Gln Gly
1               5                   10                  15

Pro Gly Ser Gly Gly Gln Gln Pro Gly Gly Gln Gly Tyr Gly Pro
                20                  25                  30

Gly Ala Gly Gln Gln Gly Pro Gly Ser Gln Gly Pro Gly Ser Gly Gly
                35                  40                  45

Gln Gln Pro Gly Gly Gln Gly Tyr Gly Pro Gly Ala Gly Gln Gln
        50                  55                  60

Gly Pro Gly Ser Gln Gly Pro Gly Ser Gly Gly Gln Gln Pro Gly Gly
65                  70                  75                  80

Gln Gly Pro Tyr Gly Pro Ser Ala Ala Ala Ala Ala Ala Ala
                85                  90                  95

```
<210> SEQ ID NO 27
<211> LENGTH: 409
<212> TYPE: PRT
<213> ORGANISM: Artificial sequence
<220> FEATURE:
<223> OTHER INFORMATION: Argiope sp. and Nephila clavipes

<400> SEQUENCE: 27

Met Gly His His His His His His His His Ser Ser Gly His
1               5                   10                  15

Ile Asp Asp Asp Asp Lys His Met Leu Glu Asp Pro Pro Gly Gly Ala
            20                  25                  30

Gly Pro Gly Gly Ala Gly Pro Gly Gly Ala Gly Pro Gly Gly Ala Gly
            35                  40                  45

Pro Gly Gly Pro Ser Gly Pro Gly Ser Ala Ala Ala Ala Ala Ala
    50                  55                      60

Ala Gly Pro Gly Gly Pro Ser Gly Pro Gly Ser Ala Ala Ala Ala
65                  70                      75                  80

Ala Ala Ala Gly Pro Gly Gly Pro Ser Gly Pro Gly Ser Ala Ala Ala
                85                  90                  95

Ala Ala Ala Ala Ala Gly Pro Gly Gly Pro Ser Gly Pro Gly Ser Ala
                100                 105                 110

Ala Ala Ala Ala Ala Ala Gly Pro Gly Gly Pro Ser Gly Pro Gly
                115                 120                 125

Ser Ala Ala Ala Ala Ala Ala Ala Gly Pro Gly Gly Pro Ser Gly
    130                 135                 140

Pro Gly Ser Ala Ala Ala Ala Ala Ala Gly Pro Gly Gly Pro
145                 150                 155                 160

Ser Gly Pro Gly Ser Ala Ala Ala Ala Ala Ala Ala Gly Pro Gly
                165                 170                 175

Gly Pro Ser Gly Pro Gly Ser Ala Ala Ala Ala Ala Ala Ala Gly
                180                 185                 190

Pro Gly Gly Pro Ser Gly Pro Gly Ser Ala Ala Ala Ala Ala Ala
            195                 200                 205

Ala Gly Pro Gly Gly Pro Ser Gly Pro Gly Ser Ala Ala Ala Ala
        210                 215                 220

Ala Ala Ala Gly Pro Gly Gly Pro Ser Gly Pro Gly Ser Ala Ala
225                 230                 235                 240

Ala Ala Ala Ala Ala Gly Pro Gly Gly Pro Ser Gly Pro Gly Ser Ala
                245                 250                 255

Ala Ala Ala Ala Ala Ala Gly Pro Gly Gly Pro Ser Gly Pro Gly
                260                 265                 270

Ser Ala Ala Ala Ala Ala Ala Ala Gly Pro Gly Gly Pro Ser Gly
    275                 280                 285

Pro Gly Ser Ala Ala Ala Ala Ala Ala Gly Pro Gly Gly Pro
        290                 295                 300

Ser Gly Pro Gly Ser Ala Ala Ala Ala Ala Ala Ala Gly Pro Gly
305                 310                 315                 320

Gly Pro Ser Gly Pro Gly Ser Ala Ala Ala Ala Ala Ala Ala Gly
                325                 330                 335

Pro Gly Gly Pro Ser Gly Pro Gly Ser Ala Ala Ala Ala Ala Ala
            340                 345                 350

Ala Gly Pro Gly Gly Pro Ser Gly Pro Gly Ser Ala Ala Ala Ala
        355                 360                 365

Ala Ala Ala Gly Pro Gly Gly Pro Ser Gly Pro Gly Ser Ala Ala Ala
```

```
                370             375             380
Ala Ala Ala Ala Ala Gly Pro Gly Gly Pro Ser Gly Pro Gly Ser Ala
385                 390                 395                 400

Ala Ala Ala Ala Ala Ala Ala Gly Pro
            405
```

<210> SEQ ID NO 28
<211> LENGTH: 321
<212> TYPE: PRT
<213> ORGANISM: Artificial sequence
<220> FEATURE:
<223> OTHER INFORMATION: Argiope sp. and Nephila clavipes

<400> SEQUENCE: 28

```
Met Gly His His His His His His His His Ser Ser Gly His
1               5                   10                  15

Ile Asp Asp Asp Asp Lys His Met Leu Glu Asp Pro Pro Gly Gly Ala
            20                  25                  30

Gly Pro Gly Gly Ala Gly Pro Gly Gly Ala Gly Pro Gly Gly Ala Gly
            35                  40                  45

Pro Gly Gly Ala Gly Pro Gly Gly Ala Gly Pro Gly Gly Ala Gly Pro
        50                  55                  60

Gly Gly Ala Gly Pro Gly Gly Pro Ser Gly Pro Gly Ser Ala Ala Ala
65                  70                  75                  80

Ala Ala Ala Ala Ala Gly Pro Gly Gly Pro Ser Gly Pro Gly Ser Ala
                85                  90                  95

Ala Ala Ala Ala Ala Ala Gly Pro Gly Gly Pro Ser Gly Pro Gly
            100                 105                 110

Ser Ala Ala Ala Ala Ala Ala Gly Pro Gly Gly Pro Ser Gly
        115                 120                 125

Pro Gly Ser Ala Ala Ala Ala Ala Ala Gly Pro Gly Gly Pro
        130                 135                 140

Ser Gly Pro Gly Ser Ala Ala Ala Ala Ala Ala Gly Pro Gly
145                 150                 155                 160

Gly Pro Ser Gly Pro Gly Ser Ala Ala Ala Ala Ala Ala Ala Gly
                165                 170                 175

Pro Gly Gly Pro Ser Gly Pro Gly Ser Ala Ala Ala Ala Ala Ala
                180                 185                 190

Ala Gly Pro Gly Gly Pro Ser Gly Pro Gly Ser Ala Ala Ala Ala
            195                 200                 205

Ala Ala Ala Gly Pro Gly Gly Pro Ser Gly Pro Gly Ser Ala Ala Ala
            210                 215                 220

Ala Ala Ala Ala Gly Pro Gly Gly Pro Ser Gly Pro Gly Ser Ala
225                 230                 235                 240

Ala Ala Ala Ala Ala Ala Gly Pro Gly Gly Pro Ser Gly Pro Gly
                245                 250                 255

Ser Ala Ala Ala Ala Ala Ala Ala Gly Pro Gly Gly Pro Ser Gly
            260                 265                 270

Pro Gly Ser Ala Ala Ala Ala Ala Ala Ala Gly Pro Gly Gly Pro
        275                 280                 285

Ser Gly Pro Gly Ser Ala Ala Ala Ala Ala Ala Gly Pro Gly
        290                 295                 300

Gly Pro Ser Gly Pro Gly Ser Ala Ala Ala Ala Ala Ala Ala Gly
305                 310                 315                 320

Pro
```

<210> SEQ ID NO 29
<211> LENGTH: 253
<212> TYPE: PRT
<213> ORGANISM: Artificial sequence
<220> FEATURE:
<223> OTHER INFORMATION: Argiope sp. and Nephila clavipes

<400> SEQUENCE: 29

```
Met Gly His His His His His His His His Ser Ser Gly His
1               5                   10                  15

Ile Asp Asp Asp Lys His Met Leu Glu Asp Pro Pro Gly Gly Ala
            20                  25                  30

Gly Pro Gly Gly Ala Gly Pro Gly Gly Ala Gly Pro Gly Gly Ala Gly
        35                  40                  45

Pro Gly Gly Ala Gly Pro Gly Gly Ala Gly Pro Gly Gly Ala Gly Pro
    50                  55                  60

Gly Gly Ala Gly Pro Gly Gly Ala Gly Pro Gly Gly Ala Gly Pro Gly
65                  70                  75                  80

Gly Ala Gly Pro Gly Gly Ala Gly Pro Gly Gly Ala Gly Pro Gly Gly
                85                  90                  95

Ala Gly Pro Gly Gly Ala Gly Pro Gly Gly Ala Gly Pro Gly Gly Pro
            100                 105                 110

Ser Gly Pro Gly Ser Ala Ala Ala Ala Ala Ala Ala Gly Pro Gly
            115                 120                 125

Gly Pro Ser Gly Pro Gly Ser Ala Ala Ala Ala Ala Ala Ala Gly
        130                 135                 140

Pro Gly Gly Pro Ser Gly Pro Gly Ser Ala Ala Ala Ala Ala Ala
145                 150                 155                 160

Ala Gly Pro Gly Gly Pro Ser Gly Pro Gly Ser Ala Ala Ala Ala
                165                 170                 175

Ala Ala Ala Gly Pro Gly Gly Pro Ser Gly Pro Gly Ser Ala Ala Ala
            180                 185                 190

Ala Ala Ala Ala Ala Gly Pro Gly Gly Pro Ser Gly Pro Gly Ser Ala
        195                 200                 205

Ala Ala Ala Ala Ala Ala Gly Pro Gly Gly Pro Ser Gly Pro Gly
    210                 215                 220

Ser Ala Ala Ala Ala Ala Ala Ala Gly Pro Gly Gly Pro Ser Gly
225                 230                 235                 240

Pro Gly Ser Ala Ala Ala Ala Ala Ala Ala Gly Pro
            245                 250
```

<210> SEQ ID NO 30
<211> LENGTH: 829
<212> TYPE: PRT
<213> ORGANISM: Artificial sequence
<220> FEATURE:
<223> OTHER INFORMATION: Argiope sp. and Nephila clavipes

<400> SEQUENCE: 30

```
Met Gly His His His His His His His His Ser Ser Gly His
1               5                   10                  15

Ile Asp Asp Asp Asp Lys His Met Leu Glu Asp Pro Pro Gly Gly Ala
            20                  25                  30

Gly Pro Gly Gly Ala Gly Pro Gly Gly Ala Gly Pro Gly Gly Ala Gly
        35                  40                  45

Pro Gly Gly Ala Gly Pro Gly Gly Ala Gly Pro Gly Gly Ala Gly Pro
```

-continued

```
                50                  55                  60
Gly Gly Ala Gly Pro Gly Gly Ala Gly Pro Gly Gly Ala Gly Pro Gly
 65                  70                  75                  80

Gly Ala Gly Pro Gly Gly Ala Gly Pro Gly Gly Ala Gly Pro Gly Gly
                 85                  90                  95

Ala Gly Pro Gly Gly Ala Gly Pro Gly Gly Ala Gly Pro Gly Gly Ala
                100                 105                 110

Gly Pro Gly Gly Ala Gly Pro Gly Gly Ala Gly Pro Gly Gly Ala Gly
            115                 120                 125

Pro Gly Gly Ala Gly Pro Gly Gly Ala Gly Pro Gly Gly Ala Gly Pro
        130                 135                 140

Gly Gly Ala Gly Pro Gly Gly Ala Gly Pro Gly Gly Ala Gly Pro Gly
145                 150                 155                 160

Gly Ala Gly Pro Gly Gly Ala Gly Pro Gly Gly Ala Gly Pro Gly Gly
                165                 170                 175

Ala Gly Pro Gly Gly Ala Gly Pro Gly Gly Ala Gly Pro Gly Gly Ala
                180                 185                 190

Gly Pro Gly Gly Ala Gly Pro Gly Gly Ala Gly Pro Gly Gly Ala Gly
            195                 200                 205

Pro Gly Gly Ala Gly Pro Gly Gly Ala Gly Pro Gly Gly Ala Gly Pro
        210                 215                 220

Gly Gly Ala Gly Pro Gly Gly Ala Gly Pro Gly Gly Ala Gly Pro Gly
225                 230                 235                 240

Gly Ala Gly Pro Gly Gly Ala Gly Pro Gly Gly Ala Gly Pro Gly Gly
                245                 250                 255

Ala Gly Pro Gly Gly Ala Gly Pro Gly Gly Ala Gly Pro Gly Gly Ala
                260                 265                 270

Gly Pro Gly Gly Ala Gly Pro Gly Gly Ala Gly Pro Gly Gly Ala Gly
            275                 280                 285

Pro Gly Gly Ala Gly Pro Gly Gly Ala Gly Pro Gly Gly Ala Gly Pro
        290                 295                 300

Gly Gly Ala Gly Pro Gly Gly Ala Gly Pro Gly Gly Ala Gly Pro Gly
305                 310                 315                 320

Gly Ala Gly Pro Gly Gly Ala Gly Pro Gly Gly Ala Gly Pro Gly Gly
                325                 330                 335

Ala Gly Pro Gly Gly Ala Gly Pro Gly Gly Ala Gly Pro Gly Gly Ala
                340                 345                 350

Gly Pro Gly Gly Ala Gly Pro Gly Gly Ala Gly Pro Gly Gly Ala Gly
            355                 360                 365

Pro Gly Gly Ala Gly Pro Gly Gly Ala Gly Pro Gly Gly Ala Gly Pro
        370                 375                 380

Gly Gly Ala Gly Pro Gly Gly Ala Gly Pro Gly Gly Ala Gly Pro Gly
385                 390                 395                 400

Gly Ala Gly Pro Gly Gly Ala Gly Pro Gly Gly Ala Gly Pro Gly Gly
                405                 410                 415

Ala Gly Pro Gly Gly Ala Gly Pro Gly Gly Ala Gly Pro Gly Gly Ala
                420                 425                 430

Gly Pro Gly Gly Ala Gly Pro Gly Gly Ala Gly Pro Gly Gly Ala Gly
            435                 440                 445

Pro Gly Gly Ala Gly Pro Gly Gly Ala Gly Pro Gly Gly Ala Gly Pro
        450                 455                 460

Gly Gly Ala Gly Pro Gly Gly Ala Gly Pro Gly Gly Ala Gly Pro Gly
465                 470                 475                 480
```

Gly Ala Gly Pro Gly Gly Ala Gly Pro Gly Gly Ala Gly Pro Gly Gly
            485                 490                 495

Ala Gly Pro Gly Gly Ala Gly Pro Gly Gly Ala Gly Pro Gly Gly Ala
            500                 505                 510

Gly Pro Gly Gly Ala Gly Pro Gly Gly Ala Gly Pro Gly Gly Ala Gly
            515                 520                 525

Pro Gly Gly Ala Gly Pro Gly Gly Ala Gly Pro Gly Gly Ala Gly Pro
            530                 535                 540

Gly Gly Ala Gly Pro Gly Gly Ala Gly Pro Gly Gly Ala Gly Pro Gly
545                 550                 555                 560

Gly Ala Gly Pro Gly Gly Ala Gly Pro Gly Gly Ala Gly Pro Gly Gly
            565                 570                 575

Ala Gly Pro Gly Gly Ala Gly Pro Gly Gly Ala Gly Pro Gly Gly Ala
            580                 585                 590

Gly Pro Gly Gly Ala Gly Pro Gly Gly Ala Gly Pro Gly Gly Ala Gly
            595                 600                 605

Pro Gly Gly Ala Gly Pro Gly Gly Ala Gly Pro Gly Gly Ala Gly Pro
            610                 615                 620

Gly Gly Ala Gly Pro Gly Gly Ala Gly Pro Gly Gly Ala Gly Pro Gly
625                 630                 635                 640

Gly Ala Gly Pro Gly Gly Ala Gly Pro Gly Gly Ala Gly Pro Gly Gly
            645                 650                 655

Ala Gly Pro Gly Gly Ala Gly Pro Gly Gly Ala Gly Pro Gly Gly Ala
            660                 665                 670

Gly Pro Gly Gly Ala Gly Pro Gly Gly Ala Gly Pro Gly Gly Ala Gly
            675                 680                 685

Pro Gly Gly Ala Gly Pro Gly Gly Ala Gly Pro Gly Gly Ala Gly Pro
            690                 695                 700

Gly Gly Ala Gly Pro Gly Gly Ala Gly Pro Gly Gly Ala Gly Pro Gly
705                 710                 715                 720

Gly Ala Gly Pro Gly Gly Ala Gly Pro Gly Gly Ala Gly Pro Gly Gly
            725                 730                 735

Ala Gly Pro Gly Gly Ala Gly Pro Gly Gly Ala Gly Pro Gly Gly Ala
            740                 745                 750

Gly Pro Gly Gly Ala Gly Pro Gly Gly Ala Gly Pro Gly Gly Ala Gly
            755                 760                 765

Pro Gly Gly Ala Gly Pro Gly Gly Ala Gly Pro Gly Gly Ala Gly Pro
            770                 775                 780

Gly Gly Ala Gly Pro Gly Gly Ala Gly Pro Gly Gly Ala Gly Pro Gly
785                 790                 795                 800

Gly Ala Gly Pro Gly Gly Ala Gly Pro Gly Gly Ala Gly Pro Gly Gly
            805                 810                 815

Ala Gly Pro Gly Gly Ala Gly Pro Gly Gly Ala Gly Pro
            820                 825

<210> SEQ ID NO 31
<211> LENGTH: 409
<212> TYPE: PRT
<213> ORGANISM: Artificial sequence
<220> FEATURE:
<223> OTHER INFORMATION: Argiope sp. and Nephila clavipes

<400> SEQUENCE: 31

Met Gly His His His His His His His His Ser Ser Gly His
1               5                   10                  15

Ile Asp Asp Asp Lys His Met Leu Glu Asp Pro Pro Gly Gly Tyr
            20                  25                  30

Gly Pro Gly Gly Ser Gly Pro Gly Tyr Gly Pro Gly Ser Gly
        35                  40                  45

Pro Gly Gly Pro Ser Gly Pro Gly Ser Ala Ala Ala Ala Ala Ala
50                  55                  60

Ala Gly Pro Gly Gly Pro Ser Gly Pro Gly Ser Ala Ala Ala Ala
65                  70                  75                  80

Ala Ala Ala Gly Pro Gly Gly Pro Ser Gly Pro Gly Ser Ala Ala Ala
                85                  90                  95

Ala Ala Ala Ala Ala Gly Pro Gly Gly Pro Ser Gly Pro Gly Ser Ala
            100                 105                 110

Ala Ala Ala Ala Ala Ala Gly Pro Gly Gly Pro Ser Gly Pro Gly
            115                 120                 125

Ser Ala Ala Ala Ala Ala Ala Gly Pro Gly Gly Pro Ser Gly
    130                 135                 140

Pro Gly Ser Ala Ala Ala Ala Ala Ala Gly Pro Gly Gly Pro
145                 150                 155                 160

Ser Gly Pro Gly Ser Ala Ala Ala Ala Ala Ala Gly Pro Gly
            165                 170                 175

Gly Pro Ser Gly Pro Gly Ser Ala Ala Ala Ala Ala Ala Ala Gly
            180                 185                 190

Pro Gly Gly Pro Ser Gly Pro Gly Ser Ala Ala Ala Ala Ala
            195                 200                 205

Ala Gly Pro Gly Gly Pro Ser Gly Pro Gly Ser Ala Ala Ala Ala
    210                 215                 220

Ala Ala Gly Pro Gly Gly Pro Ser Gly Pro Gly Ser Ala Ala Ala
225                 230                 235                 240

Ala Ala Ala Ala Ala Gly Pro Gly Gly Pro Ser Gly Pro Gly Ser Ala
            245                 250                 255

Ala Ala Ala Ala Ala Ala Gly Pro Gly Gly Pro Ser Gly Pro Gly
            260                 265                 270

Ser Ala Ala Ala Ala Ala Ala Ala Gly Pro Gly Gly Pro Ser Gly
    275                 280                 285

Pro Gly Ser Ala Ala Ala Ala Ala Ala Gly Pro Gly Gly Pro
290                 295                 300

Ser Gly Pro Gly Ser Ala Ala Ala Ala Ala Ala Gly Pro Gly
305                 310                 315                 320

Gly Pro Ser Gly Pro Gly Ser Ala Ala Ala Ala Ala Ala Gly
            325                 330                 335

Pro Gly Gly Pro Ser Gly Pro Gly Ser Ala Ala Ala Ala Ala
            340                 345                 350

Ala Gly Pro Gly Gly Pro Ser Gly Pro Gly Ser Ala Ala Ala Ala
    355                 360                 365

Ala Ala Ala Gly Pro Gly Gly Pro Ser Gly Pro Gly Ser Ala Ala Ala
    370                 375                 380

Ala Ala Ala Ala Gly Pro Gly Gly Pro Ser Gly Pro Gly Ser Ala
385                 390                 395                 400

Ala Ala Ala Ala Ala Ala Gly Pro
            405

<210> SEQ ID NO 32
<211> LENGTH: 321

```
<212> TYPE: PRT
<213> ORGANISM: Artificial sequence
<220> FEATURE:
<223> OTHER INFORMATION: Argiope sp. and Nephila clavipes

<400> SEQUENCE: 32

Met Gly His His His His His His His His Ser Ser Gly His
1               5                   10                  15

Ile Asp Asp Asp Lys His Met Leu Glu Asp Pro Pro Gly Gly Tyr
            20                  25                  30

Gly Pro Gly Gly Ser Gly Pro Gly Gly Tyr Gly Pro Gly Ser Gly
            35                  40                  45

Pro Gly Gly Tyr Gly Pro Gly Ser Gly Pro Gly Gly Tyr Gly Pro
    50                  55                  60

Gly Gly Ser Gly Pro Gly Pro Ser Gly Pro Gly Ser Ala Ala Ala
65                  70                  75                  80

Ala Ala Ala Ala Ala Gly Pro Gly Gly Pro Ser Gly Pro Gly Ser Ala
                85                  90                  95

Ala Ala Ala Ala Ala Ala Gly Pro Gly Gly Pro Ser Gly Pro Gly
                100                 105                 110

Ser Ala Ala Ala Ala Ala Ala Ala Gly Pro Gly Gly Pro Ser Gly
                115                 120                 125

Pro Gly Ser Ala Ala Ala Ala Ala Ala Ala Gly Pro Gly Gly Pro
    130                 135                 140

Ser Gly Pro Gly Ser Ala Ala Ala Ala Ala Ala Ala Gly Pro Gly
145                 150                 155                 160

Gly Pro Ser Gly Pro Gly Ser Ala Ala Ala Ala Ala Ala Ala Gly
                165                 170                 175

Pro Gly Gly Pro Ser Gly Pro Gly Ser Ala Ala Ala Ala Ala Ala
                180                 185                 190

Ala Gly Pro Gly Gly Pro Ser Gly Pro Gly Ser Ala Ala Ala Ala
                195                 200                 205

Ala Ala Ala Gly Pro Gly Gly Pro Ser Gly Pro Gly Ser Ala Ala Ala
                210                 215                 220

Ala Ala Ala Ala Ala Gly Pro Gly Gly Pro Ser Gly Pro Gly Ser Ala
225                 230                 235                 240

Ala Ala Ala Ala Ala Ala Gly Pro Gly Gly Pro Ser Gly Pro Gly
                245                 250                 255

Ser Ala Ala Ala Ala Ala Ala Ala Gly Pro Gly Gly Pro Ser Gly
                260                 265                 270

Pro Gly Ser Ala Ala Ala Ala Ala Ala Ala Gly Pro Gly Gly Pro
    275                 280                 285

Ser Gly Pro Gly Ser Ala Ala Ala Ala Ala Ala Ala Gly Pro Gly
    290                 295                 300

Gly Pro Ser Gly Pro Gly Ser Ala Ala Ala Ala Ala Ala Ala Gly
305                 310                 315                 320

Pro

<210> SEQ ID NO 33
<211> LENGTH: 253
<212> TYPE: PRT
<213> ORGANISM: Artificial sequence
<220> FEATURE:
<223> OTHER INFORMATION: Argiope sp. and Nephila clavipes

<400> SEQUENCE: 33
```

```
Met Gly His His His His His His His His Ser Ser Gly His
1               5                   10                  15

Ile Asp Asp Asp Lys His Met Leu Glu Asp Pro Pro Gly Gly Tyr
            20                  25                  30

Gly Pro Gly Gly Ser Gly Pro Gly Gly Tyr Gly Pro Gly Gly Ser Gly
        35                  40                  45

Pro Gly Gly Tyr Gly Pro Gly Gly Ser Gly Pro Gly Gly Tyr Gly Pro
    50                  55                  60

Gly Gly Ser Gly Pro Gly Gly Tyr Gly Pro Gly Gly Ser Gly Pro Gly
65                  70                  75                  80

Gly Tyr Gly Pro Gly Gly Ser Gly Pro Gly Gly Tyr Gly Pro Gly Gly
                85                  90                  95

Ser Gly Pro Gly Gly Tyr Gly Pro Gly Gly Ser Gly Pro Gly Gly Pro
            100                 105                 110

Ser Gly Pro Gly Ser Ala Ala Ala Ala Ala Ala Ala Gly Pro Gly
            115                 120                 125

Gly Pro Ser Gly Pro Gly Ser Ala Ala Ala Ala Ala Ala Ala Gly
    130                 135                 140

Pro Gly Gly Pro Ser Gly Pro Gly Ser Ala Ala Ala Ala Ala Ala
145                 150                 155                 160

Ala Gly Pro Gly Gly Pro Ser Gly Pro Gly Ser Ala Ala Ala Ala
                165                 170                 175

Ala Ala Ala Gly Pro Gly Gly Pro Ser Gly Pro Gly Ser Ala Ala
            180                 185                 190

Ala Ala Ala Ala Ala Gly Pro Gly Gly Pro Ser Gly Pro Gly Ser Ala
        195                 200                 205

Ala Ala Ala Ala Ala Ala Gly Pro Gly Gly Pro Ser Gly Pro Gly
    210                 215                 220

Ser Ala Ala Ala Ala Ala Ala Ala Gly Pro Gly Gly Pro Ser Gly
225                 230                 235                 240

Pro Gly Ser Ala Ala Ala Ala Ala Ala Ala Gly Pro
                245                 250

<210> SEQ ID NO 34
<211> LENGTH: 969
<212> TYPE: PRT
<213> ORGANISM: Artificial sequence
<220> FEATURE:
<223> OTHER INFORMATION: Argiope sp. and Nephila clavipes

<400> SEQUENCE: 34

Met Gly His His His His His His His His Ser Ser Gly His
1               5                   10                  15

Ile Asp Asp Asp Lys His Met Leu Glu Asp Pro Pro Gly Gly Tyr
            20                  25                  30

Gly Pro Gly Gly Ser Gly Pro Gly Gly Tyr Gly Pro Gly Gly Ser Gly
        35                  40                  45

Pro Gly Gly Tyr Gly Pro Gly Gly Ser Gly Pro Gly Gly Tyr Gly Pro
    50                  55                  60

Gly Gly Ser Gly Pro Gly Gly Tyr Gly Pro Gly Gly Ser Gly Pro Gly
65                  70                  75                  80

Gly Tyr Gly Pro Gly Gly Ser Gly Pro Gly Gly Tyr Gly Pro Gly Gly
                85                  90                  95

Ser Gly Pro Gly Gly Tyr Gly Pro Gly Gly Ser Gly Pro Gly Gly Tyr
            100                 105                 110
```

```
Gly Pro Gly Gly Ser Gly Pro Gly Gly Tyr Gly Pro Gly Gly Ser Gly
            115                 120                 125

Pro Gly Gly Tyr Gly Pro Gly Gly Ser Gly Pro Gly Gly Tyr Gly Pro
        130                 135                 140

Gly Gly Ser Gly Pro Gly Gly Tyr Gly Pro Gly Gly Ser Gly Pro Gly
145                 150                 155                 160

Gly Tyr Gly Pro Gly Gly Ser Gly Pro Gly Gly Tyr Gly Pro Gly Gly
            165                 170                 175

Ser Gly Pro Gly Gly Tyr Gly Pro Gly Gly Ser Gly Pro Gly Gly Tyr
        180                 185                 190

Gly Pro Gly Gly Ser Gly Pro Gly Gly Tyr Gly Pro Gly Gly Ser Gly
            195                 200                 205

Pro Gly Gly Tyr Gly Pro Gly Gly Ser Gly Pro Gly Gly Tyr Gly Pro
        210                 215                 220

Gly Gly Ser Gly Pro Gly Gly Tyr Gly Pro Gly Gly Ser Gly Pro Gly
225                 230                 235                 240

Gly Tyr Gly Pro Gly Gly Ser Gly Pro Gly Gly Tyr Gly Pro Gly Gly
            245                 250                 255

Ser Gly Pro Gly Gly Tyr Gly Pro Gly Gly Ser Gly Pro Gly Gly Tyr
        260                 265                 270

Gly Pro Gly Gly Ser Gly Pro Gly Gly Tyr Gly Pro Gly Gly Ser Gly
            275                 280                 285

Pro Gly Gly Tyr Gly Pro Gly Gly Ser Gly Pro Gly Gly Tyr Gly Pro
        290                 295                 300

Gly Gly Ser Gly Pro Gly Gly Tyr Gly Pro Gly Gly Ser Gly Pro Gly
305                 310                 315                 320

Gly Tyr Gly Pro Gly Gly Ser Gly Pro Gly Gly Tyr Gly Pro Gly Gly
            325                 330                 335

Ser Gly Pro Gly Gly Tyr Gly Pro Gly Gly Ser Gly Pro Gly Gly Tyr
        340                 345                 350

Gly Pro Gly Gly Ser Gly Pro Gly Gly Tyr Gly Pro Gly Gly Ser Gly
            355                 360                 365

Pro Gly Gly Tyr Gly Pro Gly Gly Ser Gly Pro Gly Gly Tyr Gly Pro
        370                 375                 380

Gly Gly Ser Gly Pro Gly Gly Tyr Gly Pro Gly Gly Ser Gly Pro Gly
385                 390                 395                 400

Gly Tyr Gly Pro Gly Gly Ser Gly Pro Gly Gly Tyr Gly Pro Gly Gly
            405                 410                 415

Ser Gly Pro Gly Gly Tyr Gly Pro Gly Gly Ser Gly Pro Gly Gly Tyr
        420                 425                 430

Gly Pro Gly Gly Ser Gly Pro Gly Gly Tyr Gly Pro Gly Gly Ser Gly
            435                 440                 445

Pro Gly Gly Tyr Gly Pro Gly Gly Ser Gly Pro Gly Gly Tyr Gly Pro
        450                 455                 460

Gly Gly Ser Gly Pro Gly Gly Tyr Gly Pro Gly Gly Ser Gly Pro Gly
465                 470                 475                 480

Gly Tyr Gly Pro Gly Gly Ser Gly Pro Gly Gly Tyr Gly Pro Gly Gly
            485                 490                 495

Ser Gly Pro Gly Gly Tyr Gly Pro Gly Gly Ser Gly Pro Gly Gly Tyr
        500                 505                 510

Gly Pro Gly Gly Ser Gly Pro Gly Gly Tyr Gly Pro Gly Gly Ser Gly
            515                 520                 525

Pro Gly Gly Tyr Gly Pro Gly Gly Ser Gly Pro Gly Gly Tyr Gly Pro
```

```
                530             535             540
Gly Gly Ser Gly Pro Gly Gly Tyr Gly Pro Gly Gly Ser Gly Pro Gly
545                 550             555             560

Gly Tyr Gly Pro Gly Gly Ser Gly Pro Gly Gly Tyr Gly Pro Gly Gly
                565             570             575

Ser Gly Pro Gly Gly Tyr Gly Pro Gly Gly Ser Gly Pro Gly Gly Tyr
                580             585             590

Gly Pro Gly Gly Ser Gly Pro Gly Gly Tyr Gly Pro Gly Gly Ser Gly
                595             600             605

Pro Gly Gly Tyr Gly Pro Gly Gly Ser Gly Pro Gly Gly Tyr Gly Pro
            610             615             620

Gly Gly Ser Gly Pro Gly Gly Tyr Gly Pro Gly Gly Ser Gly Pro Gly
625             630             635             640

Gly Tyr Gly Pro Gly Gly Ser Gly Pro Gly Gly Tyr Gly Pro Gly Gly
                645             650             655

Ser Gly Pro Gly Gly Tyr Gly Pro Gly Gly Ser Gly Pro Gly Gly Tyr
                660             665             670

Gly Pro Gly Gly Ser Gly Pro Gly Gly Tyr Gly Pro Gly Gly Ser Gly
                675             680             685

Pro Gly Gly Tyr Gly Pro Gly Gly Ser Gly Pro Gly Gly Tyr Gly Pro
            690             695             700

Gly Gly Ser Gly Pro Gly Gly Tyr Gly Pro Gly Gly Ser Gly Pro Gly
705             710             715             720

Gly Tyr Gly Pro Gly Gly Ser Gly Pro Gly Gly Tyr Gly Pro Gly Gly
                725             730             735

Ser Gly Pro Gly Gly Tyr Gly Pro Gly Gly Ser Gly Pro Gly Gly Tyr
                740             745             750

Gly Pro Gly Gly Ser Gly Pro Gly Gly Tyr Gly Pro Gly Gly Ser Gly
                755             760             765

Pro Gly Gly Tyr Gly Pro Gly Gly Ser Gly Pro Gly Gly Tyr Gly Pro
            770             775             780

Gly Gly Ser Gly Pro Gly Gly Tyr Gly Pro Gly Gly Ser Gly Pro Gly
785             790             795             800

Gly Tyr Gly Pro Gly Gly Ser Gly Pro Gly Gly Tyr Gly Pro Gly Gly
                805             810             815

Ser Gly Pro Gly Gly Tyr Gly Pro Gly Gly Ser Gly Pro Gly Gly Tyr
                820             825             830

Gly Pro Gly Gly Ser Gly Pro Gly Gly Tyr Gly Pro Gly Gly Ser Gly
                835             840             845

Pro Gly Gly Tyr Gly Pro Gly Gly Ser Gly Pro Gly Gly Tyr Gly Pro
            850             855             860

Gly Gly Ser Gly Pro Gly Gly Tyr Gly Pro Gly Gly Ser Gly Pro Gly
865             870             875             880

Gly Tyr Gly Pro Gly Gly Ser Gly Pro Gly Gly Tyr Gly Pro Gly Gly
                885             890             895

Ser Gly Pro Gly Gly Tyr Gly Pro Gly Gly Ser Gly Pro Gly Gly Tyr
                900             905             910

Gly Pro Gly Gly Ser Gly Pro Gly Gly Tyr Gly Pro Gly Gly Ser Gly
                915             920             925

Pro Gly Gly Tyr Gly Pro Gly Gly Ser Gly Pro Gly Gly Tyr Gly Pro
            930             935             940

Gly Gly Ser Gly Pro Gly Gly Tyr Gly Pro Gly Gly Ser Gly Pro Gly
945             950             955             960
```

Gly Tyr Gly Pro Gly Gly Ser Gly Pro
                965

<210> SEQ ID NO 35
<211> LENGTH: 135
<212> TYPE: DNA
<213> ORGANISM: Nephila clavipes

<400> SEQUENCE: 35
cggccgcata tgtctagacc agcaccggct ccgcgtccac tcccagaacc gctgccggct    60
cctcgtccga tcccagctcc gctgccgcgc ccagttccga tccgtccgct gccagcacct   120
aggggatcca agctt                                                    135

<210> SEQ ID NO 36
<211> LENGTH: 45
<212> TYPE: PRT
<213> ORGANISM: Nephila clavipes

<400> SEQUENCE: 36

Arg Pro His Met Ser Arg Pro Ala Pro Ala Pro Arg Pro Leu Pro Glu
1               5                   10                  15

Pro Leu Pro Ala Pro Arg Pro Ile Pro Ala Pro Leu Pro Arg Pro Val
            20                  25                  30

Pro Ile Arg Pro Leu Pro Ala Pro Arg Gly Ser Lys Leu
        35                  40                  45

<210> SEQ ID NO 37
<211> LENGTH: 174
<212> TYPE: DNA
<213> ORGANISM: Nephila clavipes

<400> SEQUENCE: 37
cggccgcata tgactagtgt ttctcaatcc cagcaggctt ctgtttccca atcccagcag    60
gcttccgtat cccaatccca gcaggcttct gtttcccaaa gccagcaggc ttctgtatcc   120
caatctcagc agtcttctaa cgcatactct cagcaggcta gcggatccaa gctt          174

<210> SEQ ID NO 38
<211> LENGTH: 58
<212> TYPE: PRT
<213> ORGANISM: Nephila clavipes

<400> SEQUENCE: 38

Arg Pro His Met Thr Ser Val Ser Gln Ser Gln Gln Ala Ser Val Ser
1               5                   10                  15

Gln Ser Gln Gln Ala Ser Val Ser Gln Ser Gln Gln Ala Ser Val Ser
            20                  25                  30

Gln Ser Gln Gln Ala Ser Val Ser Gln Ser Gln Gln Ser Ser Asn Ala
        35                  40                  45

Tyr Ser Gln Gln Ala Ser Gly Ser Lys Leu
    50                  55

<210> SEQ ID NO 39
<211> LENGTH: 762
<212> TYPE: DNA
<213> ORGANISM: Nephila clavipes

<400> SEQUENCE: 39
cggccgcata tgtctagacc agcaccggct ccgcgtccac tcccagaacc gctgccggct    60

```
cctcgtccga tcccagctcc gctgccgcgc ccagttccga tcgtttctca agtacagcag   120
gcatccatcc aacaggcaca gtcctcttct gctcagtccc gtcagtccgc cgttgctcag   180
caggcctccg tttctcaatc ccagcaggct tctgtttccc aatcccagca ggcttccgta   240
tcccaatccc agcaggcttc tgtttcccaa agccagcagg cttctgtatc ccaatctcag   300
cagtcttcta acgcatactc tgctgcgtct aacgccgcat ccagcgtttc tcaggcatcc   360
agcgcttcta gctacttcaa ctctcaggtt gttcagagca ccctgtcttc ttccctgcag   420
tcttctagcg ctctgagctc catcgcttac ggtcagacct ccgccaacat caacgacgta   480
gcagcagcgg ttgctcgtag cgtttctcaa tccctgggtg tttcccagca ggccgcacaa   540
agcgttatca gccagcagct cgcaagcgca ggtgcaggtg catctgctca gaccctcgca   600
caactgatct ccagcgcagt tcttcccctg gttcagcagt ctggtaccgt atctgccggt   660
caagaacaga gcatctccca ggcactctct agctccatcc tgtcttctct gagccaggta   720
gttgcccagc gtccgctgcc agcacctagg ggatccaagc tt                     762
```

<210> SEQ ID NO 40
<211> LENGTH: 254
<212> TYPE: PRT
<213> ORGANISM: Nephila clavipes

<400> SEQUENCE: 40

Arg Pro His Met Ser Arg Pro Ala Pro Ala Pro Arg Pro Leu Pro Glu
1               5                   10                  15

Pro Leu Pro Ala Pro Arg Pro Ile Pro Ala Pro Leu Pro Arg Pro Val
            20                  25                  30

Pro Ile Val Ser Gln Val Gln Gln Ala Ser Ile Gln Gln Ala Gln Ser
        35                  40                  45

Ser Ser Ala Gln Ser Arg Gln Ser Ala Val Ala Gln Gln Ala Ser Val
    50                  55                  60

Ser Gln Ser Gln Gln Ala Ser Val Ser Gln Gln Ala Ser Val
65                  70                  75                  80

Ser Gln Ser Gln Gln Ala Ser Val Ser Gln Gln Ala Ser Val
                85                  90                  95

Ser Gln Ser Gln Gln Ser Ser Asn Ala Tyr Ser Ala Ala Ser Asn Ala
            100                 105                 110

Ala Ser Ser Val Ser Gln Ala Ser Ser Ala Ser Ser Tyr Phe Asn Ser
        115                 120                 125

Gln Val Val Gln Ser Thr Leu Ser Ser Ser Leu Gln Ser Ser Ser Ala
    130                 135                 140

Leu Ser Ser Ile Ala Tyr Gly Gln Thr Ser Ala Asn Ile Asn Asp Val
145                 150                 155                 160

Ala Ala Ala Val Ala Arg Ser Val Ser Gln Ser Leu Gly Val Ser Gln
                165                 170                 175

Gln Ala Ala Gln Ser Val Ile Ser Gln Gln Leu Ala Ser Ala Gly Ala
            180                 185                 190

Gly Ala Ser Ala Gln Thr Leu Ala Gln Leu Ile Ser Ser Ala Val Ser
        195                 200                 205

Ser Leu Val Gln Gln Ser Gly Thr Val Ser Ala Gly Gln Glu Gln Ser
    210                 215                 220

Ile Ser Gln Ala Leu Ser Ser Ile Leu Ser Ser Leu Ser Gln Val
225                 230                 235                 240

Val Ala Gln Arg Pro Leu Pro Ala Pro Arg Gly Ser Lys Leu
                245                 250

<210> SEQ ID NO 41
<211> LENGTH: 48
<212> TYPE: DNA
<213> ORGANISM: Acropora nobilis

<400> SEQUENCE: 41
ggccggcctg gaggtggagg tggagctgcc tcctccgagg acgtcatc    48

<210> SEQ ID NO 42
<211> LENGTH: 54
<212> TYPE: DNA
<213> ORGANISM: Acropora nobilis

<400> SEQUENCE: 42
ggccccagcg gccgcagcag caccagcagg atcggcgccg gtggagtggc ggcc    54

<210> SEQ ID NO 43
<211> LENGTH: 33
<212> TYPE: DNA
<213> ORGANISM: Acropora nobilis

<400> SEQUENCE: 43
ggccggcctg gaggtggagg tggagctgtg agc    33

<210> SEQ ID NO 44
<211> LENGTH: 33
<212> TYPE: DNA
<213> ORGANISM: Acropora nobilis

<400> SEQUENCE: 44
ggccccagcg gccgcagcag caccagcagg atc    33

<210> SEQ ID NO 45
<211> LENGTH: 5009
<212> TYPE: DNA
<213> ORGANISM: Zea mays

<400> SEQUENCE: 45
ggggacaagt ttgtacaaaa aagcaggctg ctcgatccac ctaggcttgt tgcacatctt    60
tacccacaag tcatgttacc catctgccaa ggggtcatga atcccataca cctctaccat    120
ggaagcgaga cagggtaaca ctacgaggcc tttacaaagt tccactagct ttagaaaacc    180
cgctacaagg atccccgtc tgaccgccat cacagcaaaa cccgagaacc tccctacacc    240
gaccactccc ctactatcct tgcccctttc gggtaagata gtcttccact agctttccta    300
attagtcagc caagggcgtc ccataccacc cttatggtag cactgttttt ccgggtggtc    360
gctccatgtt ccaattaaca taataatctt atcatgaaca ataaataaca aaaaatgata    420
ataaaagcat gatcatgaat aatgtgtatc tcaatcccca aaaccacata agcaatagc    480 aggtactacc caaagttca gtggtaaaca aggtataaag atagtcaaac tgggttgacc    540
tattgggtct catcaaaatt aacctatgca gatcataatg attaacagta acattattgg    600
gtaaatagaa gtgatcaagg gcacaagttg ccttcaacga gatcctgctc agcagtctcc    660
acctgctgaa cacctgggtc ctcagtggct tgcttgtcta ctcgcaacaa tacaaacaaa    720
catggtatag gagaaattaa catcacacca aacagcagaa cagaatgcat gataatattc    780
tacgtgtcat aacgagatgg taggaacaag aatcactaaa ttcagagtta cgattttctg    840
aagttattag gtgcttagta tagaataaat caagtggata attttactct atgttttatg    900

-continued

```
gctaaacaga gttaccaagt gataaacaat attaatacaa aattaatgca actggaatgg     960
accaaaaagg agttaaaatg gatttttctat gaattaatct aggttttgga attgttttta    1020
tactaaatat tcattttctc ggcttattat taaccctggt attttatttg gactgcggac    1080
gcaaatgcta gaaactacag ggtccaatat atgaaaatca gggcatggat gtaattaatt    1140
tacaatagca gtggacggcg ggttaattca gtaattccct aggggcactt aagcaaatat    1200
ccatcgcaaa ggggtattgt tggatcccga ccgttggatc agatccgaag ccgagaata     1260 gatcgcgccc acacaactgc gtcgtgcact gaccaccctc cggttaagat tcgacggacc    1320
aaatttaatg aaatccaaac cacccacagc cccacgatca gcaatctacg gtccctctta    1380
acccagatga atcggtatcc gacttctaat ctaagcagtt cctcaatcga tcaacgctcc    1440
agggccttct tctatctccc aacgcagatc gagctacggt cgcttgcacc cgaggaacgc    1500
cgacacagcg agcggcggac cagcggttct gggtaatgat ttggagcaca acaatattg     1560 gcgcgacata ggaatgatgg caactattag gttgtgacct tactagtgtc agcggtgtgg    1620
gcagggtcgc ccacgggaaa ccagtgcgac ggtgctcccg gcttgttaat gacggtgtgc    1680
tggtcccgac acggtgatgc cccaaacgcc cccgccgtac gagaacaccg cagacgcccc    1740
tgctcgactc cgccctcggc ttcccgcgcc cacctcgcac ttcgacggcc gcaccgaccc    1800
tctgacctct ccttttctct cctttctcac tcctatcggt agctacaaca gaagcgactc    1860
ccaacgtggc gcaaaccctc gaagcatacg gctggggaag gtggcagcca ggtttatatc    1920
ctaggcgccc gaggaaatcg tgtggacggc tgttacgttt cgcccgcggg gcgcgattcg    1980
cgcgaagaag actgtatgcg aggtagggcc cactagcagt gagccatcac ccagggaagc    2040
gcgcatgcat cgattgacac gcgaccccaa cagtcaggcg acccgagtgt gcagacggtc    2100
gcgatggtga agtgctag ctcgcgcgga cgcgtagggg cattgggccg aaatgcgttt     2160
cagcggtcca acttcttttt ttcttgtctt ttttttcttc cttttccttt ctattttag     2220 atttcaaatt taagttcaaa ttttttgtgg tgaattttct aaaaatccac atatcagtat    2280
gaaaagaatt tatatataaa tctatttatt tatatattta ttttttttct atgttatttc    2340
caatttctaa aatgtaaatt aggttaaatc gccatttgga cactaatata tcttttattag   2400 tattactatt attatatgca caaccaaata aactccaaca tgatgcatcg attatttgta    2460
tgtcattggt taattattca cttaaatat gttccttaac gattctcatg aaacagaagg     2520
ccatgcacat aaagatgtat ccctttttc tatattccca gagttgggta ttacaacatt     2580
catctatgca ttctaggatt tcaattactc tcaatctttt agtatttgtt ccttcattgt    2640
caaatcactt ctcatctaac tactatgctt gtttaaccag cagaacaata ctacaacaat    2700
atccatttat aaaggcttta atagcaaact ttacatattc atatcatgtt aaggttgtca    2760
catgtgtaaa ggtgaagaga tcatgcatgt cattccacat aaatgaaaag aattcctata    2820
taaaaatgac atgttttgtt gtaggtagtg gaaattatct ttccagcaaa gaccatataa    2880
tccgataaag ctgataacta aatgtcaaaa tcgagtaagt gccatatcat ctatatctta    2940
tctgttgttt ggaaaagac aaaatccaaa aaaaatata tgagatctca catgtataaa      3000
tagctcccaa atcagtagtt aatacatctc ccataatatt ttcagcattc aaaaacacac    3060
caagcgaagc gcactagcaa cgacctaaca ccaatggcta ccaagatatt agccctcctt    3120
gcgcttcttg ccctttttagt gagcgcaaca aatgcgttca ttattccaca gtgctcactt    3180
gctcctagtg ccagtattcc acagttcctc ccaccagtta cttcaatggg cttcgaacat    3240
ccagccgtgc aagcctacag gctacaacta gcgcttgcgg cgagcgcctt acaacaacca    3300
```

```
attgcccaat tgcaacaaca atccttggca catctaaccc tacaaaccat tgcaacgcaa    3360
caacaacaac agtttctgcc atcactgagc cacctagccg tggtgaaccc tgtcacctac    3420
ttgcaacagc agctgcttgc atccaaccca cttgctctgg cgaacgtagc tgcataccag    3480
caacaacaac agctgcaaca gtttatgcca gtgctcagtc aactagccat ggtgaaccct    3540
gccgtctacc tacaactact ttcatctagc ccgctcgcgg tgggcaatgc acctacgtac    3600
ctacaacaac agttgctgca acaaattgta ccagctctga ctcagctagc tgtggcaaac    3660
cctgctgcct acttacaaca gttgcttcca ttcaaccaac tggctgtgtc aaactctgct    3720
gcgtacctac aacagcgaca acagttactt aatccattgg cagtggctaa cccattggtc    3780
gctaccttcc tgcagcagca acaacaattg ctgccataca accagttctc tttgatgaac    3840
cctgccttga tgaaccctgc cttgcagcaa cccatcgttg gaggtgccat cttttagatt    3900
acatatgaga tgtactcgac aatggtgccc tcataccgac atgtgtttcc tagaaataat    3960
caatatattg attgagattt atctcgatat atttctgaac tatgttcatc atataaataa    4020
ttgaaaacat caaatcataa ttttaaactc atgcttggtc aatacataga taatacaata    4080
ttacttcatc atcccaatga tgtcctagcc caacctattg aatgttaatg tttggttgtg    4140
tgagggtgtg tttataacat agatgtgatt atttgcgctt tttgttgagt atatacatat    4200
atggtatgtt gatttgatat agggatggac acatgctttg gccttggata ttcaaatcac    4260
ttgtacttgc acgaagcaaa acataatata tagtttagaa gtaaacttgt aactatgtcc    4320
aaacatgctc acacaaagtc ataccgcatt ataattttt ggtaaatatt caacacatgt    4380
attttttaca agaacccaaa ttttacagac aaatgcagca ttgtagacat gtagaattct    4440
ttgaagcatg tgaacttaac aacaccaatg tcattaaatc aactagaccc tatgagtaac    4500
aatttcgata ttgcaaacac caaattatgg aacttatttg ctgaaaaaat tatgatcaat    4560
gtgaagttta aattattata ccataaatat atcaaagatt ttttttgagga aggtaaaaat    4620 tgcatggaat gggctgccca acgtgatagc tcacttttat gctaggtagc attaccaaag    4680
atgggaacgt tctgatgaac accaaaccca ctcaaataat atttatattt gggttgttta    4740
gttgtaaaag tgaagaccca agtttaaagt accaattggc caatgccatt cgattgtttt    4800
gttcaaagag cacttggtac gtcatttgga ctcgtatctt agtccaatat attgcatttt    4860
gcttcaatgt gtagaatccg acaaagtgca tgttctaaaa ttgtaaatct aactaaatta    4920
gaaagcttgt tactaatttg atggtttatt aggtgtagct catcctgtgg tctcgctacg    4980
acccagcttt cttgtacaaa gtggtcccc                                      5009

<210> SEQ ID NO 46
<211> LENGTH: 705
<212> TYPE: DNA
<213> ORGANISM: Artificial sequence
<220> FEATURE:
<223> OTHER INFORMATION: Zea mays

<400> SEQUENCE: 46
gtgagcaagg gcgaggagac cacaatgggg gttattaagc cagatatgaa gatcaagctg      60
aagatggagg ggaatgtcaa tgggcacgcc ttcgttatcg aggggagggg cgaggggaag     120
ccatacgacg gcaccaacac gattaatctg gaggtcaagg agggggcgcc actgcctttc     180
tcgtacgata tcctcaccac ggccttcgcg tacggcaaca gggctttcac caagtacccg     240
gacgatatcc ccaactactt caagcagtcg ttcccagagg gctactcttg ggagcggaca     300
```

```
atgactttcg aggacaaggg catcgtgaag gtcaagtccg acattagcat ggaggaggat    360
tcattcatct acgagattca cctgaagggc gagaacttcc cgcccaatgg gcctgtgatg    420
cagaagaaga caactggctg gacgcgtcc accgagcgca tgtatgtgcg cgacggcgtg    480 ctcaagggg atgtgaagca taagctcctg ctcgagggcg ggggccacca tcgggtcgac    540
ttcaagacga tctaccgcgc taagaaggcc gtcaagctgc ccgactacca cttcgttgat    600
catcgcatcg agattctcaa ccacgacaag gattacaata aggtcactgt ttacgagtcg    660
gctgtggcga ggaatagcac tgacgggatg gacgagctct acaag              705
```

<210> SEQ ID NO 47
<211> LENGTH: 235
<212> TYPE: PRT
<213> ORGANISM: Artificial sequence
<220> FEATURE:
<223> OTHER INFORMATION: Zea mays
<400> SEQUENCE: 47

```
Val Ser Lys Gly Glu Glu Thr Thr Met Gly Val Ile Lys Pro Asp Met
1               5                   10                  15

Lys Ile Lys Leu Lys Met Glu Gly Asn Val Asn Gly His Ala Phe Val
            20                  25                  30

Ile Glu Gly Glu Gly Glu Gly Lys Pro Tyr Asp Gly Thr Asn Thr Ile
        35                  40                  45

Asn Leu Glu Val Lys Glu Gly Ala Pro Leu Pro Phe Ser Tyr Asp Ile
    50                  55                  60

Leu Thr Thr Ala Phe Ala Tyr Gly Asn Arg Ala Phe Thr Lys Tyr Pro
65                  70                  75                  80

Asp Asp Ile Pro Asn Tyr Phe Lys Gln Ser Phe Pro Glu Gly Tyr Ser
                85                  90                  95

Trp Glu Arg Thr Met Thr Phe Glu Asp Lys Gly Ile Val Lys Val Lys
            100                 105                 110

Ser Asp Ile Ser Met Glu Glu Asp Ser Phe Ile Tyr Glu Ile His Leu
        115                 120                 125

Lys Gly Glu Asn Phe Pro Pro Asn Gly Pro Val Met Gln Lys Lys Thr
    130                 135                 140

Thr Gly Trp Asp Ala Ser Thr Glu Arg Met Tyr Val Arg Asp Gly Val
145                 150                 155                 160

Leu Lys Gly Asp Val Lys His Lys Leu Leu Leu Glu Gly Gly Gly His
                165                 170                 175

His Arg Val Asp Phe Lys Thr Ile Tyr Arg Ala Lys Lys Ala Val Lys
            180                 185                 190

Leu Pro Asp Tyr His Phe Val Asp His Arg Ile Glu Ile Leu Asn His
        195                 200                 205

Asp Lys Asp Tyr Asn Lys Val Thr Val Tyr Glu Ser Ala Val Ala Arg
    210                 215                 220

Asn Ser Thr Asp Gly Met Asp Glu Leu Tyr Lys
225                 230                 235
```

<210> SEQ ID NO 48
<211> LENGTH: 717
<212> TYPE: DNA
<213> ORGANISM: Artificial sequence
<220> FEATURE:
<223> OTHER INFORMATION: Zea mays
<400> SEQUENCE: 48

```
gtcagcaagg gcgaggagct catcaaggag aatatgcaca tgaagctcta catggagggg    60
accgtggata atcaccattt caagtgcacg agcgagggcg aggggaagcc atacgagggc   120
acccagacga tgcgcatcaa ggtggtcgag ggcgggccac tcccattcgc cttcgacatt   180
ctcgcgacct ccttcctgta cggcagcaag acattcatca accacactca ggggattccg   240
gacttcttca agcagtcttt ccccgagggc ttcacatggg agagggttac cacgtacgag   300
gatggcgggg tcctgacagc tactcaggac acttcactcc aggatggctg cctgatctac   360
aacgtcaaga ttcggggcgt taacttcacc tccaatgggc cagtgatgca agaagaacg    420 ctcggctggg aggctttcac cgagacgctc tacccagctg acggcgggct ggagggccgg   480
aatgatatgg ctctcaagct ggtcggcggg tcgcacctga tcgctaacat taagacaact   540
taccgctcta agaagccagc caagaatctc aagatgcctg gcgtttacta cgtggattac   600
cgcctggaga ggatcaagga ggcgaacaat gagacctacg tggagcagca tgaggtcgcg   660
gttgctcgct acgctgggct gggcgggggg ctgaatggga tggatgagct ctacaag     717
```

<210> SEQ ID NO 49
<211> LENGTH: 239
<212> TYPE: PRT
<213> ORGANISM: Artificial sequence
<220> FEATURE:
<223> OTHER INFORMATION: Zea mays
<400> SEQUENCE: 49

```
Val Ser Lys Gly Glu Glu Leu Ile Lys Glu Asn Met His Met Lys Leu
1               5                   10                  15

Tyr Met Glu Gly Thr Val Asp Asn His His Phe Lys Cys Thr Ser Glu
            20                  25                  30

Gly Glu Gly Lys Pro Tyr Glu Gly Thr Gln Thr Met Arg Ile Lys Val
        35                  40                  45

Val Glu Gly Gly Pro Leu Pro Phe Ala Phe Asp Ile Leu Ala Thr Ser
    50                  55                  60

Phe Leu Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Val
                85                  90                  95

Thr Thr Tyr Glu Asp Gly Gly Val Leu Thr Ala Thr Gln Asp Thr Ser
            100                 105                 110

Leu Gln Asp Gly Cys Leu Ile Tyr Asn Val Lys Ile Arg Gly Val Asn
        115                 120                 125

Phe Thr Ser Asn Gly Pro Val Met Gln Lys Lys Thr Leu Gly Trp Glu
    130                 135                 140

Ala Phe Thr Glu Thr Leu Tyr Pro Ala Asp Gly Gly Leu Glu Gly Arg
145                 150                 155                 160

Asn Asp Met Ala Leu Lys Leu Val Gly Gly Ser His Leu Ile Ala Asn
                165                 170                 175

Ile Lys Thr Thr Tyr Arg Ser Lys Lys Pro Ala Lys Asn Leu Lys Met
            180                 185                 190

Pro Gly Val Tyr Tyr Val Asp Tyr Arg Leu Glu Arg Ile Lys Glu Ala
        195                 200                 205

Asn Asn Glu Thr Tyr Val Glu Gln His Glu Val Ala Val Ala Arg Tyr
    210                 215                 220

Ala Gly Leu Gly Gly Gly Leu Asn Gly Met Asp Glu Leu Tyr Lys
225                 230                 235
```

<210> SEQ ID NO 50
<211> LENGTH: 705
<212> TYPE: DNA
<213> ORGANISM: Artificial sequence
<220> FEATURE:
<223> OTHER INFORMATION: Zea mays

<400> SEQUENCE: 50

```
gtctcaaagg gggaggagga caatatggct atcatcaagg agttcatgcg gttcaaggtt      60
cacatggagg gcagcgtcaa tgggcacgag ttcgagatcg agggcgaggg ggagggcagg     120
ccgtacgagg gcacacagac tgccaagctc aaggttacca agggcgggcc actcccattc     180
gcttgggaca tcctgtcacc gcagttcatg tacgggtcca aggcctacgt caagcaccca     240
gcggacattc ctgattacct caagctgagc ttccccgagg gcttcaagtg ggagcgggtc     300
atgaacttcg aggacggcgg ggtggtcacc gttacgcagg actccagcct ccaggatggc     360
gagttcatct acaaggtgaa gctgaggggg accaatttcc catcggacgg ccccgtcatg     420
cagaagaaga cgatgggctg ggaggcgtcg tctgagcgca tgtacccaga ggatgggct     480
ctgaagggcg agattaagca gaggctcaag ctgaaggacg gcgggcacta cgatgctgag     540
gtgaagacca cgtacaaggc caagaagcca gttcagctcc ctggcgctta caacgtgaat     600
atcaagctgg acattacatc ccataacgag gattacacta tcgtcgagca gtacgagcgg     660
gctgagggca ggcatagcac ggggggatg gatgagctgt acaag             705
```

<210> SEQ ID NO 51
<211> LENGTH: 235
<212> TYPE: PRT
<213> ORGANISM: Artificial sequence
<220> FEATURE:
<223> OTHER INFORMATION: Zea mays

<400> SEQUENCE: 51

```
Val Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
    50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
    130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190
```

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
        210                 215                 220

His Ser Thr Gly Gly Met Asp Glu Leu Tyr Lys
225                 230                 235

<210> SEQ ID NO 52
<211> LENGTH: 774
<212> TYPE: DNA
<213> ORGANISM: Artificial sequence
<220> FEATURE:
<223> OTHER INFORMATION: Zea mays

<400> SEQUENCE: 52

| | | | | |
|---|---|---|---|---|
| gttagcaagg | gggaggagct | gttcactggc | gtggttccga ttctggtgga gctggatggg | 60 |
| gatgtcaatg | ggcacaagtt | ctcggtgtcc | ggcgaggggg agggcgacgc tacctacggg | 120 |
| aagctcacgc | tgaagttcat | ctgcaccacg | ggcaagctcc cagttccatg gccaaccctc | 180 |
| gtgacaactc | tgacgtgggg | cgttcagtgc | ttcgctcggt accccgacca catgaagcag | 240 |
| catgatttct | tcaagtcggc | catgccagag | ggctacgtgc aggagcgcac aatcttcttc | 300 |
| aaggacgatg | gcaactacaa | gacaagggcc | gaggtcaagt tcgaggggga cactctcgtt | 360 |
| aaccggatcg | agctgaaggg | cattgacttc | aaggaggatg gaatatcct cggccacaag | 420 |
| ctggagtaca | acgctatctc | tgacaatgtg | tacattaccg ccgataagca gaagaacggc | 480 |
| attaaggcga | atttcaagat | ccgccacaac | attgaggacg gctcagtgca gctggcggat | 540 |
| cattaccagc | agaacacccc | aatcggggac | ggccctgtcc tcctgccgga taatcactac | 600 |
| ctctccacgc | agagcgctct | gtcgaaggac | ccgaatgaga gagggatca tatggtgctc | 660 |
| ctggagttcg | tcacagccgc | ggggattact | ctcggcatgg acgagctgta caagcggcgg | 720 |
| gggtcgggct | gctccattat | gaatctgatg | tgcggctcca cttgcgctgc ctga | 774 |

<210> SEQ ID NO 53
<211> LENGTH: 257
<212> TYPE: PRT
<213> ORGANISM: Artificial sequence
<220> FEATURE:
<223> OTHER INFORMATION: Zea mays

<400> SEQUENCE: 53

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

```
Asp Phe Lys Glu Asp Gly Asn Ile Leu Gly His Lys Leu Glu Tyr Asn
            130                 135                 140

Ala Ile Ser Asp Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys Arg Arg
225                 230                 235                 240

Gly Ser Gly Cys Ser Ile Met Asn Leu Met Cys Gly Ser Thr Cys Ala
                245                 250                 255

Ala
```

<210> SEQ ID NO 54
<211> LENGTH: 616
<212> TYPE: DNA
<213> ORGANISM: Nicotiana tabacum

<400> SEQUENCE: 54

```
cacgaaatag ttatgattgc cagttataac atttcattaa tgtcattaaa tgctcataat    60
gactcgatta cgagaaggaa gagacattgt acttagaaat agctataaaa ggaagagaaa   120
tgacatttgt gtggatacgt tctgattatt aatagaatat acttatttac tttgctttat   180
attgattgtt tcgttatttc ttattctaat tttcctttct cattacaaaa aagttccgtt   240
atttgattat cagtaacccg aatacttttat aaaataagct ttgaccgaaa ttcctatttt   300
ctggttaaac acacaataca ttttattcta tatgcagata aggatgtggc tgccaaataa   360
ccagacacta gacacaagcc ttttcttcc tctcaccaac cagtcagtca gtcatatttg    420
gttaatccaa tgaagtaact taacggtgcg ttgagcacgt gcataccatc taacattacc   480
actcctaaca ccacctacgt tcaagtagta taaacacgac ataagaataa ataaagctca   540
tctcattgta gttcaattta atactagta agtccagtca cataaaaatt ttccactctt    600
ctacctttca tttctg                                                    616
```

<210> SEQ ID NO 55
<211> LENGTH: 539
<212> TYPE: DNA
<213> ORGANISM: Nicotiana tabacum

<400> SEQUENCE: 55

```
cacgaaatag ttatgattgc cagttataac atttcattaa tgtcattaaa tgctcataat    60
gactcgatta cgagaaggaa gagacattgt acttagaaat agctataaaa ggaagagaaa   120
tgacatttgt gtggatacgt tctgattatt aatagaatat acttatttac tttgctttat   180
attgattgtt tcgttatttc ttattctaat tttcctttct cattacaaaa aagttccgtt   240
atttgattat cagtaacccg aatacttttat aaaataagct ttgaccgaaa ttcctatttt   300
ctggttaaac acacaataca ttttattcta tatgcagata aggatgtggc tgccaaataa   360
ccagacacta gacacaagcc ttttcttcc tctcaccaac cagtcagtca gtcatatttg    420
```

```
gttaatccaa tgaagtaact taacggtgcg ttgagcacgt gcataccatc taacattacc      480
actcctaaca ccacctacgt tcaagtagta taaacacgac ataagaataa ataaagctc       539
```

<210> SEQ ID NO 56
<211> LENGTH: 1613
<212> TYPE: DNA
<213> ORGANISM: Nicotiana plumbaginifolia

<400> SEQUENCE: 56

```
ccaggtgaac ccgtaactag tttgttgtat tcgcctctgc tgataggtga ttataacctc      60
ctcaaaagca atttctactc catttcacct ataaaataat cagaaaactt aagttatata     120
catcagtaaa taaattttac accataagat aaaaattgct ttcgcaacgg ttaagggtgg     180
catgtgggcc ggggccggtt ctaagtgggc tttacgggcc cgatcctaag taggcccagt     240
cctaagtggg ccggtcctaa gtggtcccgg gtttcgcagg cttcttgttg taatcggcct     300
tggattggga ccacgaacta acggtcccgg gttaagtggg ccggtcccgg gcctaagtgg     360
gcccaacgaa tactttctat tttttaaaaa taatttttag aagttagaga aaaaaaatga     420
aaataaaaat atttaaggca attccttgta aattatatta tagaattgtg acctaaattt     480
tttaattcaa atttaaagat aaaaatattg taaagaggta ttcaaagcaa tgtgttatat     540
atatatatat atatatacta agtgtatagt atataagcta taattatata tatcttaaga     600
tgtatatata gtattatagt atagtatagt aatcttaaca tgtatatata gctataaaaa     660
gtatggggtt aaaacaaagt tgggaaaggt tattttataa attgccaacg gctattttag     720
caggtaaaac ggccatattt taaatgccat aacggctata atgtggcaga tttattttt       780 aaaaaaacta accgttgggc ccgaataggc ctttttagga ccgcttgaac cggcccactt     840
cccagccggt cccggtctcg cgggcctcgc ctatggaacc gacccactac ccagcccacc     900
tccccacggt cccgatccta ttcggttaga accgtctagg cccaccgccc atttgggctt     960
gcggtcttgg gccggacctg aacctaaccg gcccacatgc catccttact aacggtaaat    1020
aacttagaag ttattgtata cgtatgatcg agctgttgga cttgtagtat caaactttca    1080
atgacgcatc aaaattaatt atggtagctt cgcgttggga cacttgtaca tgcattaact    1140
tgatttcaat ttctttttta aaaatatttg tctattgtca atttaccact cgtacttgaa    1200
gtgggcctat ttgacaggtc agctaaatac agaagtgtat gaacaatgcg tggccaagag    1260
taactcttat gctaaagaca agtggatatt atattgcaat aatccacaat cagacgtggc    1320
aaatttggat tggctataag agagcaaatc ttcattaggt aagttttta aacataaaaa     1380 gtatctaaaa aaatcttgtc atgtttaacg gtgctgaact ttgccaaatg acaagaatg      1440 caaaaggtta aaattgcaat ccaccaattg aaaagtagat atagatactc aaggataagg    1500
gtctttgggc ctgtaaagcc atttatatac acttagtgca aagcccatga aactcaagcc    1560
tcaaatcaac tctttctttt tgtgcattca agagttatca ttttactcct aca           1613
```

<210> SEQ ID NO 57
<211> LENGTH: 46
<212> TYPE: DNA
<213> ORGANISM: Artificial sequence
<220> FEATURE:
<223> OTHER INFORMATION: Zea mays

<400> SEQUENCE: 57

```
ggggacaact ttctataca aagttgcagg ccggcctgga ggtgga                     46
```

```
<210> SEQ ID NO 58
<211> LENGTH: 45
<212> TYPE: DNA
<213> ORGANISM: Artificial sequence
<220> FEATURE:
<223> OTHER INFORMATION: Zea mays

<400> SEQUENCE: 58
ggggacaact ttattataca aagttgtggc cccagcggcc gcagc              45

<210> SEQ ID NO 59
<211> LENGTH: 47
<212> TYPE: DNA
<213> ORGANISM: Artificial sequence
<220> FEATURE:
<223> OTHER INFORMATION: Zea mays

<400> SEQUENCE: 59
ggccggcctg gaggtggagg tggagctgtt agcaaggggg aggagct            47

<210> SEQ ID NO 60
<211> LENGTH: 50
<212> TYPE: DNA
<213> ORGANISM: Artificial sequence
<220> FEATURE:
<223> OTHER INFORMATION: Zea mays

<400> SEQUENCE: 60
ggccccagcg gccgcagcag caccagcagg atccttgtac agctcgtcca          50

<210> SEQ ID NO 61
<211> LENGTH: 3633
<212> TYPE: DNA
<213> ORGANISM: Zea mays

<400> SEQUENCE: 61
ggagagaagg aagatgttgg gtaggaaaag aatagagtta gaaagaaatg atataatata     60
tattatttgg tatagagtta gataaaaagt aaatatgatt atagagaatt gttgtatatg    120
atagataatt ttactgacta gaacagaata tttgtattaa agtacaaatt tagagtagta    180
tgagtatgga taaggctgag cgcagtggca gactggaccc cgaacgctac tcgacatagc    240
gtgtactcaa tgctgcagcc gtgtactcga tgcggaactc tattttagcg tgggcggctt    300
cgaacgacac tggcagggtt tgtacgatgc tgaacgctat ctcaaccagc cagccgcgcg    360
gtgccacgtg ggtgagcgga ccgtgactcc ctcggctgct tgcctggtgt aaataatatt    420
atatatgata attggtatag ggttgagata tagagtaaac atgagtgcgg aaggattgtg    480
gtatagagta aagaatttgc tgactaggat agaatatttc ttttagagta aaaatttagt    540
gttgtatgat tgtggatagc ttaagctaag agcaacttca agtaattagg tatatgattt    600
tgtgaaggta aatttagtta atattaaaaa aaaattgtat ccaatagact ttgtaaacga    660
ctcttcaaat ttagtggctc tctataactt cgtattcacc tctctatttt ttaataacct    720
gttttacttt ttatttagtc tatagattta ttgagtctgt tgaattaacc tacactttttt   780
cctgtaaaat ctaatttaga gactagctaa attattaact ttagctagtc tttttagcta    840
atccttgctc tcaaggtaat ttttcaaaag aaaaaaaga aacaggcaag ccgcaacgtg     900
aatccaagca gtccgcgcgt caccccgccg ccgaaggaac aagaacaaac cgcccccaaa    960
ttagctgtca acccgtcgct tccttcacgt aatcacgtct cctccgccgc ccttgctaag   1020
caaacgcaac ctgcaactgc aaacccctcc tccgattcct ccccgcacg cggaagcccc   1080
```

```
ccgcagctct tcgtccccgg aggaccaaga ccaccaccgg agatgtcgta cgcctacctc    1140
ttcaagtaca tcatcatcgg cgacacaggt ccgtctcgtc ccgtcagccc tttccttcc    1200 tccgttctcc gattggatcc acgcgcctcc caacctgctg ccgccgccgc ggcgagatgg    1260
agatccattc taatccgctt gcccgctcgc gatgacgctg acggccttcc tctgcttgcc    1320
tttgctttgc tgcaggcgtc ggtaagtcgt gcctgctgct gcagttcacc gacaagcgct    1380
tccagcccgt ccacgacctc accatcggcg tcgagttcgg ggcccggatg atcaacatcg    1440
acaacaagcc catcaagctc cagatttggg atacggtcgg tgacctgttt gtccgctata    1500 cttccttcg ttcttaccgc tatactttcc ttcgttctta cgtatccctt agatacttgc    1560
acttgcttca ggtcgatcta ccgctaccaa ttaaggcaac ataatagctt cctcagttgc    1620
ttatggcctt atgggaactc aattctggtt gccaactgga atttaggatg tccagttagt    1680
gtggcataaa gttattttg gtctgtagt tcgagatgaa aaacacttc cgcagtcagt    1740 tggcccagtt ccagcagctg ctgcttctgc ttctgtggcc gtctgcctcc tcacatgtca    1800
ctgtagcgtc gaactagcag cggctgatac aagcagccag tatctctttg agctccgaaa    1860
ctacaacatt ttggatatct cttttttta tcagtgtgcc cacccactg gagttatctg    1920 actattagcg cactgaacca tatgaccgtt tgttgattta agttatcctt gctgccacgc    1980
cacgatgtta atgatgtgga atacccatgt ggccggccac atgcatcatt tatctgtctt    2040
gattgtgttg tctcttaaca ttatgcaggc tggtcaagag tcattcagat ccataactag    2100
atcatactac agaggagctg ctggtgctct tttggtctat gatatcacta ggtgattacc    2160
cccacataag ttctaagctg cttgggcggt attcttagc cgcggtttcc tgatagtgtt    2220
gatactggca tccaaatcca tgttggacta atttcaggag ggagactttc aatcaccttg    2280
caagctggct ggaggatgca aggcagcacg cgaatgctaa catgacgata atgcttgttg    2340 ggataagtg tgatctgtct cacaggcgtg cagtgagcta tgaggaaggc gagcagttcg    2400
caaaggaaca tggtcttatc ttcatggagg cctctgcaaa gaccgcgcag aatgtcgagg    2460
aggtgatgct tgattcttgg tgcatctatt tgcagttaaa ttattttcca atttcctcat    2520
gcagcttgaa ctttttaaat gcaggcattt gttaagactg ctggagcaat ctacaagaaa    2580
atccaagatg gcgttttcga tgtatctaat gaggtatctt ttgatctcaa accattcctt    2640
ttgctctgct taaggaaaat gtagtgagcc ccttcgatat tactctaggt accatttaaa    2700
gaactaatgt agattcttaa cctatgtatt acagcccaaa acctttcctg agatgagtgc    2760
cagatactca tgtacccttg tgttctttta ggagtactgt atatgggctg ccttacgatg    2820
tgcataagtc tatctaatag aaagtttaaa ttcttcttac tacctttata aactgaaatg    2880
ttggagtgag ggtagccaaa catggaaaac tgaagaggac aatatcgaca ggcacagttc    2940
ctgtttgtcc ttgttttctc ttgaaacttg ctgttttttt tatggaaact agatattctc    3000
accgagtcat tgcgggactg cgggttcgaa gcaacctctc cgcatttgca agggcaagac    3060
ttcggttttt ccctctccca gtgggcccca ctcatgtaga agcctccggc actggttctg    3120
gcttttttta gatattctcc tatagtgaaa atgtcatttg cccaccagga acccttgtcc    3180
tgctctcata acatttgct tgcttacagc acgtatctgt taccggcaca tgagtatgat    3240
ctcatacatc ttttgtcaaa ttcgcagtct tatgggatca aagttggata tgtagtccct    3300
ggccaatctg gaggtgctgg tagctcttct caaggtggtg ctgctgcag ctaatctgct    3360 aacgccctta tgtacaaagg catatctgcg gtgtagctgc gttatctcta tgttgctgag    3420
cgtaaaatag ttactgctcc agggtgcttt gttatttgat gcaccaacgg gtggcagtgc    3480
```

```
ctgaacgatt tgagacattc agttttattt atgtcaggtg ttcataaaca ttctgtaaat    3540
cactagattc ttcaccgtca ttcgtcatta agcgctcaca aattctgtcc gtttgcgcgt    3600
gtaaataaga tacctcgatg catcgttggt gtg                                 3633

<210> SEQ ID NO 62
<211> LENGTH: 1125
<212> TYPE: DNA
<213> ORGANISM: Zea mays

<400> SEQUENCE: 62
ggagagaagg aagatgttgg gtaggaaaag aatagagtta gaaagaaatg atataatata      60
tattatttgg tatagagtta gataaaaagt aaatatgatt atagagaatt gttgtatatg     120
atagataatt ttactgacta gaacagaata tttgtattaa agtacaaatt tagagtagta     180
tgagtatgga taaggctgag cgcagtggca gactggaccc cgaacgctac tcgacatagc     240
gtgtactcaa tgctgcagcc gtgtactcga tgcggaactc tattttagcg tgggcggctt     300
cgaacgacac tggcagggtt tgtacgatgc tgaacgctat ctcaaccagc cagccgcgcg     360
gtgccacgtg ggtgagcgga ccgtgactcc ctcggctgct tgcctggtgt aaataatatt     420
atatatgata attggtatag ggttgagata tagagtaaac atgagtgcgg aggattgtgg     480
tatagagtaa agaattttgc tgactaggat agaatatttc ttttagagta aaaatttagt     540
gttgtatgat tgtggatagc ttaagctaag agcaacttca agtaattagg tatatgattt     600
tgtgaaggta aatttagtta atattaaaaa aaaattgtat ccaatagact ttgtaaacga     660
ctcttcaaat ttagtggctc tctataactt cgtattcacc tctctatttt ttaataacct     720
gttttacttt ttatttagtc tatagattta ttgagtctgt tgaattaacc tacacttttt     780
cctgtaaaat ctaatttaga gactagctaa attattaact ttagctagtc ttttagcta      840 atccttgctc tcaaggtaat ttttcaaaag aaaaaaaaga aacaggcaag ccgcaacgtg     900
aatccaagca gtccgcgcgt caccccgccg ccgaaggaac aagaacaaac cgcccccaaa     960
ttagctgtca acccgtcgct tccttcacgt aatcacgtct cctccgccgc ccttgctaag    1020
caaacgcaac ctgcaactgc aaaccctcc tccgattcct cccccgcacg cggaagcccc     1080
ccgcagctct tcgtccccgg aggaccaaga ccaccaccgg agatg                    1125

<210> SEQ ID NO 63
<211> LENGTH: 39
<212> TYPE: DNA
<213> ORGANISM: Zea mays

<400> SEQUENCE: 63
gctcgatcca cctaggctgg agagaaggaa gatgttggg                             39

<210> SEQ ID NO 64
<211> LENGTH: 51
<212> TYPE: DNA
<213> ORGANISM: Zea mays

<400> SEQUENCE: 64
cacagctcca cctccacctc caggccggcc catctccggt ggtggtcttg g              51

<210> SEQ ID NO 65
<211> LENGTH: 52
<212> TYPE: DNA
<213> ORGANISM: Zea mays
```

```
<400> SEQUENCE: 65
tgctggtgct gctgcggccg ctggggcctc gtacgcctac ctcttcaagt ac        52

<210> SEQ ID NO 66
<211> LENGTH: 37
<212> TYPE: DNA
<213> ORGANISM: Zea mays

<400> SEQUENCE: 66
cgtagcgaga ccacaggaca caccaaacga tgcatcg                         37

<210> SEQ ID NO 67
<211> LENGTH: 49
<212> TYPE: DNA
<213> ORGANISM: Zea mays

<400> SEQUENCE: 67
tgctggtgct gctgcggccg ctggggccta atctgctaac gcccttatg            49

<210> SEQ ID NO 68
<211> LENGTH: 1102
<212> TYPE: DNA
<213> ORGANISM: Hordeum vulgare

<400> SEQUENCE: 68
gctagctggt aggaggagct aggatcgaat cggatcgacc ggcatgggga ggtcgccgtg    60
ctgcgagaag gagcacacca acaaggggc gtggaccaag gaggaggacc agcggctgat   120
cgcctacatc agggccaacg cgagggctg ctggcgctcg ctgcccaagg cggcgggcct   180
gctgcgctgc ggcaagagct gccgcctccg ctggatgaac tacctccgcc ccgacctcaa   240
gcgcggcaac ttcaccgacg acgaggacga gctcatcatc cgcctccaca gcctgctcgg   300
caacaagtgg tctctcatcg ccggccagct gccgggcagg acggacaacg agatcaagaa   360
ctactggaac acgcacatca agcgcaagct cctctcccgc ggcatggacc cgcacacgca   420
ccgcccgctc acgccgtca tcgacgccgc gcgccgacc cgcccggcac agatagccgt   480
gccggcgagg gcggcgccca ccacgatgtt cgccctgcca accaaacagc agcagccgcc   540
ggtgccggtc gagtcgtcgg acgacgacgg cagcagcggc gcgacgagca ccggggagcc   600
acggtgcccc gacctcaacc tcgacctgtc cgtgggcccg ccggcggccg acacgccgac   660
gtcgcacccg gtctgcctct gccgccacct cggcttccgc ggcggggagg cgtgcagctg   720
ccggcaggcc gacagcgcgg gctcccaggg cggcggcttt agatatttca ggccgttgga   780
ggagggccag tacatatgag agacgacggg acggctaggc cctagaactc cacagcaatt   840
tgtaagacag ggaaattttt ctacttactc ctcctccagt ccacagcacc tagcgctgct   900
ggctggctca caaaacggtg aaaacaaaat ctaatctgtt catatccttc cttgtacgcc   960
aaaaccgcga atttgtccgc tctcttttgt tgttggttgg tgctgttgcg ttgggtggga  1020
aaaaccaggg gataatgtga caaaggttgg tgtgtatttt gtggaaaaag ggagggcctg  1080
atgtgaggca gcgaccacgg tc                                          1102
```